US011578317B2

(12) United States Patent
Schmidt-Dannert et al.

(10) Patent No.: US 11,578,317 B2
(45) Date of Patent: Feb. 14, 2023

(54) SELF-ASSEMBLING PROTEIN SCAFFOLDS AND METHODS

(71) Applicant: REGENTS OF THE UNIVERSITY OF MINNESOTA, Minneapolis, MN (US)

(72) Inventors: Claudia Schmidt-Dannert, Shoreview, MN (US); Maureen B. Quin, Saint Paul, MN (US); Guoqiang Zhang, Saint Paul, MN (US); Kelly Kristen Wallin, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/632,941

(22) PCT Filed: Jul. 24, 2018

(86) PCT No.: PCT/US2018/043491
§ 371 (c)(1),
(2) Date: Jan. 22, 2020

(87) PCT Pub. No.: WO2019/216930
PCT Pub. Date: Nov. 14, 2019

(65) Prior Publication Data
US 2020/0157153 A1     May 21, 2020

Related U.S. Application Data

(60) Provisional application No. 62/536,650, filed on Jul. 25, 2017.

(51) Int. Cl.
*C12N 9/96* (2006.01)
*C12N 9/06* (2006.01)
*C12N 9/74* (2006.01)
*C12N 15/62* (2006.01)
*C07K 14/255* (2006.01)
*C07K 14/32* (2006.01)

(52) U.S. Cl.
CPC .............. *C12N 9/96* (2013.01); *C12N 9/0014* (2013.01); *C12N 9/6429* (2013.01); *C12N 15/62* (2013.01); *C07K 14/255* (2013.01); *C07K 14/32* (2013.01)

(58) Field of Classification Search
CPC .................. C12N 15/62; C12N 9/96
See application file for complete search history.

(56) References Cited

U.S. PATENT DOCUMENTS

| 9,909,143 B2* | 3/2018 | Schmidt-Dannert .... A62D 3/02 |
| 2012/0210459 A1* | 8/2012 | Kerfeld .............. C12N 15/8261 800/278 |
| 2014/0295520 A1* | 10/2014 | Schmidt-Dannert .... A62D 3/02 435/170 |

OTHER PUBLICATIONS

Quin. Spatial organization of multi-enzyme biocatalytic cascades. Organics & Biomolecular Chemistry. vol. 15, No. 20, May 2017.*
Pitts. Structural insight into the Clostridium difficile ethanolamine utilisation microcompartment. PLoS One. 2012;7(10):e48360. Epub Oct. 29, 2012.*
Zhang. Developing a Protein Scaffolding System for Rapid Enzyme Immobilization and Optimization of Enzyme Functions for Biocatalysis. ACS Synth Biol Actions. Aug. 16, 2019;8(8):1867-1876.*
Zhang. Self-Assembling Protein Scaffold System for Easy in Vitro Coimmobilization of Biocatalytic Cascade Enzymes. ACS Catal. 2018, 8, 5611-5620.*
Mateo. Improvement of enzyme activity, stability and selectivity via immobilization techniques. Enzyme and Microbiol Technology 40 (2007) 1451-1463.*
Agapakis et al., Natural strategies for the spatial optimization of metabolism in synthetic biology. *Nat Chem Biol* 8, 527-535 (2012).
Altschul et al., Basic local alignment search tool. *J Mol Biol* 215, 403-410 (1990).
Andersen et al., New unstable variants of green fluorescent protein for studies of transient gene expression in bacteria. *Appl Environ Microbiol* 64, 2240-2246 (1998).
Barbosa et al., Quantifying brain iron deposition in patients with Parkinson's disease using quantitative susceptibility mapping, R2 and R2. *Magn Reson Imaging* 33, 559-565 (2015).
Benkert et al., QMEAN server for protein model quality estimation. *Nucleic Acids Res* 37, W510-514 (2009).
Berman et al., The Protein Data Bank. *Nucleic Acids Res* 28, 235-242 (2000).
Biasini et al., Swiss-Model: modelling protein tertiary and quaternary structure using evolutionary information. *Nucleic Acids Res* 42, W252-258 (2014).
Bommarius et al., A novel chimeric amine dehydrogenase shows altered substrate specificity compared to its parent enzymes. *Chem Commun (Camb)* 50, 14953-14955 (2014).

(Continued)

*Primary Examiner* — Yong D Pak
(74) *Attorney, Agent, or Firm* — Mueting Raasch Group

(57) ABSTRACT

A protein scaffold includes a plurality of EutM subunits and a multi-enzyme cascade. The multi-enzyme cascade includes a first enzyme attached to the first EutM subunit and a second enzyme attached to the second EutM subunit. The scaffold may be formed by a method that generally includes incubating a plurality of EutM subunits under conditions allowing the EutM subunits to self-assemble into a protein scaffold, attaching a first enzyme of a multi-enzyme cascade to a first EutM subunit, and attaching a second enzyme of the multi-enzyme cascade to a second EutM subunit. The scaffold may be self-assembled in vivo or in vitro. Each enzyme may be, independently of any other enzyme, attached to its EutM subunit in vivo or in vitro. Each enzyme may be, independently of any other enzyme, attached to its EutM subunit before or after the scaffold is assembled.

31 Claims, 27 Drawing Sheets
Specification includes a Sequence Listing.

(56) References Cited

OTHER PUBLICATIONS

Chado, et al., "Role of Dimension and Spatial Arrangement on the Activity of Biocatalytic Cascade Reactions on Scaffolds". ACS Catalysis, 2016. 6(8): p. 5161-5169.
Choi et al., Novel, versatile, and tightly regulated expression system for Escherichia coli strains. Appl Environ Microbiol 76, 5058-5066 (2010).
Choudhary et al., Engineered protein nano-compartments for targeted enzyme localization. PLoS One 7, e33342 (2012).
Clomburg et al., Industrial biomanufacturing: The future of chemical production. Science 355, (2017).
Dudley et al., Cell-free metabolic engineering: biomanufacturing beyond the cell. Biotechnol J 10, 69-82 (2015).
Dueber et al., Synthetic protein scaffolds provide modular control over metabolic flux. Nat Biotechnol 27, 753-759 (2009).
Eddy, Where did the BLOSUM62 alignment score matrix come from? Nat Biotechnol 22, 1035-1036 (2004).
Edgar, Muscle: multiple sequence alignment with high accuracy and high throughput. Nucleic Acids Res 32, 1792-1797 (2004).
Fairhead et al., SpyAvidin hubs enable precise and ultrastable orthogonal nanoassembly. J Am Chem Soc 136, 12355-12363 (2014).
Fan et al., Interactions between the termini of lumen enzymes and shell proteins mediate enzyme encapsulation into bacterial microcompartments. Proc Natl Acad Sci U S A 109, 14995-15000 (2012).
Ferner-Ortner-Bleckmann et al., Surface-layer lattices as patterning element for multimeric extremozymes. Small 9, 3887-3894 (2013).
Fessner, Systems Biocatalysis: Development and engineering of cell-free "artificial metabolisms" for preparative multi-enzymatic synthesis. N Biotechnol 32, 658-664 (2015).
France, et al., "Constructing Biocatalytic Cascades: In Vitro and in Vivo Approaches to de Novo Multi-Enzyme Pathways". ACS Catalysis, 2017. 7(1): p. 710-724.
Fu et al., Interenzyme substrate diffusion for an enzyme cascade organized on spatially addressable DNA nanostructures. J Am Chem Soc 134, 5516-5519 (2012).
Garcia-Galan, et al., "Potential of Different Enzyme Immobilization Strategies to Improve Enzyme Performance". Advanced Synthesis & Catalysis, 2011. 353(16): p. 2885-2904.
Giessen et al., Encapsulation as a Strategy for the Design of Biological Compartmentalization. J Mol Biol 428, 916-927 (2016).
Gradisar et al., De novo design of orthogonal peptide pairs forming parallel coiled-coil heterodimers. J Pept Sci 17, 100-106 (2011).
Held et al., Engineering formation of multiple recombinant Eut protein nanocompartments in E. coli. Sci Rep 6, 24359 (2016).
Hoffken et al., Crystal structure and enzyme kinetics of the (S)-specific 1-phenylethanol dehydrogenase of the denitrifying bacterium strain EbN1. Biochemistry 45, 82-93 (2006).
International Search Report and Written Opinion for PCT/US18/43491 dated Dec. 16, 2019, 9 pages.
International Preliminary Report on Patentability for PCT/US18/43491 dated Jan. 28, 2020, 6 pages.
Jia et al., Materials-based strategies for multi-enzyme immobilization and co-localization: A review. Biotechnol Bioeng 111, 209-222 (2014).
Jia et al., The biology and functions of Th22 cells. Adv Exp Med Biol 841, 209-230 (2014).
Karim et al., A cell-free framework for rapid biosynthetic pathway prototyping and enzyme discovery. Metab Eng 36, 116-126 (2016).
Kim et al., Synthetic scaffold based on a cohesin-dockerin interaction for improved production of 2,3-butanediol in Saccharomyces cerevisiae. J Biotechnol 192 Pt A, 192-196 (2014).
Kinney et al., Elucidating essential role of conserved carboxysomal protein CcmN reveals common feature of bacterial microcompartment assembly. J Biol Chem 287, 17729-17736 (2012).
Kuchler et al., Enzymatic reactions in confined environments. Nat Nanotechnol 11, 409-420 (2016).
Kumar et al., MEGA7: Molecular Evolutionary Genetics Analysis Version 7.0 for Bigger Datasets. Mol Biol Evol 33, 1870-1874 (2016).
Lawrence et al., Solution structure of a bacterial microcompartment targeting peptide and its application in the construction of an ethanol bioreactor. ACS Synth Biol 3, 454-465 (2014).
Lee et al., Expression-level optimization of a multi-enzyme pathway in the absence of a high-throughput assay. Nucleic Acids Res 41, 10668-10678 (2013).
Letunic et al., Interactive tree of life (iTOL) v3: an online tool for the display and annotation of phylogenetic and other trees. Nucleic Acids Res 44, W242-245 (2016).
Li et al., Structural analysis and optimization of the covalent association between SpyCatcher and a peptide Tag. J Mol Biol 426, 309-317 (2014).
Lin, et al., "Design and Analysis of Enhanced Catalysis in Scaffolded Multienzyme Cascade Reactions". ACS Catalysis, 2014. 4(2): p. 505-511.
Lopez-Gallego et al., Multi-enzymatic synthesis. Curr Opin Chem Biol 14, 174-183 (2010).
Morgado et al., Synthetic Biology for Cell-Free Biosynthesis: Fundamentals of Designing Novel In Vitro Multi-Enzyme Reaction Networks. Adv Biochem Eng Biotechnol 162, 117-146 (2018).
Muschiol et al., Cascade catalysis—strategies and challenges en route to preparative synthetic biology. Chem Commun (Camb) 51, 5798-5811 (2015).
Mutti et al., Conversion of alcohols to enantiopure amines through dual-enzyme hydrogen-borrowing cascades. Science 349, 1525-1529 (2015).
Notredame et al., T-Coffee: A novel method for fast and accurate multiple sequence alignment. J Mol Biol 302, 205-217 (2000).
Pardee et al., Portable, On-Demand Biomolecular Manufacturing. Cell 167, 248-259 e212 (2016).
Pitts et al., Structural insight into the Clostridium difficile ethanolamine utilisation microcompartment. PLoS One 7, e48360 (2012).
Polka et al., Building Spatial Synthetic Biology with Compartments, Scaffolds, and Communities. Cold Spring Harb Perspet Biol 8, (2016).
Proschel et al., Engineering of Metabolic Pathways by Artificial Enzyme Channels. Front Bioeng Biotechnol 3, 168 (2015).
Quin et al., Encapsulation of multiple cargo proteins within recombinant Eut nanocompartments. Appl Microbiol Biotechnol 100, 9187-9200 (2016).
Quin et al., Spatial organization of multi-enzyme biocatalytic cascades. Org Biomol Chem 15, 4260-4271 (2017).
Saitou et al., The neighbor-joining method: a new method for reconstructing phylogenetic trees. Mol Biol Evol 4, 406-425 (1987).
Samborska et al., A dodecameric CcmK2 structure suggests beta-carboxysomal shell facets have a double-layered organization. Structure 20, 1353-1362 (2012).
Schmidt-Dannert et al., A roadmap for biocatalysis—functional and spatial orchestration of enzyme cascades. Microb Biotechnol 9, 601-609 (2016).
Schoene et al., SpyTag/SpyCatcher cyclization confers resilience to boiling on a mesophilic enzyme. Angew Chem Int Ed Engl 53, 6101-6104 (2014).
Siu et al., Synthetic scaffolds for pathway enhancement. Curr Opin Biotechnol 36, 98-106 (2015).
Takenoya et al., Crystallographic insights into the pore structures and mechanisms of the EutL and EutM shell proteins of the ethanolamine-utilizing microcompartment of Escherichia coli. J Baderiol 192, 6056-6063 (2010).
Tanaka et al., Structure and mechanisms of a protein-based organelle in Escherichia coli. Science 327, 81-84 (2010).
Veggiani et al., Superglue from bacteria: unbreakable bridges for protein nanotechnology. Trends Biotechnol 32, 506-512 (2014).
Vick et al., Escherichia coli enoyl-acyl carrier protein reductase (FabI) supports efficient operation of a functional reversal of beta-oxidation cycle. Appl Environ Microbiol 81, 1406-1416 (2015).
Vick et al., Optimized compatible set of BioBrick vectors for metabolic pathway engineering, Appl Microbiol Biotechnol 92, 1275-1286 (2011).

(56) References Cited

OTHER PUBLICATIONS

Watts et al., Biosynthesis of plant-specific stilbene polyketides in metabolically engineered *Escherichia coli. BMC Biotechnol* 6, 22 (2006).
Weleeldon et al., Substrate channelling as an approach to cascade reactions. *Nat Chem* 8, 299-309 (2016).
Xue et al., Process technology for multi-enzymatic reaction systems. *Bioresour Technol* 115, 183-195 (2012).
You et al., Self-assembly of synthetic metabolons through synthetic protein scaffolds: one-step purification, co-immobilization, and substrate channeling. *ACS Synth Biol* 2, 102-110 (2013).
Zakeri et al., Peptide tag forming a rapid covalent bond to a protein, through engineering a bacterial adhesin. *Proc Natl Acad Sci U S A* 109, E690-697 (2012).
Zhang et al., Controlling macromolecular topology with genetically encoded Spy Tag-SpyCatcher chemistry. *J Am Chem Soc* 135, 13988-13997 (2013).
Zhang et al., GNA13 promotes tumor growth and angiogenesis by upregulating CXC chemokines via the NF-kappaB signaling pathway in colorectal cancer cells. *Cancer Med* 7, 5611-5620 (2018).
Dos Santos et al., "Importance of the support properties for immobilization or purification of enzymes" ChemCatChem 2015 7:2413-2432.
Carballares et al., "Immobilization of the peroxygenase from Agrocybe aegerita. The effect of immobilization pH on the features of an ionically exchanged dimeric peroxygenase" Catalysts, Apr. 2021 560(11).

\* cited by examiner

FIG. 13

Column 1:
EutM-GSPED
MSPED

| a | B | e | F |
|---|---|---|---|
| KIAQLKE | ENAQLEQ | KNQQLKE | EIAQLEY | GPGSQ
| EIQALEE | KNAALKE | ENAALEE | KIQALKY | GPGS -GFP
| A | b | E | f |

Column 2:
EutM-GSPED
MSPED

| a | b | e | f |
|---|---|---|---|
| KIAQLKE | KNAALKE | KNQQLKE | KIQALKY | GPGSQ
| EIQALEE | ENAQLEQ | ENAALEE | EIAQLEY | GPGS -GFP
| A | B | E | F |

Column 3:
EutM-GSPED
MSPED

| g | h | c | d |
|---|---|---|---|
| KIAQLKQ | KIQALKQ | ENQQLEE | ENAALEE | GPGSQ
| EIQQLEE | EIAQLEQ | KNAALKE | KNQALKQ | GPGS -GFP
| G | H | C | D |

Column 4:
EutM-GSPED
MSPED

| g | H | c | D |
|---|---|---|---|
| KIAQLKQ | EIAQLEQ | ENQQLEE | KNQALKQ | GPGSQ
| EIQQLEE | KIQALKQ | KNAALKE | EENAALEE | GPGS -GFP
| G | h | C | d |

SEQUENCE LISTING

```
<160> NUMBER OF SEQ ID NOS: 115

<210> SEQ ID NO 1
<211> LENGTH: 84
<212> TYPE: PRT
<213> ORGANISM: Artificial
<220> FEATURE:
<223> OTHER INFORMATION: artificial polypeptide

<400> SEQUENCE: 1

Gly Asp Ser Ala Thr His Ile Lys Phe Ser Lys Arg Asp Glu Asp Gly
1               5                   10                  15

Lys Glu Leu Ala Gly Ala Thr Met Glu Leu Arg Asp Ser Ser Gly Lys
            20                  25                  30

Thr Ile Ser Thr Trp Ile Ser Asp Gly Gln Val Lys Asp Phe Tyr Leu
        35                  40                  45

Tyr Pro Gly Lys Tyr Thr Phe Val Glu Thr Ala Ala Pro Asp Gly Tyr
    50                  55                  60

Glu Val Ala Thr Ala Ile Thr Phe Thr Val Asn Glu Gln Gly Gln Val
65                  70                  75                  80

Thr Val Asn Gly

<210> SEQ ID NO 2
<211> LENGTH: 255
<212> TYPE: DNA
<213> ORGANISM: Artificial
<220> FEATURE:
<223> OTHER INFORMATION: artificial polynucleotide

<400> SEQUENCE: 2
ggcgatagtg ctacccatat taaattctca aaacgtgatg aggacggcaa agagttagct       60
ggtgcaacta tggagttgcg tgattcatct ggtaaaacta ttagtacatg gatttcagat      120
ggacaagtga aagatttcta cctgtatcca ggaaaatata catttgtcga aaccgcagca      180
ccagacggtt atgaggtagc aactgctatt acctttacag ttaatgagca aggtcaggtt      240
actgtaaatg gctga                                                       255

<210> SEQ ID NO 3
<211> LENGTH: 12
<212> TYPE: PRT
<213> ORGANISM: Artificial
<220> FEATURE:
<223> OTHER INFORMATION: artificial polypeptide

<400> SEQUENCE: 3

Ala His Ile Val Met Val Asp Ala Tyr Lys Pro Thr
1               5                   10

<210> SEQ ID NO 4
<211> LENGTH: 39
<212> TYPE: DNA
<213> ORGANISM: Artificial
```

```
<220> FEATURE:
<223> OTHER INFORMATION: artificial polynucleotide

<400> SEQUENCE: 4
gcccacatcg tgatggtgga cgcctacaag ccgacgaag                          39

<210> SEQ ID NO 5
<211> LENGTH: 12
<212> TYPE: PRT
<213> ORGANISM: Artificial
<220> FEATURE:
<223> OTHER INFORMATION: artificial polypeptide

<400> SEQUENCE: 5

Ala His Ile Val Met Val Asp Ala Tyr Lys Pro Thr
1               5                   10

<210> SEQ ID NO 6
<211> LENGTH: 36
<212> TYPE: DNA
<213> ORGANISM: Artificial
<220> FEATURE:
<223> OTHER INFORMATION: artificial polynucleotide

<400> SEQUENCE: 6
gcccacatcg tgatggtgga tgcctacaaa cctacg                             36

<210> SEQ ID NO 7
<211> LENGTH: 720
<212> TYPE: DNA
<213> ORGANISM: Aequorea victoria

<400> SEQUENCE: 7
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggcac   420 aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720

<210> SEQ ID NO 8
<211> LENGTH: 239
<212> TYPE: PRT
<213> ORGANISM: Aequorea victoria

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
```

```
            35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 711
<212> TYPE: DNA
<213> ORGANISM: Anaplasma marginele

<400> SEQUENCE: 9
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tccctccga cggccccgta      420 atgcagaaga gaccatgggc tgggaggcc tcctccgagc ggatgtaccc cgaggacggc      480
gccctgaagg gcgagatcaa gcagaggctg aagctgaagg acggcggcca ctacgacgct     540
gaggtcaaga ccacctacaa ggccaagaag ccgtgcagc tgcccggcgc ctacaacgtc      600
aacatcaagt ggacatcac ctcccacaac gaggactaca ccatcgtgga acagtacgaa      660
cgcgccgagg gccgccactc caccggcggc atggacgagc tgtacaagta a              711

<210> SEQ ID NO 10
<211> LENGTH: 271
<212> TYPE: PRT
<213> ORGANISM: Anaplasma marginele

<400> SEQUENCE: 10

Met Val Ser Lys Gly Glu Glu Asp Asn Met Ala Ile Ile Lys Glu Phe
```

```
              1               5                  10                 15
            Met Arg Phe Lys Val His Met Glu Gly Ser Val Asn Gly His Glu Phe
                           20                 25                 30
            Glu Ile Glu Gly Glu Gly Gly Arg Pro Tyr Glu Gly Thr Gln Thr
                           35                 40                 45
            Ala Lys Leu Lys Val Thr Lys Gly Gly Pro Leu Pro Phe Ala Trp Asp
             50                 55                 60
            Ile Leu Ser Pro Gln Phe Met Tyr Gly Ser Lys Ala Tyr Val Lys His
             65                 70                 75                 80
            Pro Ala Asp Ile Pro Asp Tyr Leu Lys Leu Ser Phe Pro Glu Gly Phe
                           85                 90                 95
            Lys Trp Glu Arg Val Met Asn Phe Glu Asp Gly Gly Val Val Thr Val
                          100                105                110
            Thr Gln Asp Ser Ser Leu Gln Asp Gly Glu Phe Ile Tyr Lys Val Lys
                          115                120                125
            Leu Arg Gly Thr Asn Phe Pro Ser Asp Gly Pro Val Met Gln Lys Lys
                          130                135                140
            Thr Met Gly Trp Glu Ala Ser Ser Glu Arg Met Tyr Pro Glu Asp Gly
            145                150                155                160
            Ala Leu Lys Gly Glu Ile Lys Gln Arg Leu Lys Leu Lys Asp Gly Gly
                          165                170                175
            His Tyr Asp Ala Glu Val Lys Thr Thr Tyr Lys Ala Lys Lys Pro Val
                          180                185                190
            Gln Leu Pro Gly Ala Tyr Asn Val Asn Ile Lys Leu Asp Ile Thr Ser
                          195                200                205
            His Asn Glu Asp Tyr Thr Ile Val Glu Gln Tyr Glu Arg Ala Glu Gly
                          210                215                220
            Arg His Ser Thr Gly Gly Met Asp Glu Leu Tyr Lys Ala Ala Ala Ser
            225                230                235                240
            Ser Ile Thr Ile Thr Ile Thr Asp Ser Pro Tyr Ala Ser Val Arg Tyr
                          245                250                255
            Phe Thr Pro His Val Leu Val Asn Phe Arg Thr Cys Ser Leu Val
                          260                265                270

<210> SEQ ID NO 11
<211> LENGTH: 141
<212> TYPE: DNA
<213> ORGANISM: Artificial
<220> FEATURE:
<223> OTHER INFORMATION: artificial polynucleotide

<400> SEQUENCE: 11
atgggcagca gccatcatca tcatcatcac agcagcggcc tggtgccgcg cggcagccat      60
atgatgggca gcagcggcgc ccacatcgtg atggtggacg cctacaagcc gacgaaggt     120 tcagggggat ccggtgtcga c                                              141

<210> SEQ ID NO 12
<211> LENGTH: 48
<212> TYPE: PRT
<213> ORGANISM: Artificial
<220> FEATURE:
<223> OTHER INFORMATION: artificial polypeptide

<400> SEQUENCE: 12

Met Gly Ser Ser His His His His His Ser Ser Gly Leu Val Pro
            1               5                  10                 15
```

Arg Gly Ser His Met Met Met Gly Ser Ser Gly Ala His Ile Val Met
            20                  25                  30

Val Asp Ala Tyr Lys Pro Thr Lys Gly Ser Gly Ser Gly Val Asp
        35                  40                  45

<210> SEQ ID NO 13
<211> LENGTH: 130
<212> TYPE: DNA
<213> ORGANISM: Artificial
<220> FEATURE:
<223> OTHER INFORMATION: artificial polynucleotide
<220> FEATURE:
<221> NAME/KEY: misc_feature
<222> LOCATION: (64)..(64)
<223> OTHER INFORMATION: encodes reporter polypeptide

<400> SEQUENCE: 13
atgggcagca gccatcatca tcatcatcac agcagcggcc tggtgccgcg cggcagccat      60
atgngtcgac tccggatcag gatccggcgg cgcccacatc gtgatggtgg atgcctacaa     120
acctacgtaa                                                            130

<210> SEQ ID NO 14
<211> LENGTH: 43
<212> TYPE: PRT
<213> ORGANISM: Artificial
<220> FEATURE:
<223> OTHER INFORMATION: artificial polypeptide
<220> FEATURE:
<221> NAME/KEY: MISC_FEATURE
<222> LOCATION: (22)..(22)
<223> OTHER INFORMATION: reporter polypeptide

<400> SEQUENCE: 14

Met Gly Ser Ser His His His His His His Ser Ser Gly Leu Val Pro
1               5                   10                  15

Arg Gly Ser His Met Xaa Val Asp Ser Gly Ser Gly Ser Gly Gly Ala
            20                  25                  30

His Ile Val Met Val Asp Ala Tyr Lys Pro Thr
        35                  40

<210> SEQ ID NO 15
<211> LENGTH: 291
<212> TYPE: DNA
<213> ORGANISM: Artificial
<220> FEATURE:
<223> OTHER INFORMATION: artificial polynucleotide

<400> SEQUENCE: 15
atggaagcat taggaatgat tgaaacccgg ggcctggttg cgctgattga ggcctccgat      60
gcgatggtaa aagccgcgcg cgtgaagctg gtcggcgtga agcagattgg cggtggcctg     120
tgtactgcca tggtgcgtgg cgatgtggcg gcgtgcaaag ccgcaaccga tgctggcgcc     180
gctgcggcgc agcgcattgg cgagttggtc tccgtacacg tgattccacg cccgcacggc     240
gatctggaag aagtgttccc gatcagcttc aaaggcgaca gcaacatttg a              291

<210> SEQ ID NO 16
<211> LENGTH: 96
<212> TYPE: PRT
<213> ORGANISM: Artificial
<220> FEATURE:
<223> OTHER INFORMATION: artificial polypeptide

<400> SEQUENCE: 16

Met Glu Ala Leu Gly Met Ile Glu Thr Arg Gly Leu Val Ala Leu Ile
1               5                   10                  15

Glu Ala Ser Asp Ala Met Val Lys Ala Ala Arg Val Lys Leu Val Gly
                20                  25                  30

Val Lys Gln Ile Gly Gly Gly Leu Cys Thr Ala Met Val Arg Gly Asp
            35                  40                  45

Val Ala Ala Cys Lys Ala Ala Thr Asp Ala Gly Ala Ala Ala Ala Gln
        50                  55                  60

Arg Ile Gly Glu Leu Val Ser Val His Val Ile Pro Arg Pro His Gly
65                  70                  75                  80

Asp Leu Glu Glu Val Phe Pro Ile Ser Phe Lys Gly Asp Ser Asn Ile
                85                  90                  95

<210> SEQ ID NO 17
<211> LENGTH: 567
<212> TYPE: DNA
<213> ORGANISM: Artificial
<220> FEATURE:
<223> OTHER INFORMATION: artificial polynucleotide

<400> SEQUENCE: 17

| | | | | | |
|---|---|---|---|---|---|
| atggaagcat | taggaatgat | tgaaacccgg | ggcctggttg | cgctgattga | ggcctccgat | 60 |
| gcgatggtaa | agccgcgcg | cgtgaagctg | gtcggcgtga | agcagattgg | cggtggcctg | 120 |
| tgtactgcca | tggtgcgtgg | cgatgtggcg | cgtgcaaag | ccgcaaccga | tgctggcgcc | 180 |
| gctgcggcgc | agcgcattgg | cgagttggtc | tccgtacacg | tgattccacg | cccgcacggc | 240 |
| gatctggaag | aagtgttccc | gatcagcttc | aaaggcgaca | gcaacattgt | cgacgggagt | 300 |
| ggtggcagcg | gaggcgatag | tgctacccat | attaaattct | caaaacgtga | tgaggacggc | 360 |
| aaagagttag | ctggtgcaac | tatggagttg | cgtgattcat | ctggtaaaac | tattagtaca | 420 |
| tggatttcag | atggacaagt | gaaagatttc | tacctgtatc | aggaaaata | tacatttgtc | 480 |
| gaaaccgcag | caccagacgg | ttatgaggta | gcaactgcta | ttaccttttac | agttaatgag | 540 |
| caaggtcagg | ttactgtaaa | tggctga | | | | 567 |

<210> SEQ ID NO 18
<211> LENGTH: 188
<212> TYPE: PRT
<213> ORGANISM: Artificial
<220> FEATURE:
<223> OTHER INFORMATION: artificial polypeptide

<400> SEQUENCE: 18

Met Glu Ala Leu Gly Met Ile Glu Thr Arg Gly Leu Val Ala Leu Ile
1               5                   10                  15

Glu Ala Ser Asp Ala Met Val Lys Ala Ala Arg Val Lys Leu Val Gly
                20                  25                  30

Val Lys Gln Ile Gly Gly Gly Leu Cys Thr Ala Met Val Arg Gly Asp
            35                  40                  45

Val Ala Ala Cys Lys Ala Ala Thr Asp Ala Gly Ala Ala Ala Ala Gln
        50                  55                  60

Arg Ile Gly Glu Leu Val Ser Val His Val Ile Pro Arg Pro His Gly
65                  70                  75                  80

Asp Leu Glu Glu Val Phe Pro Ile Ser Phe Lys Gly Asp Ser Asn Ile
                85                  90                  95

Val Asp Gly Ser Gly Gly Ser Gly Gly Asp Ser Ala Thr His Ile Lys
                100                 105                 110

```
Phe Ser Lys Arg Asp Glu Asp Gly Lys Glu Leu Ala Gly Ala Thr Met
            115                 120                 125

Glu Leu Arg Asp Ser Ser Gly Lys Thr Ile Ser Thr Trp Ile Ser Asp
        130                 135                 140

Gly Gln Val Lys Asp Phe Tyr Leu Tyr Pro Gly Lys Tyr Thr Phe Val
145                 150                 155                 160

Glu Thr Ala Ala Pro Asp Gly Tyr Glu Val Ala Thr Ala Ile Thr Phe
                165                 170                 175

Thr Val Asn Glu Gln Gly Gln Val Thr Val Asn Gly
            180                 185

<210> SEQ ID NO 19
<211> LENGTH: 58
<212> TYPE: DNA
<213> ORGANISM: Artificial
<220> FEATURE:
<223> OTHER INFORMATION: artificial polynucleotide
<220> FEATURE:
<221> NAME/KEY: misc_feature
<222> LOCATION: (58)..(58)
<223> OTHER INFORMATION: encodes EutM polypeptide

<400> SEQUENCE: 19
atgcatcatc atcaccacca cggttctggt tctggttctg gttctggttc tggttctn        58

<210> SEQ ID NO 20
<211> LENGTH: 20
<212> TYPE: PRT
<213> ORGANISM: Artificial
<220> FEATURE:
<223> OTHER INFORMATION: artificial polypeptide
<220> FEATURE:
<221> NAME/KEY: MISC_FEATURE
<222> LOCATION: (19)..(19)
<223> OTHER INFORMATION: EutM polypeptide
<220> FEATURE:
<221> NAME/KEY: misc_feature
<222> LOCATION: (20)..(20)
<223> OTHER INFORMATION: Xaa can be any naturally occurring amino acid

<400> SEQUENCE: 20

Met His His His His His His Gly Ser Gly Ser Gly Ser Gly Ser Gly
1               5                   10                  15

Ser Gly Ser Xaa
            20

<210> SEQ ID NO 21
<211> LENGTH: 750
<212> TYPE: DNA
<213> ORGANISM: Aromatoleum aromaticum

<400> SEQUENCE: 21
atgacacaaa gactgaaaga taaacttgcc gtcattacag gcggagctaa tggaattgga        60
cgcgctatag cggaaagatt tgctgtagaa ggcgctgata tcgctatcgc agaccttgta       120
ccggcccctg aggcggaggc agccatccgc aatcttggcc ggcgtgtttt aacagtgaaa       180
tgtgatgtta gccagccagg ggacgtcgaa gcgttcggga acaggttat ctcgacgttc        240 gggagatgtg atattcttgt caacaatgcg ggtatatatc ctttgattcc gtttgacgag       300
cttacattcg agcaatggaa gaaaacattt gagatcaatg tcgatagcgg gttcttgatg       360
gctaaagcct ttgtaccagg aatgaagcg aatggctggg ggcgtatcat taacttaacg       420
agcactacct attggcttaa aatagaagcg tatacccatt atataagtac gaaggcggca       480
```

```
aacattggat ttacccgcgc ccttgcctcc gacctgggca agatggtat aaccgtgaat      540 gccatagccc cctcgttggt tagaacggcg actactgaag catctgcact gagcgcaatg      600
tttgacgtgt tacccaatat gttacaggct atcccacgtc tgcaagtccc acttgatctg      660
acaggagcgg ctgcttttt ggcatccgat gacgcttcgt tcattacagg acaaacccttt     720 gcagtagacg gtgggatggt ccgtcattaa                                       750
```

<210> SEQ ID NO 22
<211> LENGTH: 249
<212> TYPE: PRT
<213> ORGANISM: Aromatoleum aromaticum

<400> SEQUENCE: 22

```
Met Thr Gln Arg Leu Lys Asp Lys Leu Ala Val Ile Thr Gly Gly Ala
1               5                   10                  15

Asn Gly Ile Gly Arg Ala Ile Ala Glu Arg Phe Ala Val Glu Gly Ala
            20                  25                  30

Asp Ile Ala Ile Ala Asp Leu Val Pro Ala Pro Glu Ala Glu Ala Ala
        35                  40                  45

Ile Arg Asn Leu Gly Arg Arg Val Leu Thr Val Lys Cys Asp Val Ser
    50                  55                  60

Gln Pro Gly Asp Val Glu Ala Phe Gly Lys Gln Val Ile Ser Thr Phe
65                  70                  75                  80

Gly Arg Cys Asp Ile Leu Val Asn Asn Ala Gly Ile Tyr Pro Leu Ile
                85                  90                  95

Pro Phe Asp Glu Leu Thr Phe Glu Gln Trp Lys Lys Thr Phe Glu Ile
            100                 105                 110

Asn Val Asp Ser Gly Phe Leu Met Ala Lys Ala Phe Val Pro Gly Met
        115                 120                 125

Lys Arg Asn Gly Trp Gly Arg Ile Ile Asn Leu Thr Ser Thr Thr Tyr
    130                 135                 140

Trp Leu Lys Ile Glu Ala Tyr Thr His Tyr Ile Ser Thr Lys Ala Ala
145                 150                 155                 160

Asn Ile Gly Phe Thr Arg Ala Leu Ala Ser Asp Leu Gly Lys Asp Gly
                165                 170                 175

Ile Thr Val Asn Ala Ile Ala Pro Ser Leu Val Arg Thr Ala Thr Thr
            180                 185                 190

Glu Ala Ser Ala Leu Ser Ala Met Phe Asp Val Leu Pro Asn Met Leu
        195                 200                 205

Gln Ala Ile Pro Arg Leu Gln Val Pro Leu Asp Leu Thr Gly Ala Ala
    210                 215                 220

Ala Phe Leu Ala Ser Asp Asp Ala Ser Phe Ile Thr Gly Gln Thr Leu
225                 230                 235                 240

Ala Val Asp Gly Gly Met Val Arg His
                245
```

<210> SEQ ID NO 23
<211> LENGTH: 891
<212> TYPE: DNA
<213> ORGANISM: Artificial
<220> FEATURE:
<223> OTHER INFORMATION: artificial polynucleotide

<400> SEQUENCE: 23

```
atgggcagca gccatcatca tcatcatcac agcagcggcc tggtgccgcg cggcagccat      60
atgatgggca gcagcggcgc ccacatcgtg atggtggacg cctacaagcc gacgaagggt     120
```

```
tcaggggat   ccggtgtcga   catgacacaa   agactgaaag   ataaacttgc   cgtcattaca      180
ggcggagcta   atggaattgg   acgcgctata   gcggaaagat   ttgctgtaga   aggcgctgat      240
atcgctatcg   cagaccttgt   accggcccct   gaggcggagg   cagccatccg   caatcttggc      300
cggcgtgttt   taacagtgaa   atgtgatgtt   agccagccag   gggacgtcga   agcgttcggg      360
aaacaggtta   tctcgacgtt   cgggagatgt   gatattcttg   tcaacaatgc   gggtatatat      420
cctttgattc   cgtttgacga   gcttacattc   gagcaatgga   agaaaacatt   tgagatcaat      480
gtcgatagcg   ggttcttgat   ggctaaagcc   tttgtaccag   gaatgaagcg   caatggctgg      540
gggcgtatca   ttaacttaac   gagcactacc   tattggctta   aaatagaagc   gtataccat       600 tatataagta   cgaaggcggc   aaacattgga   tttacccgcg   cccttgcctc   cgacctgggc      660
aaagatggta   taaccgtgaa   tgccatagcc   cctcgttgg    ttagaacggc   gactactgaa      720
gcatctgcac   tgagcgcaat   gtttgacgtg   ttacccaata   tgttacaggc   tatcccacgt      780
ctgcaagtcc   cacttgatct   gacaggagcg   gctgctttt    tggcatccga   tgacgcttcg      840
ttcattacag   gacaaaccct   tgcagtagac   ggtgggatgg   tccgtcatta   a                891
```

<210> SEQ ID NO 24
<211> LENGTH: 296
<212> TYPE: PRT
<213> ORGANISM: Artificial
<220> FEATURE:
<223> OTHER INFORMATION: artificial polypeptide

<400> SEQUENCE: 24

```
Met Gly Ser Ser His His His His His Ser Gly Leu Val Pro
 1               5                  10                  15

Arg Gly Ser His Met Met Gly Ser Ser Gly Ala His Ile Val Met Val
            20                  25                  30

Asp Ala Tyr Lys Pro Thr Lys Gly Ser Gly Gly Ser Gly Val Asp Met
        35                  40                  45

Thr Gln Arg Leu Lys Asp Lys Leu Ala Val Ile Thr Gly Gly Ala Asn
    50                  55                  60

Gly Ile Gly Arg Ala Ile Ala Glu Arg Phe Ala Val Glu Gly Ala Asp
65                  70                  75                  80

Ile Ala Ile Ala Asp Leu Val Pro Ala Pro Glu Ala Glu Ala Ala Ile
                85                  90                  95

Arg Asn Leu Gly Arg Arg Val Leu Thr Val Lys Cys Asp Val Ser Gln
            100                 105                 110

Pro Gly Asp Val Glu Ala Phe Gly Lys Gln Val Ile Ser Thr Phe Gly
        115                 120                 125

Arg Cys Asp Ile Leu Val Asn Asn Ala Gly Ile Tyr Pro Leu Ile Pro
    130                 135                 140

Phe Asp Glu Leu Thr Phe Glu Gln Trp Lys Lys Thr Phe Glu Ile Asn
145                 150                 155                 160

Val Asp Ser Gly Phe Leu Met Ala Lys Ala Phe Val Pro Gly Met Lys
                165                 170                 175

Arg Asn Gly Trp Gly Arg Ile Ile Asn Leu Thr Ser Thr Thr Tyr Trp
            180                 185                 190

Leu Lys Ile Glu Ala Tyr Thr His Tyr Ile Ser Thr Lys Ala Ala Asn
        195                 200                 205

Ile Gly Phe Thr Arg Ala Leu Ala Ser Asp Leu Gly Lys Asp Gly Ile
    210                 215                 220
```

```
Thr Val Asn Ala Ile Ala Pro Ser Leu Val Arg Thr Ala Thr Thr Glu
225                 230                 235                 240

Ala Ser Ala Leu Ser Ala Met Phe Asp Val Leu Pro Asn Met Leu Gln
                245                 250                 255

Ala Ile Pro Arg Leu Gln Val Pro Leu Asp Leu Thr Gly Ala Ala Ala
            260                 265                 270

Phe Leu Ala Ser Asp Asp Ala Ser Phe Ile Thr Gly Gln Thr Leu Ala
        275                 280                 285

Val Asp Gly Gly Met Val Arg His
    290                 295

<210> SEQ ID NO 25
<211> LENGTH: 876
<212> TYPE: DNA
<213> ORGANISM: Artificial
<220> FEATURE:
<223> OTHER INFORMATION: artificial polynucleotide

<400> SEQUENCE: 25
atgggcagca gccatcatca tcatcatcac agcagcggcc tggtgccgcg cggcagccat      60
atgatgacac aaagactgaa agataaactt gccgtcatta caggcggagc taatggaatt     120
ggacgcgcta tagcggaaag atttgctgta gaaggcgctg atatcgctat cgcagacctt     180
gtaccggccc ctgaggcgga ggcagccatc cgcaatcttg gccggcgtgt tttaacagtg     240
aaatgtgatg ttagccagcc aggggacgtc gaagcgttcg ggaaacaggt tatctcgacg     300 ttcggggagat gtgatattct tgtcaacaat gcgggtatat atccttttgat tccgtttgac     360 gagcttacat tcgagcaatg gaagaaaaca tttgagatca atgtcgatag cgggttcttg     420
atggctaaag cctttgtacc aggaatgaag cgcaatggct gggggcgtat cattaactta     480
acgagcacta cctattggct taaaatagaa gcgtataccc attatataag tacgaaggcg     540
gcaaacattg gatttacccg cgcccttgcc tccgacctgg gcaaagatgg tataaccgtg     600
aatgccatag ccccctcgtt ggttagaacg gcgactactg aagcatctgc actgagcgca     660
atgtttgacg tgttacccaa tatgttacag gctatcccac gtctgcaagt cccacttgat     720
ctgacaggag cggctgcttt tttggcatcc gatgacgctt cgttcattac aggacaaacc     780
cttgcagtag acggtgggat ggtccgtcat gtcgactccg gatcaggatc cggcggcgcc     840
cacatcgtga tggtggatgc ctacaaacct acgtaa                              876

<210> SEQ ID NO 26
<211> LENGTH: 291
<212> TYPE: PRT
<213> ORGANISM: Artificial
<220> FEATURE:
<223> OTHER INFORMATION: artificial polypeptide

<400> SEQUENCE: 26

Met Gly Ser Ser His His His His His His Ser Ser Gly Leu Val Pro
1               5                   10                  15

Arg Gly Ser His Met Met Thr Gln Arg Leu Lys Asp Lys Leu Ala Val
                20                  25                  30

Ile Thr Gly Gly Ala Asn Gly Ile Gly Arg Ala Ile Ala Glu Arg Phe
            35                  40                  45

Ala Val Glu Gly Ala Asp Ile Ala Ile Ala Asp Leu Val Pro Ala Pro
        50                  55                  60

Glu Ala Glu Ala Ala Ile Arg Asn Leu Gly Arg Arg Val Leu Thr Val
65                  70                  75                  80
```

```
Lys Cys Asp Val Ser Gln Pro Gly Asp Val Glu Ala Phe Gly Lys Gln
                85                  90                  95

Val Ile Ser Thr Phe Gly Arg Cys Asp Ile Leu Val Asn Asn Ala Gly
            100                 105                 110

Ile Tyr Pro Leu Ile Pro Phe Asp Glu Leu Thr Phe Glu Gln Trp Lys
        115                 120                 125

Lys Thr Phe Glu Ile Asn Val Asp Ser Gly Phe Leu Met Ala Lys Ala
    130                 135                 140

Phe Val Pro Gly Met Lys Arg Asn Gly Trp Gly Arg Ile Ile Asn Leu
145                 150                 155                 160

Thr Ser Thr Thr Tyr Trp Leu Lys Ile Glu Ala Tyr Thr His Tyr Ile
                165                 170                 175

Ser Thr Lys Ala Ala Asn Ile Gly Phe Thr Arg Ala Leu Ala Ser Asp
            180                 185                 190

Leu Gly Lys Asp Gly Ile Thr Val Asn Ala Ile Ala Pro Ser Leu Val
        195                 200                 205

Arg Thr Ala Thr Thr Glu Ala Ser Ala Leu Ser Ala Met Phe Asp Val
    210                 215                 220

Leu Pro Asn Met Leu Gln Ala Ile Pro Arg Leu Gln Val Pro Leu Asp
225                 230                 235                 240

Leu Thr Gly Ala Ala Ala Phe Leu Ala Ser Asp Ala Ser Phe Ile
                245                 250                 255

Thr Gly Gln Thr Leu Ala Val Asp Gly Gly Met Val Arg His Val Asp
                260                 265                 270

Ser Gly Ser Gly Ser Gly Gly Ala His Ile Val Met Val Asp Ala Tyr
            275                 280                 285

Lys Pro Thr
    290

<210> SEQ ID NO 27
<211> LENGTH: 1134
<212> TYPE: DNA
<213> ORGANISM: Artificial
<220> FEATURE:
<223> OTHER INFORMATION: artificial polynucleotide

<400> SEQUENCE: 27
atgtcgttgg tggaaaaaac ctccattatt aaagacttca cattgttcga aaaaatgtca      60
gaacatgagc aggtagtctt ttgcaacgat cccgcgacgg gtcttcgggc tattattgcg     120
atccatgaca cgactttagg gcctgctctt ggcggttgcc gtatgcagcc gtataacagt     180
gtagaagaag ctctggaaga tgctttgcgt ttgagcaaag gaatgacgta cagctgcgcg     240
gcgtctgacg ttgacttcgg gggaggcaaa gcggtgataa tcggggatcc tcaaaaggat     300
aaaagccctg agttgtttcg tgcatttggg caatttgtag acagccttgg cggtagattt     360
tacacaggca ctgatatggg cactaacatg gaggacttta tccatgccat gaaggaaact     420
aactgcatcg tcggagtccc agaggcctat gggtctagcg gtaaccccctc cccgcgaca      480 gcatatggcg tgtatcgtgg aatgaaggct gctgccaagg aagcgttcgg atccgactcc     540
ttggaaggta aggtagtggc ggttcaaggc gtcgggaatg tcgcgtatca tctgtgtcgg     600
catctgcatg aggaaggagc caagttaata gttacggaca taaacaagga agccgtggct     660
cgcgccgtag aagaattcgg ggcaaaggcc gtcgatccta tgacacatcta tggcgtcgaa     720 tgcgacatct tcgccccatg tgccctgggt ggtataataa atgatcaaac aattccacag     780
```

```
cttaaagcaa aagtgatcgc gggatctgca ttaaaccaac tgaaagagcc ccgtcacggc    840
gacatgattc acgaaatggg gatagtttat gcccctgact atgtcatcaa cgcgggagga    900
tgtatcaatg tagcggatga acttatgga tacaatcgtg aacgcgcaat gaaaaagatc     960
gagcaaatct atgacaatat agaaaaagtc ttcgcaatcg caaaacgtga taatataccc   1020
acttatgtcg ccgccgatcg tatggctgag gaacggatag agactatgcg taaggcacgg   1080
agtcaatttc ttcagaacgg gcatcatatt ttgagccgca aagagcgag ataa           1134
```

<210> SEQ ID NO 28
<211> LENGTH: 377
<212> TYPE: PRT
<213> ORGANISM: Artificial
<220> FEATURE:
<223> OTHER INFORMATION: artificial polypeptide

<400> SEQUENCE: 28

```
Met Ser Leu Val Glu Lys Thr Ser Ile Ile Lys Asp Phe Thr Leu Phe
1               5                   10                  15

Glu Lys Met Ser Glu His Glu Gln Val Val Phe Cys Asn Asp Pro Ala
            20                  25                  30

Thr Gly Leu Arg Ala Ile Ile Ala Ile His Asp Thr Thr Leu Gly Pro
        35                  40                  45

Ala Leu Gly Gly Cys Arg Met Gln Pro Tyr Asn Ser Val Glu Glu Ala
    50                  55                  60

Leu Glu Asp Ala Leu Arg Leu Ser Lys Gly Met Thr Tyr Ser Cys Ala
65                  70                  75                  80

Ala Ser Asp Val Asp Phe Gly Gly Gly Lys Ala Val Ile Ile Gly Asp
                85                  90                  95

Pro Gln Lys Asp Lys Ser Pro Glu Leu Phe Arg Ala Phe Gly Gln Phe
            100                 105                 110

Val Asp Ser Leu Gly Gly Arg Phe Tyr Thr Gly Thr Asp Met Gly Thr
        115                 120                 125

Asn Met Glu Asp Phe Ile His Ala Met Lys Glu Thr Asn Cys Ile Val
130                 135                 140

Gly Val Pro Glu Ala Tyr Gly Ser Ser Gly Asn Pro Ser Pro Ala Thr
145                 150                 155                 160

Ala Tyr Gly Val Tyr Arg Gly Met Lys Ala Ala Ala Lys Glu Ala Phe
                165                 170                 175

Gly Ser Asp Ser Leu Glu Gly Lys Val Val Ala Val Gln Gly Val Gly
            180                 185                 190

Asn Val Ala Tyr His Leu Cys Arg His Leu His Glu Glu Gly Ala Lys
        195                 200                 205

Leu Ile Val Thr Asp Ile Asn Lys Glu Ala Val Ala Arg Ala Val Glu
    210                 215                 220

Glu Phe Gly Ala Lys Ala Val Asp Pro Asn Asp Ile Tyr Gly Val Glu
225                 230                 235                 240

Cys Asp Ile Phe Ala Pro Cys Ala Leu Gly Gly Ile Ile Asn Asp Gln
                245                 250                 255

Thr Ile Pro Gln Leu Lys Ala Lys Val Ile Ala Gly Ser Ala Leu Asn
            260                 265                 270

Gln Leu Lys Glu Pro Arg His Gly Asp Met Ile His Glu Met Gly Ile
        275                 280                 285

Val Tyr Ala Pro Asp Tyr Val Ile Asn Ala Gly Gly Cys Ile Asn Val
    290                 295                 300
```

Ala Asp Glu Leu Tyr Gly Tyr Asn Arg Glu Arg Ala Met Lys Lys Ile
305                 310                 315                 320

Glu Gln Ile Tyr Asp Asn Ile Glu Lys Val Phe Ala Ile Ala Lys Arg
            325                 330                 335

Asp Asn Ile Pro Thr Tyr Val Ala Ala Asp Arg Met Ala Glu Glu Arg
        340                 345                 350

Ile Glu Thr Met Arg Lys Ala Arg Ser Gln Phe Leu Gln Asn Gly His
        355                 360                 365

His Ile Leu Ser Arg Arg Arg Ala Arg
        370                 375

<210> SEQ ID NO 29
<211> LENGTH: 1275
<212> TYPE: DNA
<213> ORGANISM: Artificial
<220> FEATURE:
<223> OTHER INFORMATION: artificial polynucleotide

<400> SEQUENCE: 29

| | | |
|---|---|---|
| atgggcagca gccatcatca tcatcatcac agcagcggcc tggtgccgcg cggcagccat | 60 |
| atgatgggca gcagcggcgc ccacatcgtg atggtggacg cctacaagcc gacgaagggt | 120 |
| tcaggggggat ccggtgtcga catgtcgttg gtggaaaaaa cctccattat taaagacttc | 180 |
| acattgttcg aaaaaatgtc agaacatgag caggtagtct tttgcaacga tcccgcgacg | 240 |
| ggtcttcggg ctattattgc gatccatgac acgactttag gcctgctctt ggcggttgc | 300 |
| cgtatgcagc cgtataacag tgtagaagaa gctctggaag atgctttgcg tttgagcaaa | 360 |
| ggaatgacgt acagctgcgc ggcgtctgac gttgacttcg ggggaggcaa agcggtgata | 420 |
| atcggggatc ctcaaaagga taaaagccct gagttgtttc gtgcatttgg caatttgta | 480 |
| gacagccttg gcggtagatt ttacacaggc actgatatgg gcactaacat ggaggacttt | 540 |
| atccatgcca tgaaggaaac taactgcatc gtcggagtcc cagaggccta tgggtctagc | 600 |
| ggtaacccct cccccgcgac agcatatggc gtgtatcgtg aatgaaggc tgctgccaag | 660 |
| gaagcgttcg gatccgactc cttggaaggt aaggtagtgg cggttcaagg cgtcgggaat | 720 |
| gtcgcgtatc atctgtgtcg gcatctgcat gaggaaggag ccaagttaat agttacggac | 780 |
| ataaacaagg aagccgtggc tcgcgccgta gaagaattcg gggcaaaggc cgtcgatcct | 840 |
| aatgacatct atggcgtcga atgcgacatc ttcgccccat gtgccctggg tggtataata | 900 |
| aatgatcaaa caattccaca gcttaaagca aaagtgatcg cgggatctgc attaaaccaa | 960 |
| ctgaaagagc cccgtcacgg cgacatgatt cacgaaatgg ggatagttta tgcccctgac | 1020 |
| tatgtcatca cgcgggagg atgtatcaat gtagcggatg aactttatgg atacaatcgt | 1080 |
| gaacgcgcaa tgaaaaagat cgagcaaatc tatgacaata tagaaaaagt cttcgcaatc | 1140 |
| gcaaaacgtg ataatatacc cacttatgtc gccgccgatc gtatggctga ggaacggata | 1200 |
| gagactatgc gtaaggcacg gagtcaattt cttcagaacg gcatcatat tttgagccgc | 1260 |
| agaagagcga gataa | 1275 |

<210> SEQ ID NO 30
<211> LENGTH: 424
<212> TYPE: PRT
<213> ORGANISM: Artificial
<220> FEATURE:
<223> OTHER INFORMATION: artificial polypeptide

<400> SEQUENCE: 30

```
Met Gly Ser Ser His His His His His Ser Ser Gly Leu Val Pro
1               5                   10                  15

Arg Gly Ser His Met Met Gly Ser Ser Gly Ala His Ile Val Met Val
                20              25                  30

Asp Ala Tyr Lys Pro Thr Lys Gly Ser Gly Gly Ser Gly Val Asp Met
            35              40                  45

Ser Leu Val Glu Lys Thr Ser Ile Ile Lys Asp Phe Thr Leu Phe Glu
50              55                  60

Lys Met Ser Glu His Glu Gln Val Val Phe Cys Asn Asp Pro Ala Thr
65              70                  75                  80

Gly Leu Arg Ala Ile Ile Ala Ile His Asp Thr Thr Leu Gly Pro Ala
                85                  90                  95

Leu Gly Gly Cys Arg Met Gln Pro Tyr Asn Ser Val Glu Glu Ala Leu
                100                 105                 110

Glu Asp Ala Leu Arg Leu Ser Lys Gly Met Thr Tyr Ser Cys Ala Ala
            115                 120                 125

Ser Asp Val Asp Phe Gly Gly Lys Ala Val Ile Ile Gly Asp Pro
            130                 135                 140

Gln Lys Asp Lys Ser Pro Glu Leu Phe Arg Ala Phe Gly Gln Phe Val
145                 150                 155                 160

Asp Ser Leu Gly Gly Arg Phe Tyr Thr Gly Thr Asp Met Gly Thr Asn
                165                 170                 175

Met Glu Asp Phe Ile His Ala Met Lys Glu Thr Asn Cys Ile Val Gly
            180                 185                 190

Val Pro Glu Ala Tyr Gly Ser Ser Gly Asn Pro Ser Pro Ala Thr Ala
        195                 200                 205

Tyr Gly Val Tyr Arg Gly Met Lys Ala Ala Ala Lys Glu Ala Phe Gly
    210                 215                 220

Ser Asp Ser Leu Glu Gly Lys Val Val Ala Val Gln Gly Val Gly Asn
225                 230                 235                 240

Val Ala Tyr His Leu Cys Arg His Leu His Glu Glu Gly Ala Lys Leu
                245                 250                 255

Ile Val Thr Asp Ile Asn Lys Glu Ala Val Ala Arg Ala Val Glu Glu
            260                 265                 270

Phe Gly Ala Lys Ala Val Asp Pro Asn Asp Ile Tyr Gly Val Glu Cys
    275                 280                 285

Asp Ile Phe Ala Pro Cys Ala Leu Gly Gly Ile Ile Asn Asp Gln Thr
            290                 295                 300

Ile Pro Gln Leu Lys Ala Lys Val Ile Ala Gly Ser Ala Leu Asn Gln
305                 310                 315                 320

Leu Lys Glu Pro Arg His Gly Asp Met Ile His Glu Met Gly Ile Val
                325                 330                 335

Tyr Ala Pro Asp Tyr Val Ile Asn Ala Gly Gly Cys Ile Asn Val Ala
            340                 345                 350

Asp Glu Leu Tyr Gly Tyr Asn Arg Glu Arg Ala Met Lys Lys Ile Glu
            355                 360                 365

Gln Ile Tyr Asp Asn Ile Glu Lys Val Phe Ala Ile Ala Lys Arg Asp
    370                 375                 380

Asn Ile Pro Thr Tyr Val Ala Ala Asp Arg Met Ala Glu Glu Arg Ile
385                 390                 395                 400

Glu Thr Met Arg Lys Ala Arg Ser Gln Phe Leu Gln Asn Gly His His
            405                 410                 415

Ile Leu Ser Arg Arg Arg Ala Arg
```

<210> SEQ ID NO 31
<211> LENGTH: 1260
<212> TYPE: DNA
<213> ORGANISM: Artificial
<220> FEATURE:
<223> OTHER INFORMATION: artificial polynucleotide

<400> SEQUENCE: 31

```
atgggcagca gccatcatca tcatcatcac agcagcggcc tggtgccgcg cggcagccat      60
atgatgtcgt tggtggaaaa aacctccatt attaaagact tcacattgtt cgaaaaaatg     120
tcagaacatg agcaggtagt cttttgcaac gatcccgcga cgggtcttcg ggctattatt     180
gcgatccatg acacgacttt agggcctgct cttggcggtt gccgtatgca gccgtataac     240
agtgtagaag aagctctgga agatgctttg cgtttgagca aggaatgac  gtacagctgc     300
gcggcgtctg acgttgactt cggggaggc  aaagcggtga taatcgggga tcctcaaaag     360
gataaaagcc ctgagttgtt tcgtgcattt gggcaatttg tagacagcct ggcggtaga      420
ttttacacag gcactgatat gggcactaac atggaggact ttatccatgc catgaaggaa     480
actaactgca tcgtcggagt cccagaggcc tatgggtcta gcggtaaccc ctcccccgcg     540
acagcatatg gcgtgtatcg tggaatgaag gctgctgcca aggaagcgtt cggatccgac     600
tccttggaag gtaaggtagt ggcggttcaa ggcgtcggga tgtcgcgta  tcatctgtgt     660
cggcatctgc atgaggaagg agccaagtta atagttacgg acataaacaa ggaagccgtg     720
gctcgcgccg tagaagaatt cggggcaaag gccgtcgatc ctaatgacat ctatggcgtc     780
gaatgcgaca tcttcgcccc atgtgccctg ggtggtataa taaatgatca aacaattcca     840
cagcttaaag caaaagtgat cgcgggatct gcattaaacc aactgaaaga gccccgtcac     900
ggcgacatga ttcacgaaat ggggatagtt tatgcccctg actatgtcat caacgcggga     960
ggatgtatca atgtagcgga tgaactttat ggatacaatc gtgaacgcgc aatgaaaaag    1020
atcgagcaaa tctatgacaa tatagaaaaa gtcttcgcaa tcgcaaaacg tgataatata    1080
cccacttatg tcgccgccga tcgtatggct gaggaacgga tagagactat gcgtaaggca    1140
cggagtcaat ttcttcagaa cgggcatcat attttgagcc gcagaagagc gagagtcgac    1200
tccggatcag gatccggcgg cgcccacatc gtgatggtgg atgcctacaa acctacgtaa    1260
```

<210> SEQ ID NO 32
<211> LENGTH: 419
<212> TYPE: PRT
<213> ORGANISM: Artificial
<220> FEATURE:
<223> OTHER INFORMATION: artificial polypeptide

<400> SEQUENCE: 32

```
Met Gly Ser Ser His His His His His His Ser Ser Gly Leu Val Pro
1               5                   10                  15

Arg Gly Ser His Met Met Ser Leu Val Glu Lys Thr Ser Ile Ile Lys
            20                  25                  30

Asp Phe Thr Leu Phe Glu Lys Met Ser Glu His Glu Gln Val Val Phe
        35                  40                  45

Cys Asn Asp Pro Ala Thr Gly Leu Arg Ala Ile Ile Ala Ile His Asp
    50                  55                  60

Thr Thr Leu Gly Pro Ala Leu Gly Gly Cys Arg Met Gln Pro Tyr Asn
65                  70                  75                  80
```

Ser Val Glu Glu Ala Leu Glu Asp Ala Leu Arg Leu Ser Lys Gly Met
            85                  90                  95

Thr Tyr Ser Cys Ala Ala Ser Asp Val Asp Phe Gly Gly Gly Lys Ala
        100                 105                 110

Val Ile Ile Gly Asp Pro Gln Lys Asp Lys Ser Pro Glu Leu Phe Arg
        115                 120                 125

Ala Phe Gly Gln Phe Val Asp Ser Leu Gly Gly Arg Phe Tyr Thr Gly
        130                 135                 140

Thr Asp Met Gly Thr Asn Met Glu Asp Phe Ile His Ala Met Lys Glu
145                 150                 155                 160

Thr Asn Cys Ile Val Gly Val Pro Glu Ala Tyr Gly Ser Ser Gly Asn
            165                 170                 175

Pro Ser Pro Ala Thr Ala Tyr Gly Val Tyr Arg Gly Met Lys Ala Ala
            180                 185                 190

Ala Lys Glu Ala Phe Gly Ser Asp Ser Leu Glu Gly Lys Val Val Ala
        195                 200                 205

Val Gln Gly Val Gly Asn Val Ala Tyr His Leu Cys Arg His Leu His
        210                 215                 220

Glu Glu Gly Ala Lys Leu Ile Val Thr Asp Ile Asn Lys Glu Ala Val
225                 230                 235                 240

Ala Arg Ala Val Glu Glu Phe Gly Ala Lys Ala Val Asp Pro Asn Asp
            245                 250                 255

Ile Tyr Gly Val Glu Cys Asp Ile Phe Ala Pro Cys Ala Leu Gly Gly
            260                 265                 270

Ile Ile Asn Asp Gln Thr Ile Pro Gln Leu Lys Ala Lys Val Ile Ala
            275                 280                 285

Gly Ser Ala Leu Asn Gln Leu Lys Glu Pro Arg His Gly Asp Met Ile
        290                 295                 300

His Glu Met Gly Ile Val Tyr Ala Pro Asp Tyr Val Ile Asn Ala Gly
305                 310                 315                 320

Gly Cys Ile Asn Val Ala Asp Glu Leu Tyr Gly Tyr Asn Arg Glu Arg
            325                 330                 335

Ala Met Lys Lys Ile Glu Gln Ile Tyr Asp Asn Ile Glu Lys Val Phe
            340                 345                 350

Ala Ile Ala Lys Arg Asp Asn Ile Pro Thr Tyr Val Ala Ala Asp Arg
        355                 360                 365

Met Ala Glu Glu Arg Ile Glu Thr Met Arg Lys Ala Arg Ser Gln Phe
370                 375                 380

Leu Gln Asn Gly His His Ile Leu Ser Arg Arg Arg Ala Arg Val Asp
385                 390                 395                 400

Ser Gly Ser Gly Ser Gly Gly Ala His Ile Val Met Val Asp Ala Tyr
            405                 410                 415

Lys Pro Thr

<210> SEQ ID NO 33
<211> LENGTH: 96
<212> TYPE: PRT
<213> ORGANISM: Salmonella enterica

<400> SEQUENCE: 33

Met Glu Ala Leu Gly Met Ile Glu Thr Arg Gly Leu Val Ala Leu Ile
1               5                   10                  15

Glu Ala Ser Asp Thr Met Val Lys Ala Ala Arg Val Lys Leu Val Gly
            20                  25                  30

```
Val Lys Gln Ile Gly Gly Gly Leu Cys Thr Ala Met Val Arg Gly Asp
            35                  40                  45

Val Ala Ala Cys Lys Ala Ala Thr Asp Ala Gly Ala Ala Ala Ala Gln
 50                  55                  60

Arg Ile Gly Glu Leu Val Ser Val His Val Ile Pro Arg Pro His Gly
 65                  70                  75                  80

Asp Leu Glu Glu Val Phe Pro Ile Ser Phe Lys Gly Asp Ser Asn Ile
                 85                  90                  95

<210> SEQ ID NO 34
<211> LENGTH: 342
<212> TYPE: DNA
<213> ORGANISM: Artificial
<220> FEATURE:
<223> OTHER INFORMATION: artificial polynucleotide

<400> SEQUENCE: 34
atgcatcatc atcaccacca cggttctggt tctggttctg gttctggttc tggttctgaa      60
gcattaggaa tgattgaaac ccggggcctg gttgcgctga ttgaggcctc cgatgcgatg     120
gtaaaagccg cgcgcgtgaa gctggtcggc gtgaagcaga ttggcggtgg cctgtgtact     180
gccatggtgc gtggcgatgt gcggcgtgc aaagccgcaa ccgatgctgg cgccgctgcg     240
gcgcagcgca ttggcgagtt ggtctccgta cacgtgattc cacgcccgca cggcgatctg     300
gaagaagtgt tcccgatcag cttcaaaggc gacagcaaca tt                       342

<210> SEQ ID NO 35
<211> LENGTH: 94
<212> TYPE: PRT
<213> ORGANISM: A. metalliredigens

<400> SEQUENCE: 35

Met Ala Ile Ser Asn Ala Leu Gly Met Ile Glu Thr Lys Gly Leu Val
 1               5                  10                  15

Gly Ala Ile Glu Ala Ala Asp Ala Met Val Lys Ala Ala Asn Val Thr
                20                  25                  30

Leu Leu Gly Lys Glu His Val Gly Gly Gly Leu Val Thr Val Met Val
            35                  40                  45

Arg Gly Asp Val Gly Ala Val Lys Ala Ala Thr Asp Ala Gly Ala Ala
 50                  55                  60

Ala Ala Glu Arg Val Gly Glu Leu Met Ser Val His Val Ile Pro Arg
 65                  70                  75                  80

Pro His Gly Glu Val Glu Thr Ile Leu Pro Gln Ile Lys Glu
                 85                  90

<210> SEQ ID NO 36
<211> LENGTH: 315
<212> TYPE: DNA
<213> ORGANISM: Artificial
<220> FEATURE:
<223> OTHER INFORMATION: artificial polynucleotide

<400> SEQUENCE: 36
atgcatcatc atcatcacca cggcagcggt agcggcagcg gtagcggcag cggtagcgca      60
ctgggtatga tcgaaaccaa gggcctggtt ggtgcgattg aagcggcgga cgcgatggtt     120
aaggcggcga acgtgaccct gctgggtaaa gagcacgtgg gtggcggtct ggtgaccgtt     180
atggtgcgtg gcgacgttgg tgcggtgaaa gcggcgaccg atgcgggtgc tgcggcggcg     240
gagcgtgttg gtgaactgat gagcgttcat gtgatcccgc gtccgcacgg cgaggtggaa     300
```
accattctgc cgtaa                                                         315

<210> SEQ ID NO 37
<211> LENGTH: 97
<212> TYPE: PRT
<213> ORGANISM: Aneurinibacillus terranovensis

<400> SEQUENCE: 37

Met Ala Arg Glu Ile Asn Gly Ala Leu Gly Met Ile Glu Thr Arg Gly
1               5                   10                  15

Leu Val Ala Ser Leu Glu Ala Ala Asp Ala Met Val Lys Ala Ala Asn
            20                  25                  30

Val Asn Ile Val Gly Lys Val His Val Gly Gly Ile Val Thr Val
        35                  40                  45

Leu Val Thr Gly Asp Val Gly Ala Val Lys Ala Ala Thr Glu Ala Gly
    50                  55                  60

Ser Thr Ala Ala Gln Arg Val Gly Glu Ile Ile Ser Val His Val Ile
65                  70                  75                  80

Pro Arg Pro His His Glu Leu Gly Ser Ile Leu Pro Lys Leu Glu Glu
                85                  90                  95

Tyr

<210> SEQ ID NO 38
<211> LENGTH: 315
<212> TYPE: DNA
<213> ORGANISM: Artificial
<220> FEATURE:
<223> OTHER INFORMATION: artificial polynucleotide

<400> SEQUENCE: 38
atgcatcatc atcatcacca cggcagcggt agcggcagcg gtagcggcag cggtagcgca     60
ctgggtatga tcgaaacccg tggtctggtg gcgagcctgg aggcggcgga tgcgatggtg    120
aaggcggcga acgttaacat cgtgggcaaa gtgcacgttg gtggcggtat tgtgaccgtt    180
ctggtgaccg gcgatgttgg tgcggtgaaa gcggcgaccg aggcgggcag caccgcggcg    240
cagcgtgttg gtgaaatcat tagcgttcat gtgatcccgc gtccgcacca tgagctgggt    300
agcattctgc cgtaa                                                     315

<210> SEQ ID NO 39
<211> LENGTH: 95
<212> TYPE: PRT
<213> ORGANISM: Caldalkalibacillus thermarum

<400> SEQUENCE: 39

Met Asn Glu Ser Leu Gly Phe Ile Glu Thr Arg Gly Phe Thr Ala Ala
1               5                   10                  15

Ile Glu Ala Ala Asp Ala Met Leu Lys Ala Ala Asn Val Glu Ile Val
            20                  25                  30

Gly Ser Glu Lys Ile Gly Ser Gly Leu Val Ser Val Ile Val Lys Gly
        35                  40                  45

Asp Val Gly Ala Val Lys Ala Ala Thr Glu Val Gly Ala Glu Ala Ala
    50                  55                  60

Gly Arg Val Gly Glu Val Ile Ala Val His Val Ile Pro Arg Pro His
65                  70                  75                  80

Gly Asp Ile Gln Lys Leu Leu Pro Thr Val Lys Asp Asp Ala Val
                85                  90                  95

<210> SEQ ID NO 40
<211> LENGTH: 318
<212> TYPE: DNA
<213> ORGANISM: Artificial
<220> FEATURE:
<223> OTHER INFORMATION: artificial polynucleotide

<400> SEQUENCE: 40

```
atgcatcatc atcatcacca cggtagcggc agcggtagcg gcagcggtag cggcagcgag      60
agcctgggtt tcatcgaaac ccgtggcttt accgcggcga ttgaagcggc ggatgcgatg     120
ctgaaggcgg cgaacgttga gatcgtgggt agcgaaaaaa ttggtagcgg cctggtgagc     180
gttatcgtga agggtgatgt tggcgcggtg aaagcggcga ccgaggttgg tgcggaagcg     240
gcgggtcgtg ttggcgaagt gatcgcggtt cacgtgattc cgcgtccgca cggcgacatt     300
cagaagctgc tgccgtaa                                                   318
```

<210> SEQ ID NO 41
<211> LENGTH: 96
<212> TYPE: PRT
<213> ORGANISM: Desulfosporosinus acidiphilus

<400> SEQUENCE: 41

Met Asn Lys Thr Glu Ala Leu Gly Leu Ile Glu Thr Lys Gly Leu Val
1               5                   10                  15

Gly Ala Ile Glu Ala Ala Asp Ala Met Val Lys Ala Ala Asn Val Tyr
            20                  25                  30

Leu Ile Gly Arg Glu Leu Val Gly Gly Leu Val Thr Val Met Val
        35                  40                  45

Arg Gly Asp Val Gly Ala Val Lys Ala Ala Thr Asp Ala Gly Ala Ala
    50                  55                  60

Ala Ala Gln Arg Val Gly Glu Leu Ile Ser Val His Val Ile Pro Arg
65                  70                  75                  80

Pro His Gly Asp Val Glu Met Ile Leu Pro Gln Ala Lys Lys Glu Ala
                85                  90                  95

<210> SEQ ID NO 42
<211> LENGTH: 330
<212> TYPE: DNA
<213> ORGANISM: Artificial
<220> FEATURE:
<223> OTHER INFORMATION: artificial polynucleotide

<400> SEQUENCE: 42

```
atgcatcatc atcatcacca cggcagcggt agcggcagcg gtagcggcag cggtagcgag      60
gcgctgggcc tgatcgaaac caagggcctg gttggtgcga ttgaggcggc ggacgcgatg     120
gttaaagcgg cgaacgtgta cctgatcggt cgtgaactgg tgggtggcgg tctggtgacc     180
gttatggttc gtggcgacgt tggtgcggtg aaagcggcga ccgatgcggg tgctgcggcg     240
gcgcagcgtg ttggcgagct gatcagcgtt cacgtgattc cgcgtccgca cggcgatgtg     300
gaaatgattc tgccgcaagc gaagaaataa                                      330
```

<210> SEQ ID NO 43
<211> LENGTH: 92
<212> TYPE: PRT
<213> ORGANISM: Desulfotalea psychrophila

<400> SEQUENCE: 43

Met Asp Ser Leu Gly Met Ile Glu Thr Lys Gly Leu Ile Ala Leu Ile

```
    1               5                  10                 15
Glu Ala Ser Asp Ala Met Val Lys Ala Ala Arg Val Gln Leu Val Gly
            20                  25                  30

Tyr Lys Gln Ile Gly Ala Gly Leu Val Thr Ala Ile Val Arg Gly Asp
            35                  40                  45

Val Ala Ala Cys Lys Ala Ala Thr Asp Ala Gly Ala Ala Ala Ala Ala
            50                  55                  60

Arg Ile Gly Glu Val Val Ala Val His Val Ile Pro Arg Pro His Gly
65                  70                  75                  80

Asp Leu Glu Glu Val Phe Pro Phe Lys Arg Asp Lys
                85                  90

<210> SEQ ID NO 44
<211> LENGTH: 333
<212> TYPE: DNA
<213> ORGANISM: Artificial
<220> FEATURE:
<223> OTHER INFORMATION: artificial polynucleotide

<400> SEQUENCE: 44
atgcatcatc atcaccacca cggttctggt tctggttctg gttctggttc tggttctgat      60
tcattaggaa tgattgaaac taagggcttg atcgcactta ttgaagcttc agatgcaatg    120
gtaaaggctg ctcgtgtaca acttgtaggt tacaaacaaa ttggtgctgg tttggtaact    180
gcgattgttc gtggtgatgt tgcagcatgt aaagcagcaa ccgatgcagg tgcagcagca    240
gccgcacgta ttggcgaggt ggtagctgta cacgttattc cacgtccaca tggtgacctg    300
gaagaagtat ttcccttcaa acgtgacaaa tag                                 333

<210> SEQ ID NO 45
<211> LENGTH: 94
<212> TYPE: PRT
<213> ORGANISM: Desulfotomaculum thermocisternum

<400> SEQUENCE: 45

Met Thr Gly Glu Ala Leu Gly Met Val Glu Thr Arg Gly Leu Val Pro
1               5                  10                  15

Ala Ile Glu Ala Ala Asp Ala Met Val Lys Ala Ala Asn Val Val Leu
            20                  25                  30

Leu Gly Tyr Glu Lys Ile Gly Ser Gly Leu Val Thr Val Met Val Arg
            35                  40                  45

Gly Asp Val Gly Ala Val Lys Ala Ala Thr Asp Ala Gly Ala Ala Ala
            50                  55                  60

Ala Lys Arg Val Gly Glu Val Val Ser Val His Val Ile Pro Arg Pro
65                  70                  75                  80

His Thr Asp Val Glu Lys Ile Leu Pro Ala Ala Asp Arg Lys
                85                  90

<210> SEQ ID NO 46
<211> LENGTH: 318
<212> TYPE: DNA
<213> ORGANISM: Artificial
<220> FEATURE:
<223> OTHER INFORMATION: artificial polynucleotide

<400> SEQUENCE: 46
atgcatcatc atcatcacca cggtagcggc agcggtagcg gcagcggtag cggcagcgag      60
gcgctgggta tggttgaaac ccgtggcctg gtgccggcga ttgaggcggc ggatgcgatg    120
```

```
gttaaggcgg cgaacgtggt tctgctgggt tacgaaaaaa ttggtagcgg cctggtgacc      180
gttatggttc gtggtgacgt tggtgcggtg aaagcggcga ccgatgcggg tgctgcggcg      240
gcgaaacgtg ttggcgaggt ggttagcgtt cacgtgatcc cgcgtccgca caccgatgtg      300
gaaaagattc tgccgtaa                                                    318
```

<210> SEQ ID NO 47
<211> LENGTH: 96
<212> TYPE: PRT
<213> ORGANISM: Fictibacillus gelatini

<400> SEQUENCE: 47

```
Met Ser Arg Glu Leu Thr Ala Leu Gly Met Ile Glu Thr Lys Gly Leu
1               5                   10                  15

Val Ala Ser Val Glu Ala Ala Asp Ala Met Val Lys Ala Ala Asn Val
                20                  25                  30

His Leu Val Gly Lys Val His Val Gly Gly Gly Leu Val Thr Val Leu
            35                  40                  45

Val Arg Gly Asp Val Gly Ala Val Lys Ala Ala Thr Glu Ala Gly Ala
        50                  55                  60

Ala Ala Ala Gln Arg Val Gly Glu Leu Leu Ser Val His Val Ile Pro
65                  70                  75                  80

Arg Pro His Asn Glu Leu Glu Ser Ile Leu Pro Lys Val Glu Thr Met
                85                  90                  95
```

<210> SEQ ID NO 48
<211> LENGTH: 321
<212> TYPE: DNA
<213> ORGANISM: Artificial
<220> FEATURE:
<223> OTHER INFORMATION: artificial polynucleotide

<400> SEQUENCE: 48

```
atgcatcatc atcatcacca cggcagcggt agcggcagcg gtagcggcag cggtagcctg       60
accgcgctgg gcatgatcga aaccaagggt ctggttgcga gcgtggaagc ggcggatgcg      120
atggttaagg cggcgaacgt tcacctggtg ggcaaagtgc acgttggtgg cggtctggtg      180
accgttctgg tgcgtggcga tgttggtgcg gtgaaagcgg cgaccgaggc gggtgctgcg      240
gcggcgcagc gtgtgggtga actgctgagc gttcacgtga tcccgcgtcc gcacaacgag      300
ctggaaagca ttctgccgta a                                                321
```

<210> SEQ ID NO 49
<211> LENGTH: 98
<212> TYPE: PRT
<213> ORGANISM: Marinobacter hydrocarbonoclasticus

<400> SEQUENCE: 49

```
Met Asn Glu Ala Leu Gly Ile Ile Glu Thr Lys Gly Leu Thr Ala Leu
1               5                   10                  15

Ile Glu Ala Ser Asp Ala Met Val Lys Ala Ala Arg Val Glu Leu Val
                20                  25                  30

Gly Tyr Lys Gln Ile Gly Ser Gly Leu Val Thr Ala Met Val Arg Gly
            35                  40                  45

Asp Val Ala Ala Cys Lys Ala Ala Thr Asp Ala Gly Ala Ala Ala Ala
        50                  55                  60

Gln Arg Leu Gly Glu Leu Val Ala Val His Val Ile Pro Arg Pro His
65                  70                  75                  80
```

Gly Asp Leu Glu Ala Ile Phe Pro Ile Asn Pro Ala Val Lys Pro Ser
                85                  90                  95

Gly Ala

<210> SEQ ID NO 50
<211> LENGTH: 324
<212> TYPE: DNA
<213> ORGANISM: Artificial
<220> FEATURE:
<223> OTHER INFORMATION: artificial polynucleotide

<400> SEQUENCE: 50
atgcatcatc atcatcacca cggtagcggc agcggtagcg gcagcggtag cggcagcgag    60
gcgctgggta tcattgaaac caaaggcctg accgcgctga ttgaggcgag cgatgcgatg   120
gtgaaggcgg cgcgtgttga actggtgggt tacaaacaga ttggtagcgg cctggttacc   180
gcgatggtgc gtggcgacgt ggcggcgtgc aaagcggcga ccgatgcggg tgctgcggcg   240
gcgcaacgtc tgggcgagct ggttgcggtt cacgtgatcc cgcgtccgca cggtgatctg   300
gaagcgatct tcccgattaa ctaa                                          324

<210> SEQ ID NO 51
<211> LENGTH: 92
<212> TYPE: PRT
<213> ORGANISM: Psychromonas hadalis

<400> SEQUENCE: 51

Met Asp Ala Leu Gly Ile Leu Glu Thr Lys Gly Leu Thr Ala Leu Ile
1               5                   10                  15

Glu Ala Ser Asp Ala Met Val Lys Ala Ala Ser Val Glu Leu Val Gly
                20                  25                  30

Tyr Gln Gln Ile Gly Ser Gly Tyr Val Thr Ala Phe Ile Arg Gly Asp
            35                  40                  45

Val Ala Ser Cys Lys Ala Ala Thr Asp Ala Gly Ser Val Val Ala Gln
        50                  55                  60

Arg Leu Gly Glu Leu Val Ala Val His Val Ile Pro Arg Pro His Gln
65                  70                  75                  80

Asp Leu Glu Ala Val Phe Pro Ile Thr Ala Lys Lys
                85                  90

<210> SEQ ID NO 52
<211> LENGTH: 333
<212> TYPE: DNA
<213> ORGANISM: Artificial
<220> FEATURE:
<223> OTHER INFORMATION: artificial polynucleotide

<400> SEQUENCE: 52
atgcatcatc atcaccacca cggttctggt tctggttctg gttctggttc tggttctgac    60
gctttaggta ttttagaaac aaaagggtta acggcattga tcgaagcatc tgatgcaatg   120
gttaaggctg caagtgttga attagttggc tatcagcaaa taggctctgg ttatgtcacg   180
gctttcattc gaggtgatgt tgcatcttgc aaagccgcta ctgatgcagg ctctgttgtt   240
gcacaacgct taggtgagtt agtggctgtc catgtgatac cgcgaccaca tcaagatctg   300
gaagctgttt ttcctatcac agcaaaaaag taa                                333

<210> SEQ ID NO 53
<211> LENGTH: 95
<212> TYPE: PRT

<213> ORGANISM: Spirochaeta alkalica

<400> SEQUENCE: 53

```
Met Ala Asp Val Gln Met Ile Ala Leu Gly Met Ile Glu Thr Lys Gly
1               5                   10                  15
Leu Val Ala Ala Ile Glu Ala Ala Asp Ala Met Val Lys Ala Ala Asn
            20                  25                  30
Val Lys Leu Ile Gly Lys Glu Tyr Ile Gly Gly Gly Leu Val Thr Val
        35                  40                  45
Met Val Arg Gly Asp Val Gly Ala Val Lys Ala Ala Thr Asp Ala Gly
    50                  55                  60
Ala Ala Ala Ala Gln Arg Ile Gly Glu Leu Val Ser Val His Val Ile
65                  70                  75                  80
Pro Arg Pro His Gly Asp Ala Glu Met Ile Leu Pro Ser Ala Lys
                85                  90                  95
```

<210> SEQ ID NO 54
<211> LENGTH: 321
<212> TYPE: DNA
<213> ORGANISM: Artificial
<220> FEATURE:
<223> OTHER INFORMATION: artificial polynucleotide

<400> SEQUENCE: 54

```
atgcatcatc atcatcacca cggcagcggt agcggcagcg gtagcggcag cgtagcatg      60
atcgcgctgg gcatgattga aaccaagggt ctggtggcgg cgattgaagc ggcggatgcg    120
atggtgaaag cggcgaacgt taagctgatc ggcaaagagt acattggtgg cggtctggtg    180
accgttatgg ttcgtggcga cgtgggtgcg gttaaagcgg cgaccgatgc gggtgctgcg    240
gcggcgcagc gtatcggcga gctggttagc gtgcacgtta ttccgcgtcc gcacggtgat    300
gcggaaatga ttctgccgta a                                              321
```

<210> SEQ ID NO 55
<211> LENGTH: 95
<212> TYPE: PRT
<213> ORGANISM: Thauera linaloolentis

<400> SEQUENCE: 55

```
Met Glu Ala Leu Gly Leu Ile Glu Thr Lys Gly Leu Val Ala Leu Ile
1               5                   10                  15
Glu Ala Ser Asp Ala Met Val Lys Ala Ala Arg Val Lys Leu Val Gly
            20                  25                  30
Val Lys Gln Ile Gly Gly Gly Phe Val Thr Ala Met Val Arg Gly Asp
        35                  40                  45
Val Ala Ala Cys Lys Ala Ala Thr Asp Ala Gly Ala Ala Ala Ala Gln
    50                  55                  60
Arg Ile Gly Glu Leu Val Ser Val His Val Ile Pro Arg Pro His Gly
65                  70                  75                  80
Asp Leu Glu Glu Val Phe Pro Ile Lys Met Glu Ser Gly Leu Asp
                85                  90                  95
```

<210> SEQ ID NO 56
<211> LENGTH: 342
<212> TYPE: DNA
<213> ORGANISM: Artificial
<220> FEATURE:
<223> OTHER INFORMATION: artificial polynucleotide

<400> SEQUENCE: 56

```
atgcatcatc atcaccacca cggttctggt tctggttctg gttctggttc tggttctgaa      60
gccctgggac tgatcgaaac gaaaggcctg gttgcattga tcgaagcctc cgacgccatg     120
gtcaaggccg cgcgcgtcaa gttggtcggc gtcaagcaga tcggcggcgg tttcgtcacc     180
gcgatggtgc gtggcgacgt ggccgcctgc aaggccgcca ccgatgccgg cgcggctgcc     240
gcgcaacgga ttggcgaact ggtgtcggta cacgtgattc gcgtccgca cggcgatctg      300 gaagaagtgt tcccgatcaa gatggaaagc ggactggact ga                        342
```

<210> SEQ ID NO 57
<211> LENGTH: 92
<212> TYPE: PRT
<213> ORGANISM: Thermoanaerobacterium saccharolyticum

<400> SEQUENCE: 57

```
Met Val Gln Glu Ala Leu Gly Met Val Glu Thr Arg Gly Leu Val Ala
1               5                   10                  15

Ala Ile Glu Ala Ala Asp Ala Met Val Lys Ala Ala Asp Val Thr Leu
            20                  25                  30

Ile Gly Thr Glu Lys Ile Gly Ser Gly Leu Val Thr Val Met Val Arg
        35                  40                  45

Gly Asp Val Gly Ala Val Lys Ala Ala Thr Glu Val Gly Ala Ser Ala
    50                  55                  60

Ala Ser Lys Leu Gly Glu Leu Val Ala Val His Val Ile Pro Arg Pro
65                  70                  75                  80

His Thr Asp Val Glu Lys Ile Leu Pro Thr Ile Lys
                85                  90
```

<210> SEQ ID NO 58
<211> LENGTH: 318
<212> TYPE: DNA
<213> ORGANISM: Artificial
<220> FEATURE:
<223> OTHER INFORMATION: artificial polynucleotide

<400> SEQUENCE: 58

```
atgcatcatc atcatcacca cggtagcggc agcggtagcg gcagcggtag cggcagcgag      60
gcgctgggta tggtggaaac ccgtggcctg gttgcggcga ttgaggcggc ggatgcgatg     120
gtgaaggcgg cggatgttac cctgatcggc accgaaaaaa ttggtagcgg cctggtgacc     180
gttatggttc gtggtgacgt tggtgcggtt aaagcggcga ccgaggtggg tgcgagcgcg     240
gcgagcaaac tgggcgaact ggttgcggtg cacgttatcc cgcgtccgca caccgatgtt     300
gagaagattc tgccgtaa                                                    318
```

<210> SEQ ID NO 59
<211> LENGTH: 97
<212> TYPE: PRT
<213> ORGANISM: Bacillus megaterium

<400> SEQUENCE: 59

```
Met Ala Arg Glu Leu Thr Ala Leu Gly Met Ile Glu Thr Lys Gly Leu
1               5                   10                  15

Val Ala Ser Val Glu Ala Ala Asp Ala Met Val Lys Ala Ala Asn Val
            20                  25                  30

His Leu Val Asp Lys Val His Val Gly Gly Gly Ile Val Thr Val Leu
        35                  40                  45

Val Arg Gly Asp Val Gly Ala Val Lys Ala Ala Thr Asp Ser Gly Ala
```

```
            50                  55                  60
Ala Ala Ala Gln Arg Val Gly Glu Leu Ile Ser Val His Val Ile Pro
 65                  70                  75                  80

Arg Pro His Asn Glu Leu Glu Ser Ile Leu Pro Lys Ile Asp Ser Glu
                 85                  90                  95

Leu

<210> SEQ ID NO 60
<211> LENGTH: 294
<212> TYPE: DNA
<213> ORGANISM: Artificial
<220> FEATURE:
<223> OTHER INFORMATION: artificial polynucleotide

<400> SEQUENCE: 60
atggcaagag aactaacagc attaggcatg attgaaacaa aaggattagt agcatcagta      60
gaggcagcag acgcaatggt aaaagcagca aatgtacatt tagttggtaa agttcacgta     120
ggtggaggaa ttgtaacggt tttagtacgc ggtgacgtag gcgcggtaaa agcagcgaca     180
gattctggtg cagcagctgc acagcgcgtt ggagaactta tttccgttca cgttatccca     240 cgccccacaca atgaattaga agtattttta ccgaaaatcg atagtgaact ataa          294

<210> SEQ ID NO 61
<211> LENGTH: 18
<212> TYPE: DNA
<213> ORGANISM: Artificial primer
<220> FEATURE:
<223> OTHER INFORMATION: artificial polynucleotide

<400> SEQUENCE: 61
gcggccgcct cgaggccc                                                    18

<210> SEQ ID NO 62
<211> LENGTH: 20
<212> TYPE: DNA
<213> ORGANISM: Artificial primer
<220> FEATURE:
<223> OTHER INFORMATION: artificial polynucleotide

<400> SEQUENCE: 62
ggatccagat ccctccttcg                                                  20

<210> SEQ ID NO 63
<211> LENGTH: 40
<212> TYPE: DNA
<213> ORGANISM: Artificial primer
<220> FEATURE:
<223> OTHER INFORMATION: artificial polynucleotide

<400> SEQUENCE: 63
cgaaggaggg atctggatcc gcactgggta tgatcgaaac                            40

<210> SEQ ID NO 64
<211> LENGTH: 38
<212> TYPE: DNA
<213> ORGANISM: Artificial primer
<220> FEATURE:
<223> OTHER INFORMATION: artificial polynucleotide

<400> SEQUENCE: 64
ttgggcctcg aggcggccgc ttacggcaga atggtttc                              38
```

-continued

```
<210> SEQ ID NO 65
<211> LENGTH: 38
<212> TYPE: DNA
<213> ORGANISM: Artificial primer
<220> FEATURE:
<223> OTHER INFORMATION: artificial polynucleotide

<400> SEQUENCE: 65
cgaaggaggg atctggatcc gcgcgcgaaa ttaacggc                               38

<210> SEQ ID NO 66
<211> LENGTH: 48
<212> TYPE: DNA
<213> ORGANISM: Artificial primer
<220> FEATURE:
<223> OTHER INFORMATION: artificial polynucleotide

<400> SEQUENCE: 66
ttgggcctcg aggcggccgc ttaatattct tccagtttcg gcagaatg                   48

<210> SEQ ID NO 67
<211> LENGTH: 38
<212> TYPE: DNA
<213> ORGANISM: Artificial primer
<220> FEATURE:
<223> OTHER INFORMATION: artificial polynucleotide

<400> SEQUENCE: 67
cgaaggaggg atctggatcc gagagcctgg gtttcatc                              38

<210> SEQ ID NO 68
<211> LENGTH: 38
<212> TYPE: DNA
<213> ORGANISM: Artificial primer
<220> FEATURE:
<223> OTHER INFORMATION: artificial polynucleotide

<400> SEQUENCE: 68
ttgggcctcg aggcggccgc ttacggcagc agcttctg                              38

<210> SEQ ID NO 69
<211> LENGTH: 38
<212> TYPE: DNA
<213> ORGANISM: Artificial primer
<220> FEATURE:
<223> OTHER INFORMATION: artificial polynucleotide

<400> SEQUENCE: 69
cgaaggaggg atctggatcc gaggcgctgg gcctgatc                              38

<210> SEQ ID NO 70
<211> LENGTH: 45
<212> TYPE: DNA
<213> ORGANISM: Artificial primer
<220> FEATURE:
<223> OTHER INFORMATION: artificial polynucleotide

<400> SEQUENCE: 70
ttgggcctcg aggcggccgc ttatttcttc gcttgcggca gaatc                      45

<210> SEQ ID NO 71
<211> LENGTH: 43
<212> TYPE: DNA
<213> ORGANISM: Artificial primer
<220> FEATURE:
<223> OTHER INFORMATION: artificial polynucleotide
```

<400> SEQUENCE: 71
cgaaggaggg atctggatcc gattcattag gaatgattga aac       43

<210> SEQ ID NO 72
<211> LENGTH: 39
<212> TYPE: DNA
<213> ORGANISM: Artificial primer
<220> FEATURE:
<223> OTHER INFORMATION: artificial polynucleotide

<400> SEQUENCE: 72
ttgggcctcg aggcggccgc ctatttgtca cgtttgaag       39

<210> SEQ ID NO 73
<211> LENGTH: 39
<212> TYPE: DNA
<213> ORGANISM: Artificial primer
<220> FEATURE:
<223> OTHER INFORMATION: artificial polynucleotide

<400> SEQUENCE: 73
cgaaggaggg atctggatcc gaggcgctgg gtatggttg       39

<210> SEQ ID NO 74
<211> LENGTH: 44
<212> TYPE: DNA
<213> ORGANISM: Artificial primer
<220> FEATURE:
<223> OTHER INFORMATION: artificial polynucleotide

<400> SEQUENCE: 74
ttgggcctcg aggcggccgc ttacggcaga atcttttcca catc       44

<210> SEQ ID NO 75
<211> LENGTH: 38
<212> TYPE: DNA
<213> ORGANISM: Artificial primer
<220> FEATURE:
<223> OTHER INFORMATION: artificial polynucleotide

<400> SEQUENCE: 75
cgaaggaggg atctggatcc ctgaccgcgc tgggcatg       38

<210> SEQ ID NO 76
<211> LENGTH: 44
<212> TYPE: DNA
<213> ORGANISM: Artificial primer
<220> FEATURE:
<223> OTHER INFORMATION: artificial polynucleotide

<400> SEQUENCE: 76
ttgggcctcg aggcggccgc ttacggcaga atgctttcca gctc       44

<210> SEQ ID NO 77
<211> LENGTH: 39
<212> TYPE: DNA
<213> ORGANISM: Artificial primer
<220> FEATURE:
<223> OTHER INFORMATION: artificial polynucleotide

<400> SEQUENCE: 77
cgaaggaggg atctggatcc gaggcgctgg gtatcattg       39

<210> SEQ ID NO 78
<211> LENGTH: 41

```
<212> TYPE: DNA
<213> ORGANISM: Artificial primer
<220> FEATURE:
<223> OTHER INFORMATION: artificial polynucleotide

<400> SEQUENCE: 78
ttgggcctcg aggcggccgc ttagttaatc gggaagatcg c                    41

<210> SEQ ID NO 79
<211> LENGTH: 43
<212> TYPE: DNA
<213> ORGANISM: Artificial primer
<220> FEATURE:
<223> OTHER INFORMATION: artificial polynucleotide

<400> SEQUENCE: 79
cgaaggaggg atctggatcc gacgctttag gtattttaga aac                  43

<210> SEQ ID NO 80
<211> LENGTH: 41
<212> TYPE: DNA
<213> ORGANISM: Artificial primer
<220> FEATURE:
<223> OTHER INFORMATION: artificial polynucleotide

<400> SEQUENCE: 80
ttgggcctcg aggcggccgc ttacttttt gctgtgatag g                     41

<210> SEQ ID NO 81
<211> LENGTH: 38
<212> TYPE: DNA
<213> ORGANISM: Artificial primer
<220> FEATURE:
<223> OTHER INFORMATION: artificial polynucleotide

<400> SEQUENCE: 81
cgaaggaggg atctggatcc atgatcgcgc tgggcatg                        38

<210> SEQ ID NO 82
<211> LENGTH: 41
<212> TYPE: DNA
<213> ORGANISM: Artificial primer
<220> FEATURE:
<223> OTHER INFORMATION: artificial polynucleotide

<400> SEQUENCE: 82
ttgggcctcg aggcggccgc ttacggcaga atcatttccg c                    41

<210> SEQ ID NO 83
<211> LENGTH: 43
<212> TYPE: DNA
<213> ORGANISM: Artificial primer
<220> FEATURE:
<223> OTHER INFORMATION: artificial polynucleotide

<400> SEQUENCE: 83
cgaaggaggg atctggatcc gaagcattag gaatgattga aac                  43

<210> SEQ ID NO 84
<211> LENGTH: 38
<212> TYPE: DNA
<213> ORGANISM: Artificial primer
<220> FEATURE:
<223> OTHER INFORMATION: artificial polynucleotide

<400> SEQUENCE: 84
```
ttgggcctcg aggcggccgc tcaaatgttg ctgtcgcc                                38

<210> SEQ ID NO 85
<211> LENGTH: 38
<212> TYPE: DNA
<213> ORGANISM: Artificial primer
<220> FEATURE:
<223> OTHER INFORMATION: artificial polynucleotide

<400> SEQUENCE: 85
cgaaggaggg atctggatcc gaagccctgg gactgatc                                38

<210> SEQ ID NO 86
<211> LENGTH: 38
<212> TYPE: DNA
<213> ORGANISM: Artificial primer
<220> FEATURE:
<223> OTHER INFORMATION: artificial polynucleotide

<400> SEQUENCE: 86
ttgggcctcg aggcggccgc tcagtccagt ccgctttc                                38

<210> SEQ ID NO 87
<211> LENGTH: 38
<212> TYPE: DNA
<213> ORGANISM: Artificial primer
<220> FEATURE:
<223> OTHER INFORMATION: artificial polynucleotide

<400> SEQUENCE: 87
cgaaggaggg atctggatcc gaggcgctgg gtatggtg                                38

<210> SEQ ID NO 88
<211> LENGTH: 44
<212> TYPE: DNA
<213> ORGANISM: Artificial primer
<220> FEATURE:
<223> OTHER INFORMATION: artificial polynucleotide

<400> SEQUENCE: 88
ttgggcctcg aggcggccgc ttacggcaga atcttctcaa catc                         44

<210> SEQ ID NO 89
<211> LENGTH: 345
<212> TYPE: DNA
<213> ORGANISM: Artificial
<220> FEATURE:
<223> OTHER INFORMATION: fusion protein

<400> SEQUENCE: 89
atgcatcatc atcaccacca cggttctggt tctggttctg gttctggttc tggttctgaa        60
gcattaggaa tgattgaaac cggggcctg gttgcgctga ttgaggcctc cgatgcgatg        120
gtaaaagccg cgcgcgtgaa gctggtcggc gtgaagcaga ttggcggtgg cctgtgtact       180
gccatggtgc gtggcgatgt ggcggcgtgc aaagccgcaa ccgatgctgg cgccgctgcg       240
gcgcagcgca ttggcgagtt ggtctccgta cacgtgattc cacgcccgca cggcgatctg       300
gaagaagtgt tcccgatcag cttcaaaggc gacagcaaca tttga                      345

<210> SEQ ID NO 90
<211> LENGTH: 333
<212> TYPE: DNA
<213> ORGANISM: Artificial
<220> FEATURE:
<223> OTHER INFORMATION: fusion protein

<400> SEQUENCE: 90

```
atgcatcatc atcaccacca cggttctggt tctggttctg gttctggttc tggttctgat    60
tcattaggaa tgattgaaac taagggcttg atcgcactta ttgaagcttc agatgcaatg   120
gtaaaggctg ctcgtgtaca acttgtaggt acaaacaaa ttggtgctgg tttggtaact   180
gcgattgttc gtggtgatgt tgcagcatgt aaagcagcaa ccgatgcagg tgcagcagca   240
gccgcacgta ttggcgaggt ggtagctgta cacgttattc cacgtccaca tggtgacctg   300
gaagaagtat ttcccttcaa acgtgacaaa tag                                333
```

<210> SEQ ID NO 91
<211> LENGTH: 351
<212> TYPE: DNA
<213> ORGANISM: Artificial
<220> FEATURE:
<223> OTHER INFORMATION: fusion protein

<400> SEQUENCE: 91

```
atgcatcatc atcatcacca cggtagcggc agcggtagcg gcagcggtag cggcagcaac    60
gaggcgctgg gtatcattga aaccaaaggc ctgaccgcgc tgattgaggc gagcgatgcg   120
atggtgaagg cggcgcgtgt tgaactggtg ggttacaaac agattggtag cggcctggtt   180
accgcgatgg tgcgtggcga cgtggcggcg tgcaaagcgg cgaccgatgc gggtgctgcg   240
gcggcgcaac gtctgggcga gctggttgcg gttcacgtga tcccgcgtcc gcacggtgat   300
ctggaagcga tcttcccgat taacccggcg gtgaaaccga gcggcgcgta a             351
```

<210> SEQ ID NO 92
<211> LENGTH: 342
<212> TYPE: DNA
<213> ORGANISM: Artificial
<220> FEATURE:
<223> OTHER INFORMATION: artificial polypeptide

<400> SEQUENCE: 92

```
atgcatcatc atcaccacca cggttctggt tctggttctg gttctggttc tggttctgaa    60
gccctgggac tgatcgaaac gaaaggcctg gttgcattga tcgaagcctc cgacgccatg   120
gtcaaggccg cgcgcgtcaa gttggtcggc gtcaagcaga tcggcggcgg tttcgtcacc   180
gcgatggtgc gtggcgacgt ggccgcctgc aaggccgcca ccgatgccgg cgcggctgcc   240
gcgcaacgga ttggcgaact ggtgtcggta cacgtgattc gcgtccgca cggcgatctg   300
gaagaagtgt tcccgatcaa gatggaaagc ggactggact ga                      342
```

<210> SEQ ID NO 93
<211> LENGTH: 333
<212> TYPE: DNA
<213> ORGANISM: Artificial
<220> FEATURE:
<223> OTHER INFORMATION: fusion protein

<400> SEQUENCE: 93

```
atgcatcatc atcaccacca cggttctggt tctggttctg gttctggttc tggttctgac    60
gctttaggta ttttagaaac aaaagggtta acggcattga tcgaagcatc tgatgcaatg   120
gttaaggctg caagtgttga attagttggc tatcagcaaa taggctctgg ttatgtcacg   180
gctttcattc gaggtgatgt tgcatcttgc aaagccgcta ctgatgcagg ctctgttgtt   240
gcacaacgct taggtgagtt agtggctgtc catgtgatac cgcgaccaca tcaagatctg   300
```

```
gaagctgttt tcctatcac agcaaaaaag taa                                    333
```

<210> SEQ ID NO 94
<211> LENGTH: 342
<212> TYPE: DNA
<213> ORGANISM: Artificial
<220> FEATURE:
<223> OTHER INFORMATION: fusion protein

<400> SEQUENCE: 94

```
atgcatcatc atcatcacca cggtagcggc agcggtagcg gcagcggtag cggcagcaac     60
gagagcctgg gtttcatcga aacccgtggc tttaccgcgg cgattgaagc ggcggatgcg    120
atgctgaagg cggcgaacgt tgagatcgtg ggtagcgaaa aaattggtag cggcctggtg    180
agcgttatcg tgaagggtga tgttggcgcg gtgaaagcgg cgaccgaggt tggtgcggaa    240
gcggcgggtc gtgttggcga agtgatcgcg gttcacgtga ttccgcgtcc gcacggcgac    300
attcagaagc tgctgccgac cgtgaaagat gatgcggtgt aa                      342
```

<210> SEQ ID NO 95
<211> LENGTH: 339
<212> TYPE: DNA
<213> ORGANISM: Artificial
<220> FEATURE:
<223> OTHER INFORMATION: fusion protein

<400> SEQUENCE: 95

```
atgcatcatc atcatcacca cggtagcggc agcggtagcg gcagcggtag cggcagcacc     60
ggcgaggcgc tgggtatggt tgaaacccgt ggcctggtgc cggcgattga ggcggcggat    120
gcgatggtta aggcggcgaa cgtggttctg ctgggttacg aaaaaattgg tagcggcctg    180
gtgaccgtta tggttcgtgg tgacgttggt gcggtgaaag cggcgaccga tgcgggtgct    240
gcggcggcga acgtgttggc gaggtggtt agcgttcacg tgatcccgcg tccgcacacc    300
gatgtggaaa agattctgcc ggcggcggat cgcaaataa                           339
```

<210> SEQ ID NO 96
<211> LENGTH: 333
<212> TYPE: DNA
<213> ORGANISM: Artificial
<220> FEATURE:
<223> OTHER INFORMATION: fusion protein

<400> SEQUENCE: 96

```
atgcatcatc atcatcacca cggtagcggc agcggtagcg gcagcggtag cggcagcgtg     60
caggaggcgc tgggtatggt ggaaacccgt ggcctggttg cggcgattga ggcggcggat    120
gcgatggtga aggcggcgga tgttaccctg atcggcaccg aaaaaattgg tagcggcctg    180
gtgaccgtta tggttcgtgg tgacgttggt gcggttaaag cggcgaccga ggtgggtgcg    240
agcgcggcga gcaaactggg cgaactggtt gcggtgcacg ttatcccgcg tccgcacacc    300
gatgttgaga agattctgcc gaccattaaa taa                                 333
```

<210> SEQ ID NO 97
<211> LENGTH: 339
<212> TYPE: DNA
<213> ORGANISM: Artificial
<220> FEATURE:
<223> OTHER INFORMATION: fusion protein

<400> SEQUENCE: 97

```
atgcatcatc atcatcacca cggcagcggt agcggcagcg gtagcggcag cggtagcgcg     60
```

```
attagcaacg cactgggtat gatcgaaacc aagggcctgg ttggtgcgat tgaagcggcg    120
gacgcgatgg ttaaggcggc gaacgtgacc ctgctgggta agagcacgt gggtggcggt     180 ctggtgaccg ttatggtgcg tggcgacgtt ggtgcggtga agcggcgac cgatgcgggt     240 gctgcggcgc ggagcgtgt tggtgaactg atgagcgttc atgtgatccc gcgtccgcac     300
ggcgaggtgg aaaccattct gccgcagatt aaagaataa                           339
```

<210> SEQ ID NO 98
<211> LENGTH: 348
<212> TYPE: DNA
<213> ORGANISM: Artificial
<220> FEATURE:
<223> OTHER INFORMATION: fusion protein

<400> SEQUENCE: 98

```
atgcatcatc atcatcacca cggcagcggt agcggcagcg gtagcggcag cggtagcgcg    60
cgcgaaatta acggcgcact gggtatgatc gaaacccgtg gtctggtggc gagcctggag   120
gcggcggatg cgatggtgaa ggcggcgaac gttaacatcg tgggcaaagt gcacgttggt   180
ggcggtattg tgaccgttct ggtgaccggc gatgttggtg cggtgaaagc ggcgaccgag   240
gcgggcagca ccgcggcgca cgtgttggt gaaatcatta gcgttcatgt gatcccgcgt    300
ccgcaccatg agctgggtag cattctgccg aaactggaag aatattaa                348
```

<210> SEQ ID NO 99
<211> LENGTH: 345
<212> TYPE: DNA
<213> ORGANISM: Artificial
<220> FEATURE:
<223> OTHER INFORMATION: fusion protein

<400> SEQUENCE: 99

```
atgcatcatc atcatcacca cggcagcggt agcggcagcg gtagcggcag cggtagcaac    60
aaaaccgagg cgctgggcct gatcgaaacc aagggcctgg ttggtgcgat tgaggcggcg   120
gacgcgatgg ttaaagcggc gaacgtgtac ctgatcggtc gtgaactggt gggtggcggt   180
ctggtgaccg ttatggttcg tggcgacgtt ggtgcggtga agcggcgac cgatgcgggt    240 gctgcggcgg cgcagcgtgt tggcgagctg atcagcgttc acgtgattcc gcgtccgcac   300
ggcgatgtgg aaatgattct gccgcaagcg aagaaagaag cgtaa                    345
```

<210> SEQ ID NO 100
<211> LENGTH: 345
<212> TYPE: DNA
<213> ORGANISM: Artificial
<220> FEATURE:
<223> OTHER INFORMATION: fusion protein

<400> SEQUENCE: 100

```
atgcatcatc atcatcacca cggcagcggt agcggcagcg gtagcggcag cggtagcagc    60
cgcgaactga ccgcgctggg catgatcgaa accaagggtc tggttgcgag cgtggaagcg   120
gcggatgcga tggttaaggc ggcgaacgtt cacctggtgg gcaaagtgca cgttggtggc   180
ggtctggtga ccgttctggt gcgtggcgat gttggtgcgg tgaaagcggc gaccgaggcg   240
ggtgctgcgg cggcgcagcg tgtgggtgaa ctgctgagcg ttcacgtgat cccgcgtccg   300
cacaacgagc tggaaagcat tctgccgaaa gtggaaacca tgtaa                    345
```

<210> SEQ ID NO 101

```
<211> LENGTH: 342
<212> TYPE: DNA
<213> ORGANISM: Artificial
<220> FEATURE:
<223> OTHER INFORMATION: fusion protein

<400> SEQUENCE: 101
atgcatcatc atcatcacca cggcagcggt agcggcagcg gtagcggcag cggtagcgcg      60
gatgtgcaga tgatcgcgct gggcatgatt gaaaccaagg gtctggtggc ggcgattgaa     120
gcggcggatg cgatggtgaa agcggcgaac gttaagctga tcggcaaaga gtacattggt     180
ggcggtctgg tgaccgttat ggttcgtggc gacgtgggtg cggttaaagc ggcgaccgat     240
gcgggtgctg cggcggcgca cgtatcggc gagctggtta gcgtgcacgt tattccgcgt      300
ccgcacggtg atgcggaaat gattctgccg agcgcgaaat aa                        342

<210> SEQ ID NO 102
<211> LENGTH: 342
<212> TYPE: DNA
<213> ORGANISM: Artificial
<220> FEATURE:
<223> OTHER INFORMATION: artificial polynucleotide

<400> SEQUENCE: 102
atgcatcatc atcaccacca cggttctggt tctggttctg gttctggttc tggttctgaa      60
gcattaggaa tgattgaaac ccgggggcctg gttgcgctga ttgaggcctc cgatgcgatg    120
gtaaaagccg cgcgcgtgaa gctggtcggc gtgaagcaga ttggcggtgg cctgtgtact    180
gccatggtgc gtggcgatgt ggcggcgtgc aaagccgcaa ccgatgctgg cgccgctgcg    240
gcgcagcgca ttggcgagtt ggtctccgta cacgtgattc cacgcccgca cggcgatctg    300
gaagaagtgt cccgatcaa gatggaaagc ggactggact ga                        342

<210> SEQ ID NO 103
<211> LENGTH: 342
<212> TYPE: DNA
<213> ORGANISM: Artificial
<220> FEATURE:
<223> OTHER INFORMATION: artificial polynucleotide

<400> SEQUENCE: 103
atgcatcatc atcaccacca cggttctggt tctggttctg gttctggttc tggttctgat      60
tcattaggaa tgattgaaac taagggcttg atcgcactta ttgaagcttc agatgcaatg    120
gtaaaggctg ctcgtgtaca acttgtaggt tacaaacaaa ttggtgctgg tttggtaact   180
gcgattgttc gtggtgatgt tgcagcatgt aaagcagcaa ccgatgcagg tgcagcagca   240
gccgcacgta ttggcgaggt ggtagctgta cacgttattc cacgtccaca tggtgacctg   300
gaagaagtat ttcccttcaa gatggaaagc ggactggact ag                        342

<210> SEQ ID NO 104
<211> LENGTH: 962
<212> TYPE: DNA
<213> ORGANISM: Artificial
<220> FEATURE:
<223> OTHER INFORMATION: artificial polynucleotide

<400> SEQUENCE: 104
atgaacgaag gagggatctg gatccatgga agcattagga atgattgaaa cccgggggcct     60 ggttgcgctg attgaggcct ccgatgcgat ggtaaaagcc gcgcgcgtga agctggtcgg    120
cgtgaagcag attggcggtg gcctgtgtac tgccatggtg cgtggcgatg tggcggcgtg    180
```

```
caaagccgca accgatgctg gcgccgctgc ggcgcagcgc attggcgagt tggtctccgt    240
acacgtgatt ccacgcccgc acggcgatct ggaagaagtg ttcccgatca gcttcaaagg    300
cgacagcaac atttgaatga acgaaggagg gatctggatc catgcatcat catcaccacc    360
acggttctgg ttctggttct ggttctggtt ctggttctga agcattagga atgattgaaa    420
cccggggcct ggttgcgctg attgaggcct ccgatgcgat ggtaaaagcc gcgcgcgtga    480
agctggtcgg cgtgaagcag attggcggtg gcctgtgtac tgccatggtg cgtggcgatg    540
tggcggcgtg caaagccgca accgatgctg gcgccgctgc ggcgcagcgc attggcgagt    600
tggtctccgt acacgtgatt ccacgcccgc acggcgatct ggaagaagtg ttcccgatca    660
gcttcaaagg cgacagcaac attgtcgacg ggagtggtgg cagcggaggc gatagtgcta    720
cccatattaa attctcaaaa cgtgatgagg acggcaaaga gttagctggt gcaactatgg    780
agttgcgtga ttcatctggt aaaactatta gtacatggat ttcagatgga caagtgaaag    840
atttctacct gtatccagga aaatatacat ttgtcgaaac cgcagcacca gacggttatg    900
aggtagcaac tgctattacc tttacagtta atgagcaagg tcaggttact gtaaatggct    960
ga                                                                    962

<210> SEQ ID NO 105
<211> LENGTH: 968
<212> TYPE: DNA
<213> ORGANISM: Artificial
<220> FEATURE:
<223> OTHER INFORMATION: artificial polynucleotide

<400> SEQUENCE: 105
atgaacgaag gagggatctg gatccatgaa cgaggcgctg gtatcattg aaaccaaagg     60 cctgaccgcg ctgattgagg cgagcgatgc gatggtgaag gcggcgcgtg ttgaactggt    120
gggttacaaa cagattggta gcggcctggt taccgcgatg gtgcgtggcg acgtggcggc    180
gtgcaaagcg gcgaccgatg cgggtgctgc ggcggcgcaa cgtctgggcg agctggttgc    240
ggttcacgtg atcccgcgtc cgcacggtga tctggaagcg atcttcccga ttaacccggc    300
ggtgaaaccg agcggcgcgt aaatgaacga aggagggatc tggatccatg catcatcatc    360
accaccacgg ttctggttct ggttctggtt ctggttctgg ttctgaagca ttaggaatga    420
ttgaaacccg gggcctggtt gcgctgattg aggcctccga tgcgatggta aaagccgcgc    480
gcgtgaagct ggtcggcgtg aagcagattg gcggtggcct gtgtactgcc atggtgcgtg    540
gcgatgtggc ggcgtgcaaa gccgcaaccg atgctggcgc cgctgcggcg cagcgcattg    600
gcgagttggt ctccgtacac gtgattccac gcccgcacgg cgatctggaa gaagtgttcc    660
cgatcagctt caaggcgac agcaacattg tcgacgggag tggtggcagc ggaggcgata    720
gtgctaccca tattaaattc tcaaaacgtg atgaggacgg caaagagtta gctggtgcaa    780
ctatggagtt gcgtgattca tctggtaaaa ctattagtac atggatttca gatggacaag    840
tgaaagattt ctacctgtat ccaggaaaat atacatttgt cgaaaccgca gcaccagacg    900
gttatgaggt agcaactgct attacctta cagttaatga gcaaggtcag gttactgtaa    960
atggctga                                                             968

<210> SEQ ID NO 106
<211> LENGTH: 959
<212> TYPE: DNA
<213> ORGANISM: Artificial
<220> FEATURE:
```

<223> OTHER INFORMATION: artificial polynucleotide

<400> SEQUENCE: 106

| | |
|---|---:|
| atgaacgaag gagggatctg gatccatgcg cgaactgacc gcgctgggca tgatcgaaac | 60 |
| caagggtctg gttgcgagcg tggaagcggc ggatgcgatg gttaaggcgg cgaacgttca | 120 |
| cctggtgggc aaagtgcacg ttggtggcgg tctggtgacc gttctggtgc gtggcgatgt | 180 |
| tggtgcggtg aaagcggcga ccgaggcggg tgctgcggcg cgcagcgtg tgggtgaact | 240 |
| gctgagcgtt cacgtgatcc cgcgtccgca caacgagctg gaaagcattc tgccgaaagt | 300 |
| ggaaaccatg taaatgaacg aaggagggat ctggatccat gcatcatcat caccaccacg | 360 |
| gttctggttc tggttctggt tctggttctg gttctgaagc attaggaatg attgaaaccc | 420 |
| ggggcctggt tgcgctgatt gaggcctccg atgcgatggt aaaagccgcg cgcgtgaagc | 480 |
| tggtcggcgt gaagcagatt ggcggtggcc tgtgtactgc catggtgcgt ggcgatgtgg | 540 |
| cggcgtgcaa agccgcaacc gatgctggcc cgctgcggc gcagcgcatt ggcgagttgg | 600 |
| tctccgtaca cgtgattcca cgcccgcacg gcgatctgga agaagtgttc ccgatcagct | 660 |
| tcaaaggcga cagcaacatt gtcgacggga gtggtggcag cggaggcgat agtgctaccc | 720 |
| atattaaatt ctcaaaacgt gatgaggacg gcaaagagtt agctggtgca actatggagt | 780 |
| tgcgtgattc atctggtaaa actattagta catggatttc agatggacaa gtgaaagatt | 840 |
| tctacctgta tccaggaaaa tatacatttg tcgaaaccgc agcaccagac ggttatgagg | 900 |
| tagcaactgc tattacccttt acagttaatg agcaaggtca ggttactgta aatggctga | 959 |

<210> SEQ ID NO 107
<211> LENGTH: 950
<212> TYPE: DNA
<213> ORGANISM: Artificial
<220> FEATURE:
<223> OTHER INFORMATION: artificial polynucleotide

<400> SEQUENCE: 107

| | |
|---|---:|
| atgaacgaag gagggatctg gatccatggt gcaggaggcg ctgggtatgg tggaaacccg | 60 |
| tggcctggtt gcggcgattg aggcggcgga tgcgatggtg aaggcggcgg atgttaccct | 120 |
| gatcggcacc gaaaaaattg gtagcggcct ggtgaccgtt atggttcgtg gtgacgttgg | 180 |
| tgcggttaaa gcggcgaccg aggtgggtgc gagcgcggcg agcaaactgg gcgaactggt | 240 |
| tgcggtgcac gttatcccgc gtccgcacac cgatgttgag aagattctgc gaccattaa | 300 |
| ataaatgaac gaaggaggga tctggatcca tgcatcatca tcaccaccac ggttctggtt | 360 |
| ctggttctgg ttctggttct ggttctgaag cattaggaat gattgaaacc cggggcctgg | 420 |
| ttgcgctgat tgaggcctcc gatgcgatgg taaaagccgc gcgcgtgaag ctggtcggcg | 480 |
| tgaagcagat tggcggtggc ctgtgtactg ccatggtgcg tggcgatgtg gcggcgtgca | 540 |
| aagccgcaac cgatgctggc cgctgcggc gcagcgcatt ggcgagttg gtctccgtac | 600 |
| acgtgattcc acgcccgcac ggcgatctgg aagaagtgtt cccgatcagc ttcaaaggcg | 660 |
| acagcaacat tgtcgacggg agtggtggca gcggaggcga tagtgctacc catattaaat | 720 |
| tctcaaaacg tgatgaggac ggcaaagagt tagctggtgc aactatggag ttgcgtgatt | 780 |
| catctggtaa aactattagt acatggattt cagatggaca agtgaaagat ttctacctgt | 840 |
| atccaggaaa atatacatt gtcgaaaccg cagcaccaga cggttatgag gtagcaactg | 900 |
| ctattacctt tacagttaat gagcaaggtc aggttactgt aaatggctga | 950 |

```
<210> SEQ ID NO 108
<211> LENGTH: 38
<212> TYPE: PRT
<213> ORGANISM: Artificial
<220> FEATURE:
<223> OTHER INFORMATION: artificial polypeptide

<400> SEQUENCE: 108

Gly Ser Pro Glu Asp Lys Ile Ala Gln Leu Lys Glu Glu Asn Ala Gln
1               5                   10                  15

Leu Glu Gln Lys Asn Gln Gln Leu Lys Glu Glu Ile Ala Gln Leu Glu
            20                  25                  30

Tyr Gly Pro Gly Ser Gln
        35

<210> SEQ ID NO 109
<211> LENGTH: 37
<212> TYPE: PRT
<213> ORGANISM: Artificial
<220> FEATURE:
<223> OTHER INFORMATION: artificial polypeptide

<400> SEQUENCE: 109

Met Ser Pro Glu Asp Glu Ile Gln Ala Leu Glu Glu Lys Asn Ala Ala
1               5                   10                  15

Leu Lys Glu Glu Asn Ala Ala Leu Glu Glu Lys Ile Gln Ala Leu Lys
            20                  25                  30

Tyr Gly Pro Gly Ser
        35

<210> SEQ ID NO 110
<211> LENGTH: 38
<212> TYPE: PRT
<213> ORGANISM: Artificial
<220> FEATURE:
<223> OTHER INFORMATION: artificial polypeptide

<400> SEQUENCE: 110

Gly Ser Pro Glu Asp Lys Ile Ala Gln Leu Lys Glu Lys Asn Ala Ala
1               5                   10                  15

Leu Lys Glu Lys Asn Gln Gln Leu Glu Lys Ile Gln Ala Leu Lys
            20                  25                  30

Tyr Gly Pro Gly Ser Gln
        35

<210> SEQ ID NO 111
<211> LENGTH: 37
<212> TYPE: PRT
<213> ORGANISM: Artificial
<220> FEATURE:
<223> OTHER INFORMATION: artificial polypeptide

<400> SEQUENCE: 111

Met Ser Pro Glu Asp Glu Ile Gln Ala Leu Glu Glu Glu Asn Ala Gln
1               5                   10                  15

Leu Glu Gln Glu Asn Ala Ala Leu Glu Glu Ile Ala Gln Leu Glu
            20                  25                  30

Tyr Gly Pro Gly Ser
        35

<210> SEQ ID NO 112
<211> LENGTH: 38
<212> TYPE: PRT
```

```
<213> ORGANISM: Artificial
<220> FEATURE:
<223> OTHER INFORMATION: artificial polypeptide

<400> SEQUENCE: 112

Gly Ser Pro Glu Asp Lys Ile Ala Gln Leu Lys Gln Lys Ile Gln Ala
1               5                   10                  15

Leu Lys Gln Glu Asn Gln Gln Leu Glu Glu Asn Ala Ala Leu Glu
            20                  25                  30

Glu Gly Pro Gly Ser Gln
        35

<210> SEQ ID NO 113
<211> LENGTH: 37
<212> TYPE: PRT
<213> ORGANISM: Artificial
<220> FEATURE:
<223> OTHER INFORMATION: artificial polypeptide

<400> SEQUENCE: 113

Met Ser Pro Glu Asp Glu Ile Gln Gln Leu Glu Glu Glu Ile Ala Gln
1               5                   10                  15

Leu Glu Gln Lys Asn Ala Ala Leu Lys Glu Lys Asn Gln Ala Leu Lys
            20                  25                  30

Gln Gly Pro Gly Ser
        35

<210> SEQ ID NO 114
<211> LENGTH: 38
<212> TYPE: PRT
<213> ORGANISM: Artificial
<220> FEATURE:
<223> OTHER INFORMATION: artificial polypeptide

<400> SEQUENCE: 114

Gly Ser Pro Glu Asp Lys Ile Ala Gln Leu Lys Gln Glu Ile Ala Gln
1               5                   10                  15

Leu Glu Gln Glu Asn Gln Gln Leu Glu Lys Asn Gln Ala Leu Lys
            20                  25                  30

Gln Gly Pro Gly Ser Gln
        35

<210> SEQ ID NO 115
<211> LENGTH: 38
<212> TYPE: PRT
<213> ORGANISM: Artificial
<220> FEATURE:
<223> OTHER INFORMATION: artificial polypeptide

<400> SEQUENCE: 115

Met Ser Pro Glu Asp Glu Ile Gln Gln Leu Glu Glu Lys Ile Gln Ala
1               5                   10                  15

Leu Lys Gln Lys Asn Ala Ala Leu Lys Glu Glu Asn Ala Ala Leu
            20                  25                  30

Glu Glu Gly Pro Gly Ser
        35
```

SELF-ASSEMBLING PROTEIN SCAFFOLDS AND METHODS

CROSS-REFERENCE TO RELATED APPLICATION

This application is the § 371 U.S. National Stage of International Application No. PCT/US2018/043491, filed Jul. 24, 2018, which claims priority to U.S. Provisional Patent Application No. 62/536,650, filed Jul. 25, 2017, which is incorporated herein by reference in its entirety.

SEQUENCE LISTING

This application contains a Sequence Listing electronically submitted via EFS-Web to the United States Patent and Trademark Office as an ASCII text file entitled "2020-01-20-Sequence-Listing_ST25.txt" having a size of 85 kilobytes and created on Jan. 20, 2020. The information contained in the Sequence Listing is incorporated by reference herein.

GOVERNMENT FUNDING

This invention was made with government support under HR0011-17-2-0038 awarded by the Defense Advanced Research Projects Agency, HDTRA1-15-1-0004 awarded by the Defense Threat Reduction Agency, and MCB1264429 awarded by the National Science Foundation. The government has certain rights in the invention.

SUMMARY

This disclosure describes, in one aspect, a protein scaffold that includes a plurality of EutM subunits and a multi-enzyme cascade. The multi-enzyme cascade includes a first enzyme attached to the first EutM subunit and a second enzyme attached to the second EutM subunit. In some embodiments, the protein scaffold is self-assembled.

In some embodiments, the multi-enzyme cascade includes more than two enzymes. Each enzyme may be, independently of any other enzyme, covalently attached to a EutM subunit, ionically attached to a EutM subunit, attached to a EutM subunit through an affinity interaction.

In another aspect, this disclosure describes a method of forming a multi-enzyme protein scaffold. Generally, the method includes incubating a plurality of EutM subunits under conditions allowing the EutM subunits to self-assemble into a protein scaffold, attaching a first enzyme of a multi-enzyme cascade to a first EutM subunit, and attaching a second enzyme of the multi-enzyme cascade to a second EutM subunit.

The scaffold may be self-assembled in vivo or in vitro.

Each enzyme may be, independently of any other enzyme, attached to its EutM subunit in vivo or in vitro.

Each enzyme may be, independently of any other enzyme, attached to its EutM subunit before or after the scaffold is assembled.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 13. Designed orthogonal peptide pairs. Four pairs with four cognate interacting heptade blocks each, depicting all eight design heptade-heptade coiled-coil interactions (SEQ ID NOs: 108-115), are shown.

DETAILED DESCRIPTION OF ILLUSTRATIVE EMBODIMENTS

Figure 1:
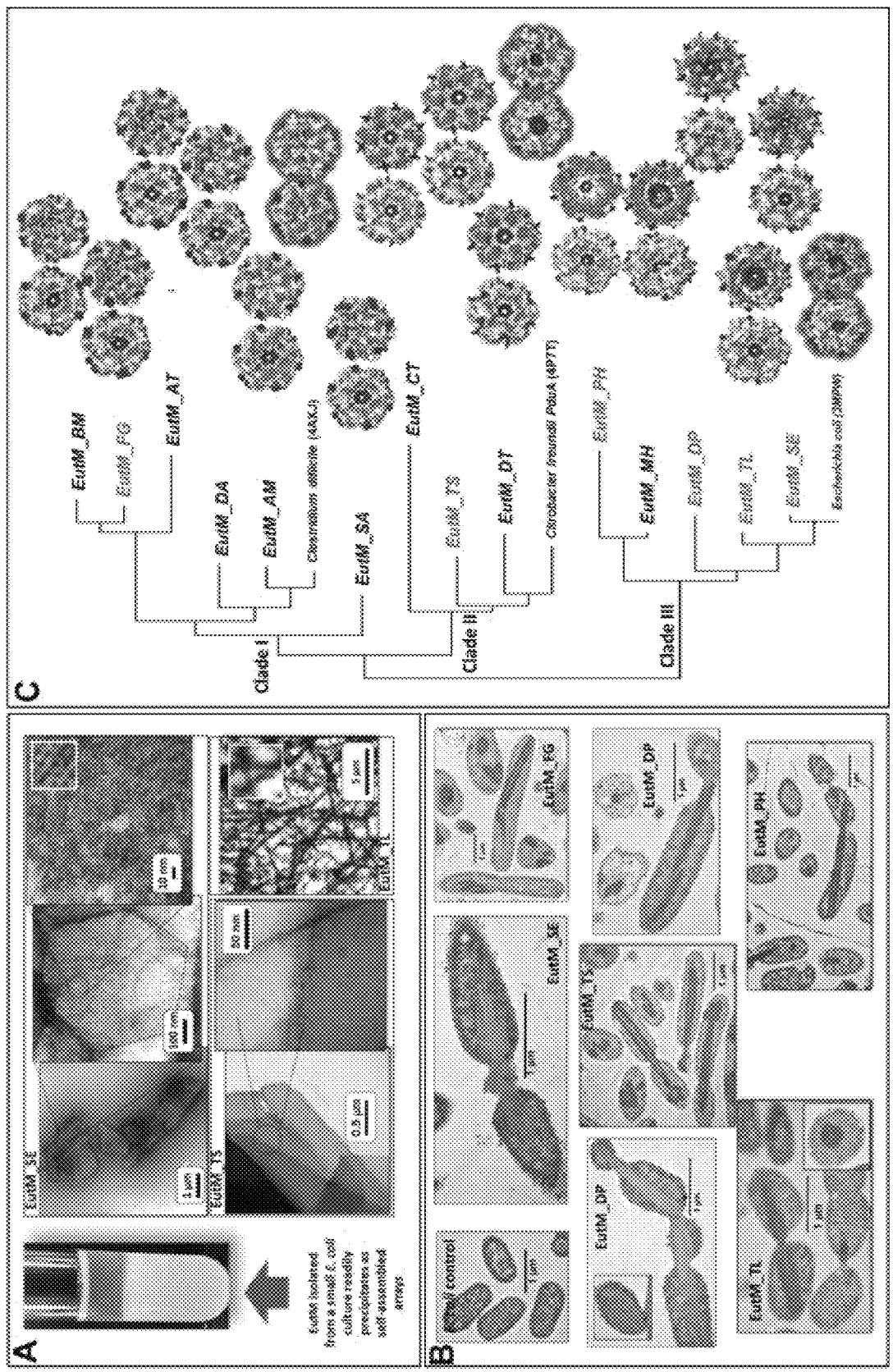
FIG. 1. EutM homologs self-assemble in vitro and in vivo. (A) His-tagged EutM homologs purified from small scale, recombinant E. coli cultures (see Table 1 for sequences) self-assemble different types of protein scaffolds as observed by TEM. Shown are three representatives (EutM_SE, EutM_TS, and EutM_TL). (B) Self-assembly and scaffold formation of EutM homologs can be readily observed in vivo when expressed in E. coli. TEM imaging of thin cell section of recombinant E. coli cells expressing different EutM homologs show the formation of ordered protein arrays that appear as tubes, rods or stacks. (C) EutM homologs selected for a EutM toolbox represent the microbial sequence diversity of EutM and include representatives for each of the three EutM homolog sequence clades. Models of EutM hexamers displayed as charged surface representations (red, negative and blue, positive). Shown are the top (cytosolic facing, left) and bottom (BMC lumen facing, right) sides. EutMs with structures are highlighted. Scaffold formation either in vivo or in vitro is shown in panels (A) and (B) for EutM homologs in red; confirming that EutM homologs from all three clades can self-assemble into higher ordered structures.

Multi-enzyme biocatalytic cascades represent an attractive and powerful approach to synthesis of valuable chemicals. Optimal reaction cascade efficiency requires spatial organization of the enzymes is necessary.

This disclosure describes an easy-to-adapt, genetically-encoded, and programmable self-assembling protein scaffolding system designed and built to be platform for the spatial co-localization of biocatalytic cascades. The developed platform exploits the self-assembling properties of the bacterial microcompartment shell protein EutM as scaffold building blocks, which was found to form robust, self-assembling protein arrays under a range of conditions suitable for biocatalysis. Further, N-terminal or C-terminal modifications of the EutM scaffold building block facilitate purification, facilitate cargo enzyme loading, and did not impede self-assembly.

A modular system was developed to facilitate rapid and easy covalent attachment of cargo enzymes to EutM protein arrays using SpyTag-SpyCatcher-mediated isopeptide formation. Different types of cargo proteins were successfully co-localized onto protein scaffolds in vitro (with isolated scaffold building blocks and cargo protein) and in vivo (by co-expression of scaffold building block and cargo protein in recombinant E. coli).

Moreover, an industrially-relevant dual-enzyme, self-sufficient cascade for chiral amine synthesis was co-localized onto the protein scaffolds and shown to significantly improve the reaction efficiency of this cascade compared to the soluble dual-enzyme cascade. This protein scaffold platform will therefore be broadly applicable for the spatial organization of other multi-enzyme cascades, which are key interest for industrial biomanufacturing processes for, for example, fine chemicals, pharmaceuticals, and chemical building blocks.

In addition, hundreds of uncharacterized EutM protein homologs were identified in sequence databases and, based on their protein sequences, were phylogenetically classified into three major clades. Twelve EutM homologs in addition to the initial EutM from Salmonella enterica (EutM_SE) were chosen for recombinant production and characterization to build a scaffold building block toolbox. These homologs, covering the sequence diversity of EutM homologs identified by bioinformatic analysis, were shown to self-assemble like the EutM_SE but also form different arrays and their hexamers differ in shape and surface charge distribution. The diversity of EutM homologs therefore provides access to a large toolbox of EutM building blocks for the creation of custom scaffolds tailored and optimized towards increasing the reaction of individual enzyme cascade reactions. By taking advantage of the diversity of EutM homologs, it will be possible to produce EutM scaffolds with diverse nano-architectures and physicochemical properties with optimal microenvironments for diverse multi-enzyme cascades.

This disclosure describes the design and building of a genetically programmable system for the spatial organization of multi-enzyme biocatalytic cascades. Self-assembling protein scaffolds were chosen as the basis for the development of such a system. Self-assembling protein scaffolds may offer one or more of the following properties: protein-based scaffolds can (1) be easily encoded (2) be adapted genetically for easy attachment in a manner that preserves enzyme catalyst activity, (3) facilitate catalyst recycling and product isolation, (4) be produced rapidly and at relatively low cost using a heterologous host or a cell-free production system, and/or (5) be robust enough to withstand reaction parameters and conditions dictated by industrial processes. Because microenvironments and proximity of catalysts are major determinants of cascade reaction efficiency, the chosen protein scaffold system has the potential of providing tunable microenvironments for catalysis in addition to co-localization of multiple catalysts. To engineer self-assembling scaffolds for multi-enzyme biocatalysis, the major shell protein EutM of the ethanolamine utilization (Eut) bacterial microcompartment from Salmonella enterica was used as basis scaffold building block. EutM is a 9.8 kDa protein that self-assembles into hexamers; the hexamers are believed to self-organize into extended arrays to form the facets of the outer shell of bacterial microcompartments.

Serendipitously, when heterologous EutM was expressed in E. coli cells using either a strong constitutive promotor or a strong inducible promoter, the E. coli cells formed a thick protein axial filament that spanned the length of cells and in some cases prevented correct cell division (FIG. 1B EutM_SE).

The EutM_SE protein was isolated from the recombinant E. coli cells to characterize its behavior in vitro. This His-tagged protein was purified by metal affinity chromatography from lysed E. coli cells. FIG. 1A shows the purified protein spontaneously self-assembles and begins to precipitate out of solution. TEM imaging of the formed precipitate shows that EutM_SE self-assembled as large crystalline arrays, with obvious hexameric organization and symmetry (FIG. 1A, EutM_SE). Importantly, protein arrays were able to withstand differences in pH and ionic strength without significant loss of array integrity, although the sub-organization of the hexameric symmetry became less apparent.

Figure 2:
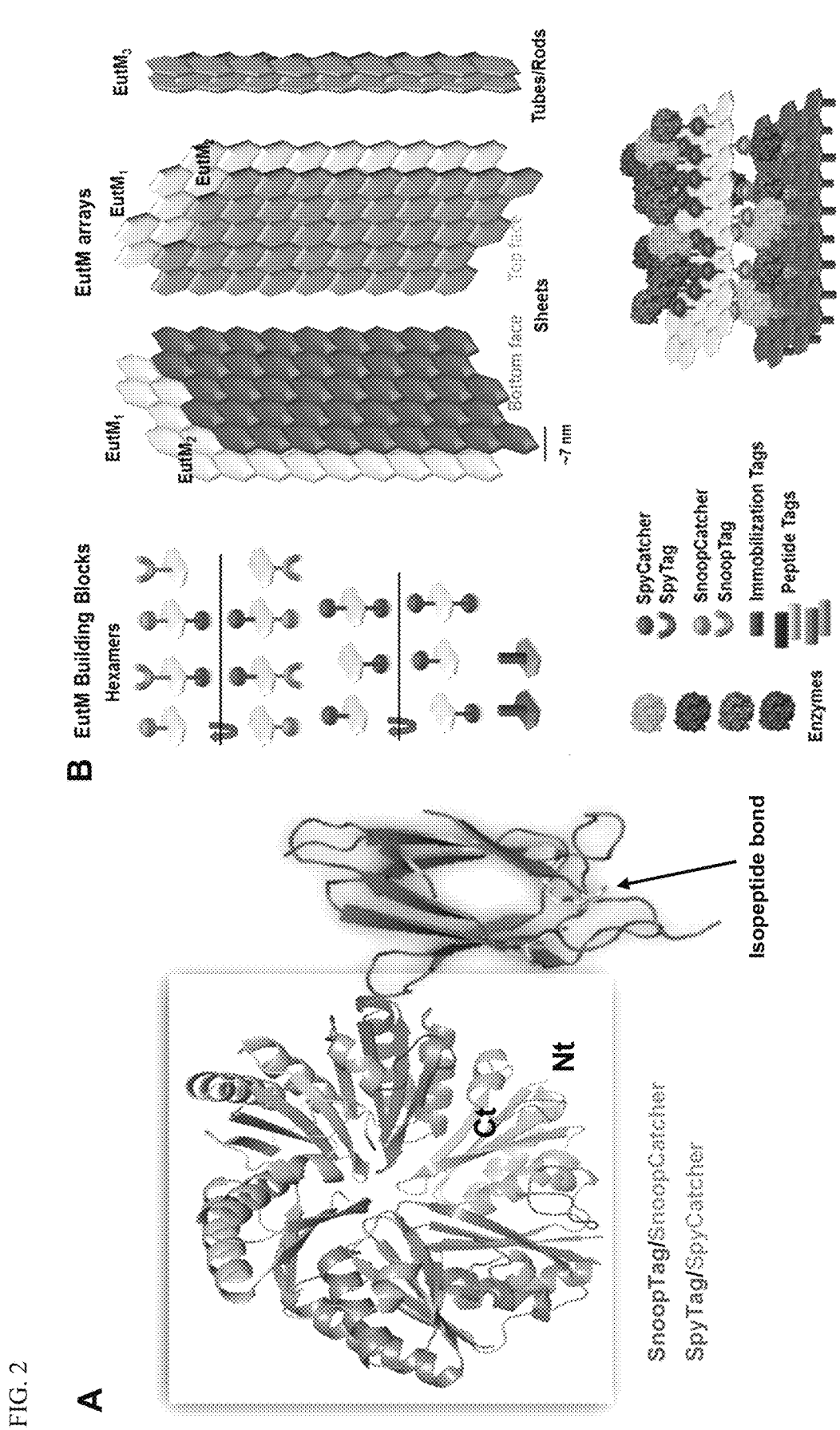
FIG. 2. Design of modular EutM protein scaffolds. (A) EutM building blocks can be modified with C-terminal or N-terminal Spy/SnoopTag or Spy/SnoopCatcher tags (or other modifications) to interact with a cognate interacting Spy/SnoopTag or Spy/SnoopCatcher tags (or other tag) displayed by the enzyme cargo protein. (B) Schematic of modular plug-and-play scaffold design and formation. Enzymes and capsids can be covalently linked to EutM arrays via differently configured EutM anchor points. Depending on the location of anchor points 2D or 3D-arrays may be formed. One possible design is shown.

EutM was therefore used as a model building block for the design of a protein-based scaffolding system for co-localizing multiple enzymes of a multi-enzyme cascade. By attaching enzymes as cargo to the EuM building blocks, one can spatially control the co-localization of enzymes onto the scaffolds. Different strategies (e.g., ionic, covalent, or affinity interacting peptide/protein tags attached to interacting protein partners, translational fusion of protein partners, chemical modification for attachment etc.) can be used to control the attachment of a cargo enzyme to EutM building blocks and thus the formed protein scaffolds (FIG. 2). As an initial example, covalent attachment via isopeptide bond formation was chosen. The possibility of, for example, non-covalent peptide-peptide interactions between EutM and cargo protein (displaying cognate orthogonal designer peptide pairs) as an alternative attachment method was also demonstrated.

For attachment of enzymes to the scaffolds, the genetically programmable SpyTag/SpyCatcher system (FIG. 2) (and its related SnoopTag/SnoopCatcher system; Veggiani et al., 2014. *Trends Biotechnol* 32(10):506-512) was chosen as initial attachment system. This system facilitates spontaneous and rapid covalent isopeptide bond formation. Using this technology should facilitate an easily adaptable, modular "plug-and-play" approach, enabling cargo loading on SpyCatcher-fused scaffolds in vivo or in vitro.

Figure 3:
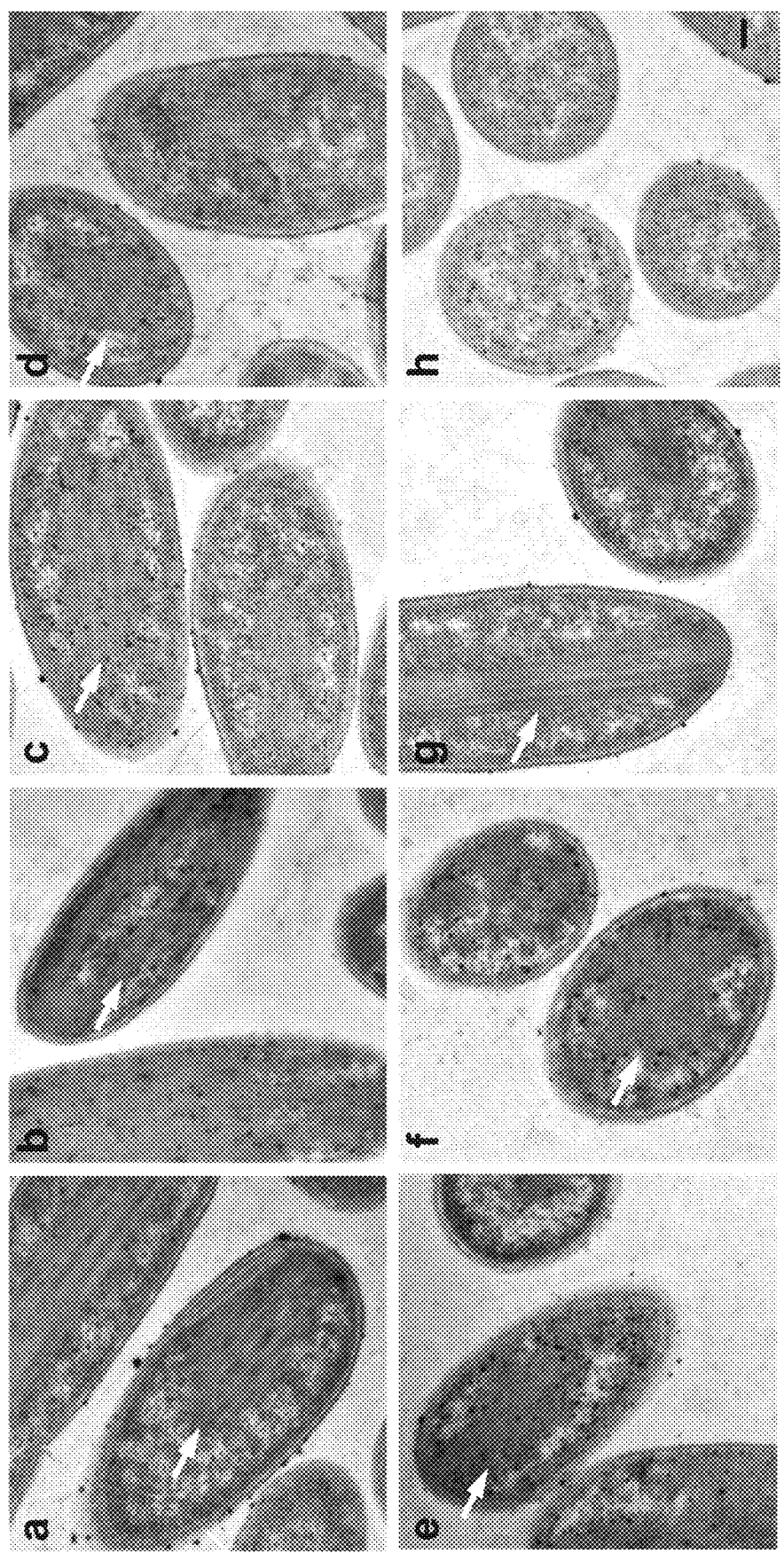
FIG. 3. Higher order structures formed upon expression of EutM or EutM-Spycatcher with SpyTagged eGFP in E. coli. Subcellular structures formed in E. coli C2566 observed by thin sectioning and TEM. Images are as follows: E. coli C2566 cells expressing (A) EutM+GFP, (B) EutM-Spycatcher+GFP, (C) EutM+SpyTag-GFP, (D) EutM+GFP-SpyTag, (E) EutM-Spycatcher+SpyTag-GFP, (F) EutM-Spycatcher+GFP-SpyTag, (G) EutM, (H) empty plasmid as a control. Bold arrowheads indicate scaffold-like structures. All images were taken at a magnification of 19,500×. The scale bar represents 100 nm.

To build a proto-type-scaffolding system, the SpyCatcher domain was fused to the C-terminus of N-terminally His-tagged EutM_SE to generate His-EutM-SpyCatcher. This SpyCatcher domain can then interact with a cognate SpyTag domain fused to a protein cargo such as an enzyme to form a covalent isopeptide bond. To test cargo protein attachment to the SpyCatcher-modified EutM scaffolding systems, the fluorescent reporter protein eGFP containing either a C-terminus or N-terminal SpyTag was chosen as enzyme proxy. Modifying the N-terminus or C-terminus of EutM and/or covalent binding of cargo protein may, however, interfere with the self-assembly of EutM and disrupt scaffold formation. Consequently, to affirm protein scaffold formation, His-tagged EutM_SE with or without C-terminal SpyCatcher domain was co-expressed in *E. coli* with unmodified or modified eGFP cargo protein containing either an N-terminal SpyTag or a C-terminal SpyTag. The two alternative eGFP SpyTag-configurations were chose for testing to ascertain that tags can be placed at either terminus of enzyme cargo as different enzymes may not tolerate modifications at one or the other terminus. The in vivo formation of higher order structures was then observed by thin cell section transmission electron microscopy (FIG. 3).

Interestingly, the EutM-SpyCatcher structures were not identical to those formed in cells expressing EutM (FIG. 1B). Rather than forming thick axial filaments, EutM-SpyCatcher formed shorter fibril-like structures that were aligned together in a less-well-ordered fashion, and did not appear to prevent cell division. It appears that the 9.5 kDa SpyCatcher fused to the C-terminus of EutM affects the self-assembly characteristics of the hexameric array, leading to the smaller scaffolds observed in vivo. Nonetheless, the ability of EutM to retain self-assembling capabilities even with a protein fusion of this size was remarkable and quite surprising. Furthermore, even more remarkable coexpression of EutM-SpyCatcher with both configurations of SpyTag fused GFP (29.2 kDa) as cargo had no effect on scaffold assembly, indicating that prefabrication of cargo-loaded scaffold in *E. coli* cells should therefore be possible. The ability to preload cargo can facilitate process scale-up, allowing for fewer unit operations.

Figure 4:
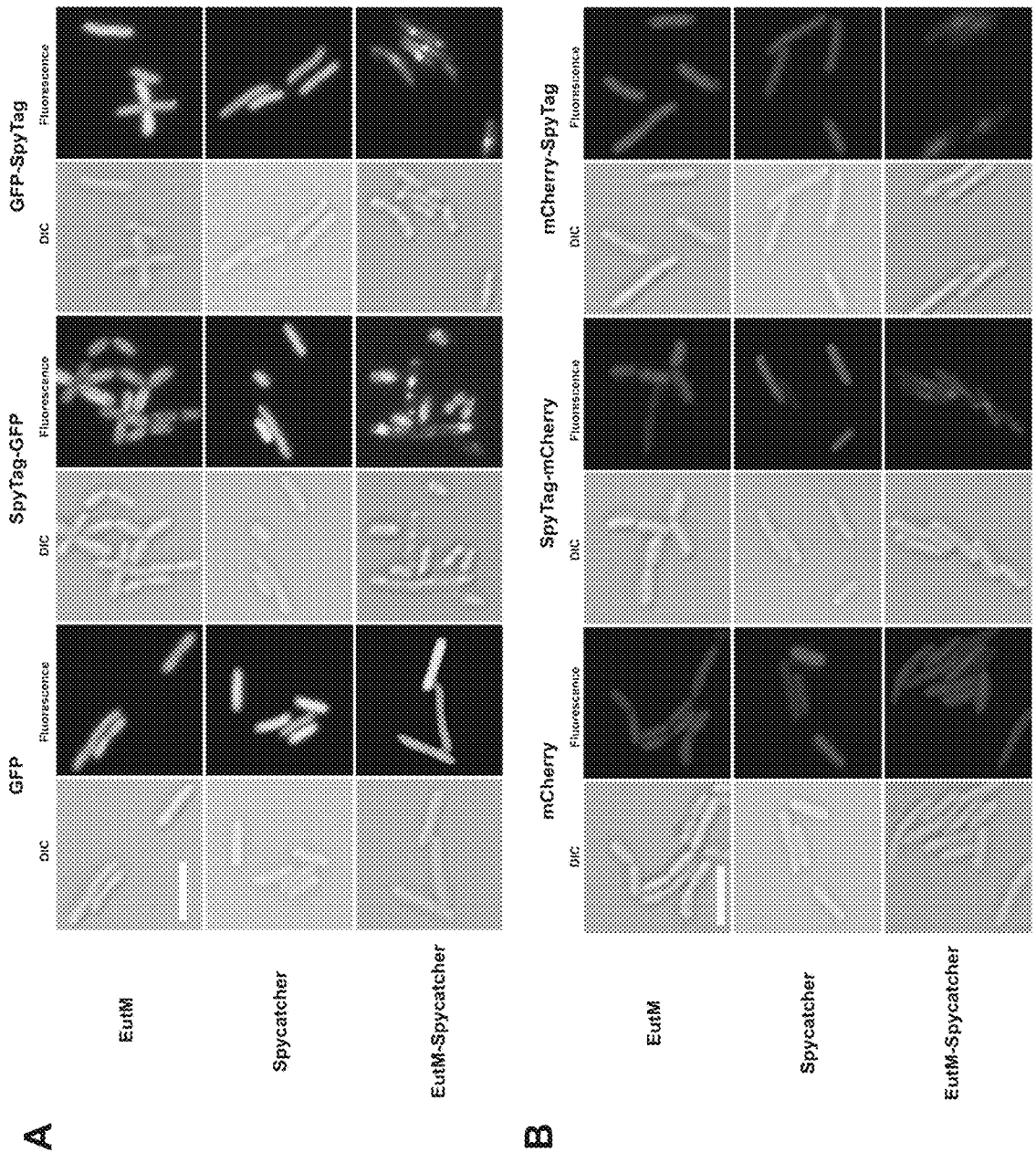
FIG. 4. SpyTag-fused fluorescent reporter cargo proteins are loaded onto EutM-SpyCatcher scaffolds. (A) Fluorescence microscopy of Spy-tagged (SpyTag-GFP, GFP-SpyTag) and untagged GFP co-expressed in E. coli with EutM-SpyCatcher and as a control with untagged EutM and SpyCatcher domain alone. (B) Fluorescence microscopy of the same set of experiments with mCherry as cargo protein. Images were taken at a magnification of 100× under oil. For all panels, differential interference contrast (DIC) images are shown to indicate cell boundaries. The scale bar represents 5 µm.

To confirm whether cargo was actually loaded on scaffolds in vivo, cells co-expressing EutM-SpyCatcher and SpyTag-GFP (in both configurations) were imaged by fluorescence microscopy. GFP localized as distinct fluorescent puncta within cells when targeted to EutM-SpyCatcher using SpyTag; in the absence of either SpyCatcher or SpyTag the GFP appeared diffuse in the cytoplasm of the cells (FIG. 4). This confirmed that cargo can be loaded on protein scaffolds in vivo. Notably, the localization pattern observed with the two different configurations of cargo was distinct, with SpyTag-GFP forming several spots and GFP-SpyTag forming a single punctum. This same phenomenum was observed when SpyTag labelled mCherry (as an alternative fluorescent reporter protein) was localized to EutM-SpyCatcher (FIG. 4), indicating that the configuration of the SpyTag-cargo fusion affects to an extend the availability of SpyTag to interact with SpyCatcher.

In Vitro Testing of the Scaffolding Platform

Figure 5:
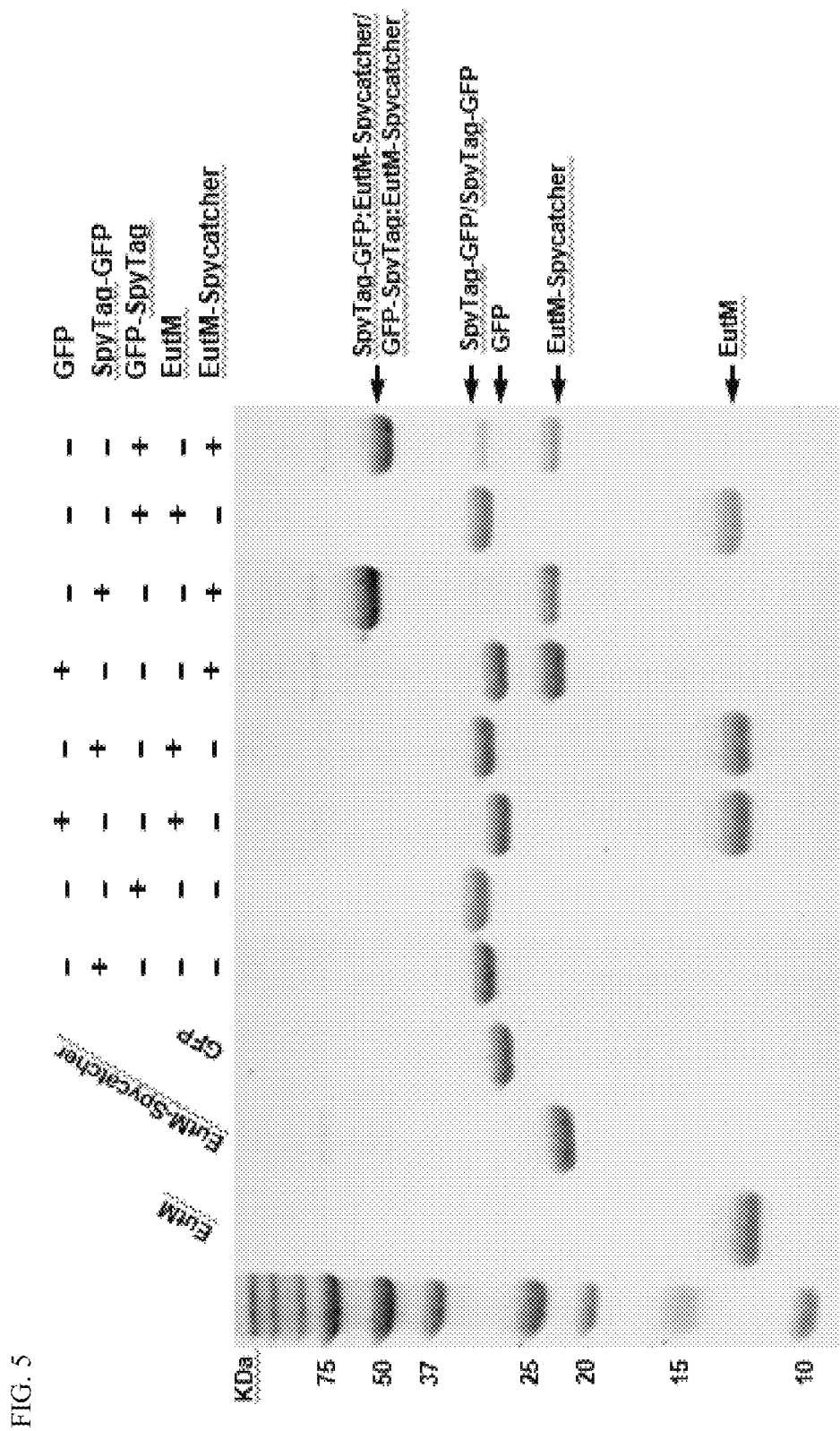
FIG. 5. Rapid in vitro covalent isopeptide bond formation between EutM-SpyCatcher and SpyTag GFP cargo protein. Purified proteins were mixed at a 1:1 molar ratio in combinations shown and covalent bond formation (resulting in the corresponding larger fusion protein) analyzed by SDS-PAGE. Control reactions with untagged proteins were also performed. Control proteins were included as size references and expected protein band sizes are labeled.

To determine whether there was any difference in the ability of N-terminally cargo or C-terminally cargo fused SpyTag to interact with EutM-SpyCatcher, isopeptide bond formation was confirmed in vitro by SDS-PAGE using purified proteins (FIG. 5). The reaction was surprisingly rapid, with bond formation initiated within a few seconds, and reaching completion within minutes. However, it was noted that the ability of GFP-SpyTag to form an isopeptide bond with EutM-SpyCatcher was slightly diminished in comparison to SpyTag-GFP (at a 1:1 molar ratio), which may be the result of steric hindrances caused by the different protein fusions.

Figure 6:
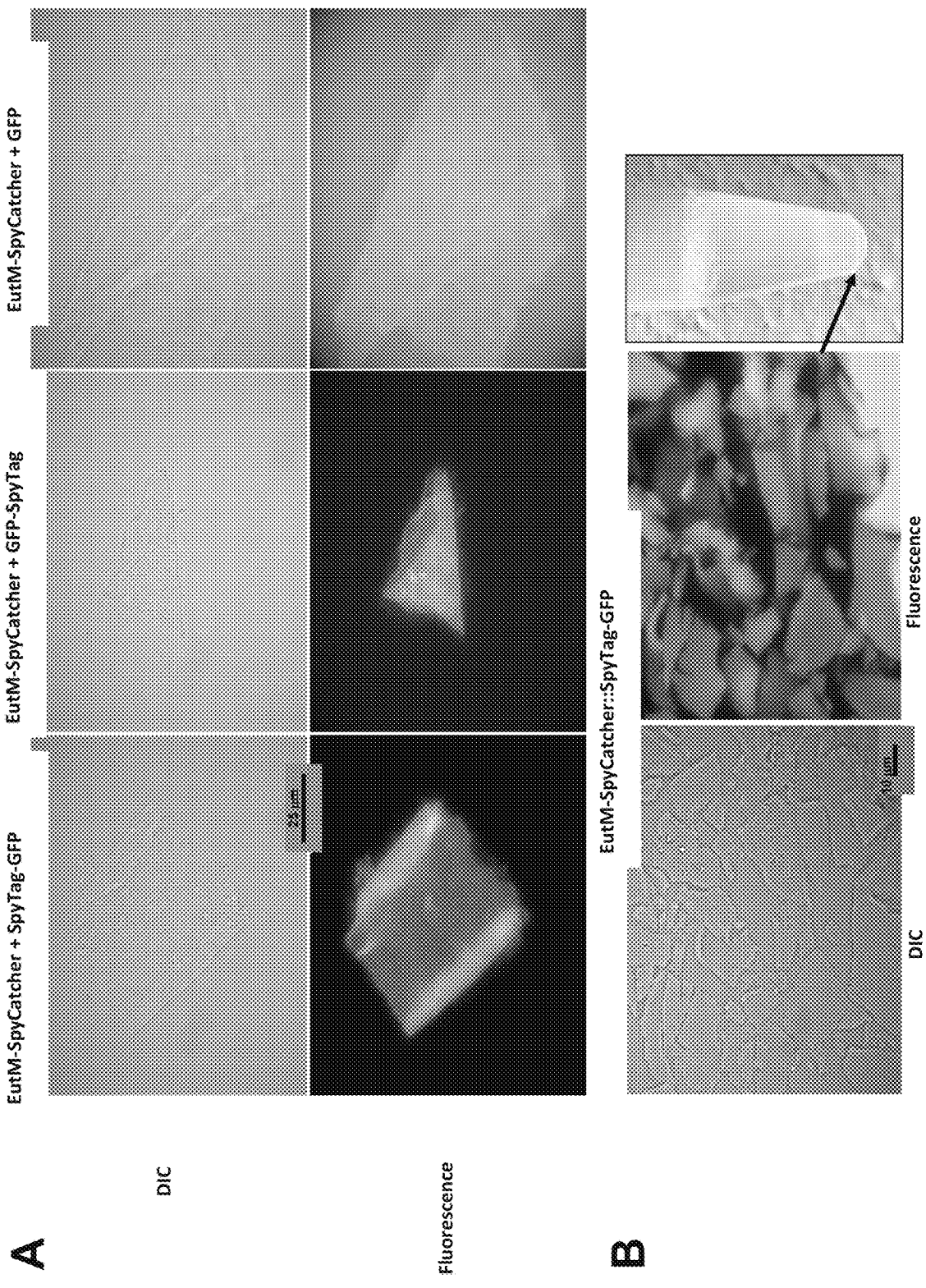
FIG. 6. EutM-SpyCatcher forms protein films/sheets. (A) Purified EutM-SpyCatcher was mixed at a 1:1 molar ratio with Spy-tagged GFP and untagged GFP as a control and observed by microscopy (DIC and fluorescence microscopy). SpyTagged GFP protein was efficiently localized onto the EutM scaffolds, while untagged GFP resulted in diffuse fluorescence. (B) Purified fusion protein of EutM-Spy-Catcher and SpyTag-GFP (EutM-SpyCatcher:: SpyTag-GFP) also forms sheets that precipitate out of solution.

When observed by light microscopy, purified EutM-SpyCatcher appears as thin films or sheets (>100 µm in length), which are in some cases folded over, indicating a flexibility in the large protein structure (FIG. 6A). GFP fused to SpyTag (in both alternative configurations) localized to the films, rendering the films fluorescent, confirming that the films contained SpyCatcher. Contrastingly, GFP without any SpyTag did not interact specifically with the EutM-SpyCatcher films, but remained in solution.

Following the confirmation that EutM-SpyCatcher forms thin films or sheets that can be readily observed by light-microscopy and that these sheets can be loaded with cargo protein, the next steps was to investigate whether cargo protein could potentially also be translationally fused to EutM building blocks without interfering with scaffold formation. A fusion protein was constructed where EutM-SpyCatcher was directly fused to SpyTag-GFP (EutM-SpyCatcher:: SpyTag-GFP), resulting in a EutM building block with a large (~40 kDa)C-terminal cargo appendix composed of the SpyCatcher domain followed by SpyTag-EGFP protein. Amazingly, despite this large appendix, EutM was still able to self-assemble into sheets (FIG. 6B), speaking to the robust self-assembly properties of the EutM building block. The ability to load cargo either on preformed EutM scaffolds or onto EutM building blocks via translational fusion will provide exceptional flexibility for catalyst localization onto this self-assembling protein scaffold system.

Figure 7:
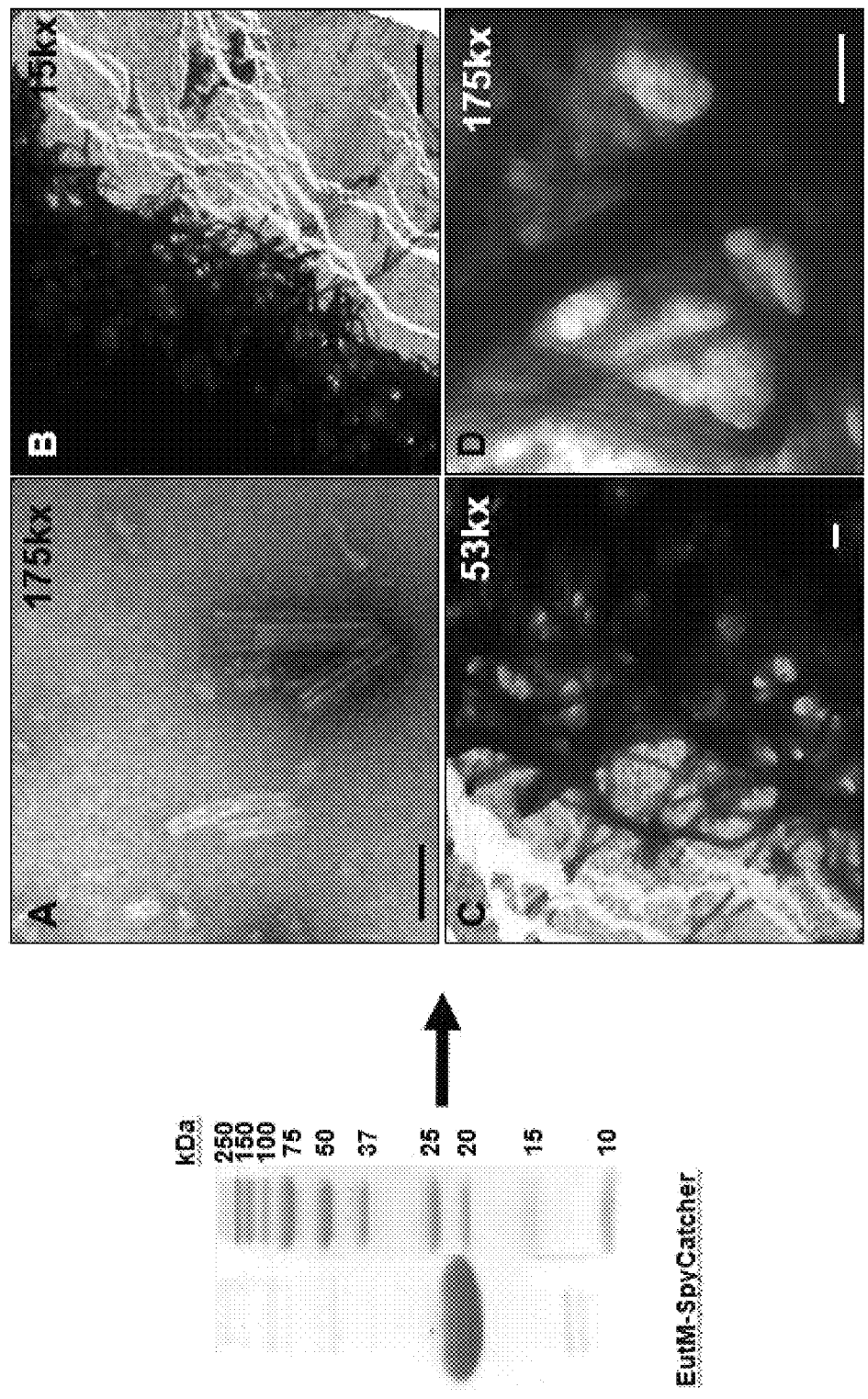
FIG. 7. EutM-SpyCatcher forms protein scaffolds composed of protein fibrils. (A) TEM analysis of purified EutM-SpyCatcher (1.5 mg mL$^{-1}$, pH 7.5) shows the formation of rod-like structures when no fixative is applied. (B-D) TEM analysis of purified EutM-SpyCatcher (1.5 mg mL$^{-1}$, pH 7.5) shows the formation of larger, self-organized structures made up of the same types of rods when a fixative was used. Images were taken at a magnification of 15,000×-175,000×. The scale bars represent 100 nm.
Figure 16:
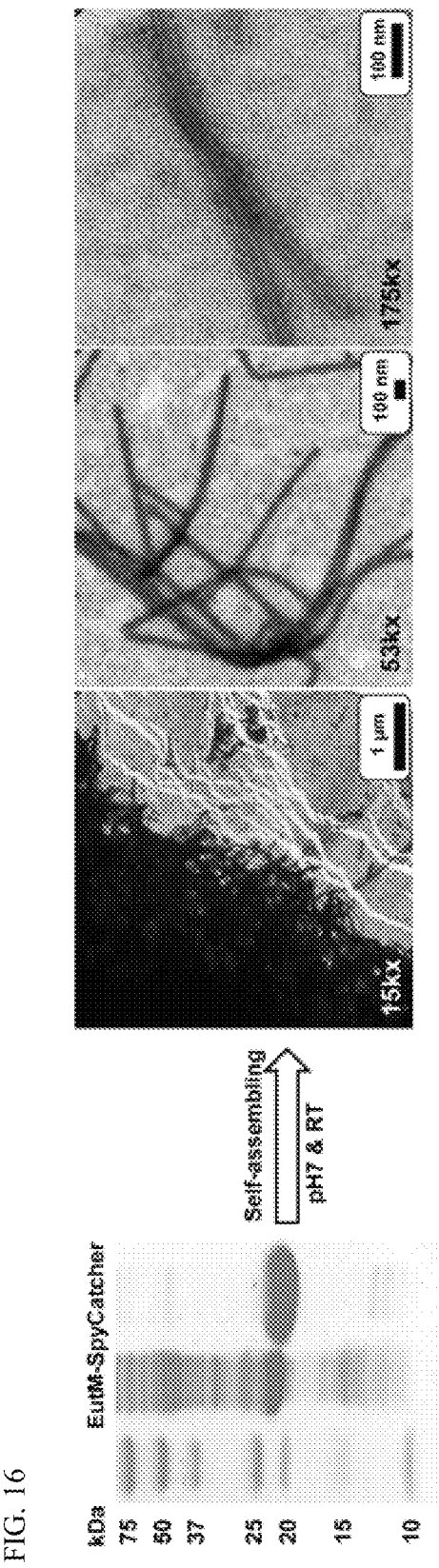
FIG. 16. EutM-SpyCatcher scaffolds and SpyTag-cargo loading in vitro. His-tagged EutM-SpyCatcher (2 mg mL$^{-1}$, 1x PBS pH 7.4) purified from E. coli forms arrays of protein fibrils visualized by negative stain TEM.

To confirm that that the self-assembled EutM-SpyCatcher films observed by light microscopy were protein scaffolds, these structures were visualized by negative stain Transmission Electron Microscopy (TEM). Rather than forming the rigid, hexameric arrays formed by EutM (FIG. 1), EutM-SpyCatcher forms large scaffolds made up of long, flexible protein fibrils or rods (FIG. 7, FIG. 16). This finding corroborates observations made in recombinant *E. coli* cells expressing EutM-SpyCatcher (FIG. 3, FIG. 4), which appeared to form structures made of shorter, rod-like filaments as opposed of the long axial filaments seen with EutM (FIG. 3).

Figure 8:
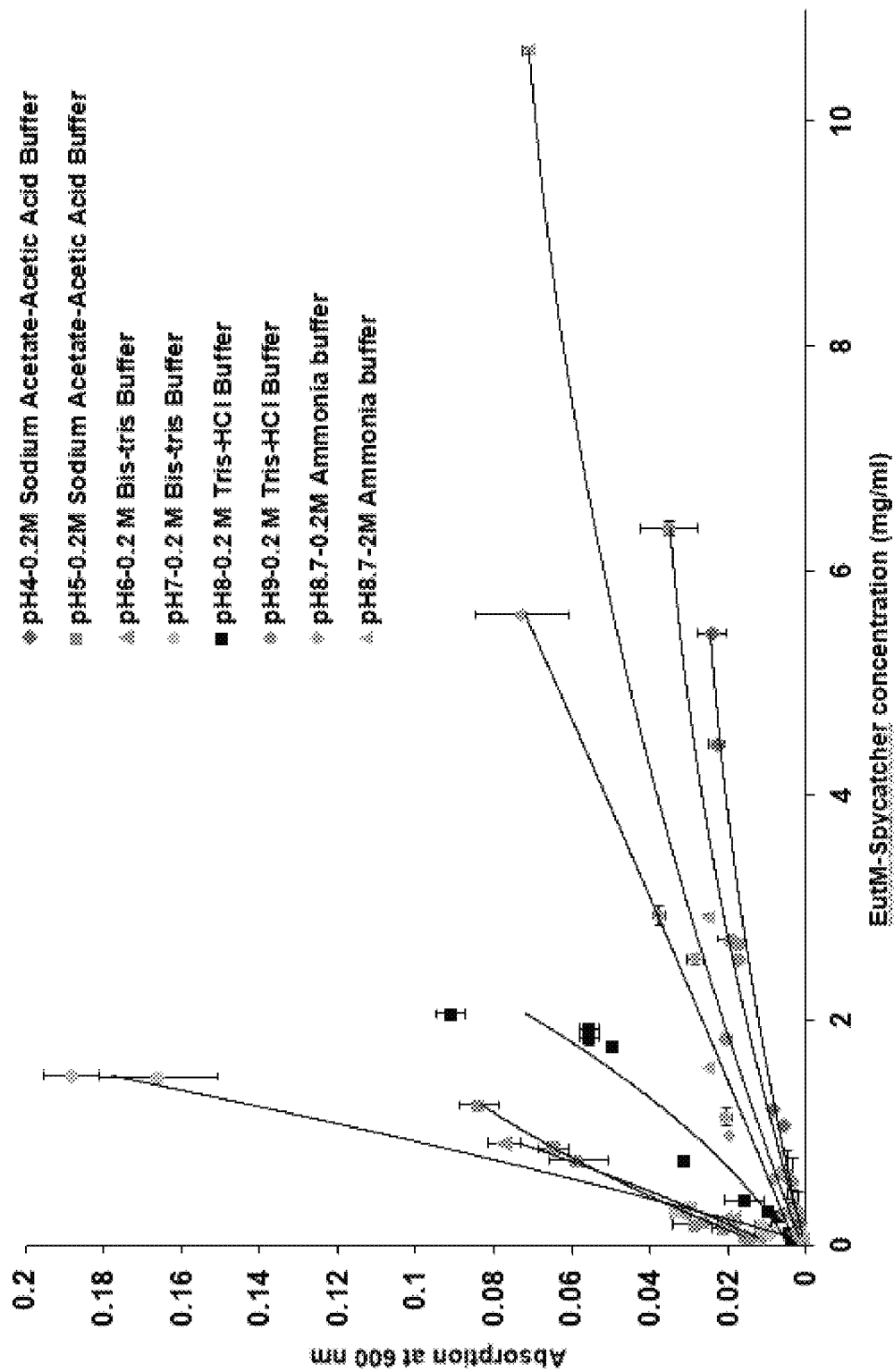
FIG. 8. EutM-SpyCatcher scaffold formation under different buffer conditions. Purified and soluble EutM-SpyCatcher was concentrated to different protein concentrations and absorption at 600 nm was monitored to follow scaffold formation. Absorption at 600 nm ("cloudiness") increases with protein concentration in a buffer dependent manner. Under all conditions tested, scaffolds formed; although under some conditions more readily than under others.

To demonstrate robustness and applicability of the EutM scaffolds for enzyme co-localization under conditions relevant for biocatalysis, scaffold formation with purified EutM-SpyCatcher was tested under a range of buffer conditions typically used for enzyme reactions. Scaffold formation was measured by monitoring the increase in absorption at 600 nm at different pH and protein concentrations (FIG. 8). Scaffolds formed at a wide range of pH, in a protein concentration dependent manner (see also FIG. 7, scaffolds formed at pH 7 and 1.5 mg mL$^{-1}$ EutM-SpyCatcher). Scaffolds formed most readily in buffer Bis-Tris pH 7 by requiring the lowest protein concentration for EutM-SpyCatcher self-assembly. However, scaffolds also formed under low and high pH conditions and surprisingly even under more extreme pH conditions such as in pH 4 and pH 9 buffers. Scaffold formation was also achieved at a high ammonia concentration (2M) and pH (pH 8.7), reaction conditions required for a dual enzyme cascade chosen below as a model system to test the utility of the protein scaffolds for biocatalysis.

Co-Localizing Enzymes of a Multi-Enzyme Cascade

Figure 9:
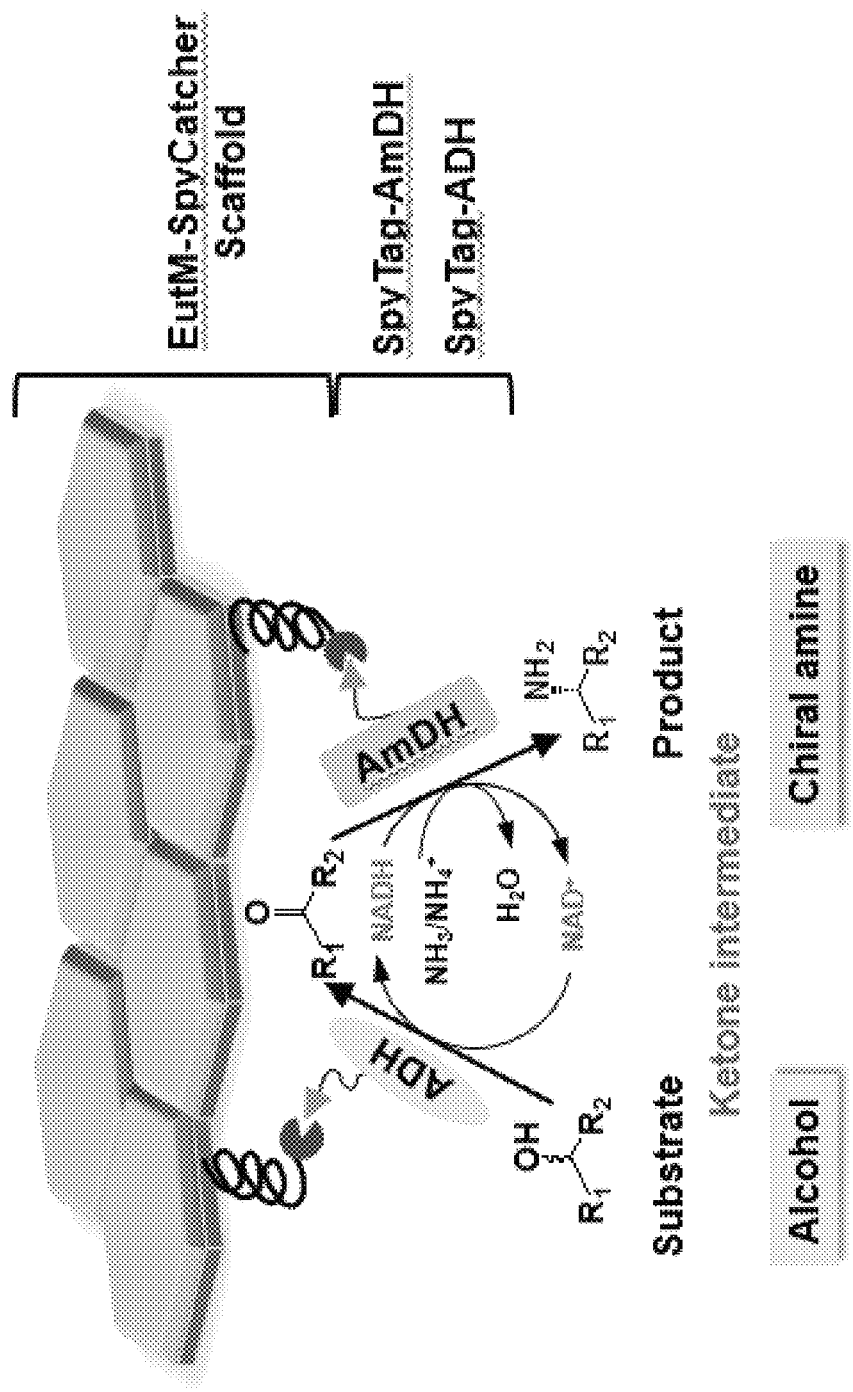
FIG. 9. Co-localization of a self-sufficient hydrogen borrowing dual enzyme cascade for chiral amine synthesis. Amine dehydrogenase (AmDH: Ch1-AmDH a chimera of the N-terminal substrate binding region of Bacillus badius PheDH and C-terminal NADH domain of Bacillus stearothermophilus LeuDH) and alcohol dehydrogenase (ADH: AA-ADH from Aromatoleum aromaticum) are fused with a SpyTag for co-localization onto EutM-SpyCatcher scaffolds. The alcohol substrate is converted via a ketone intermediate into a chiral amine under concurrent NAD$^+$/NADH cofactor cycling.

After characterizing and confirming scaffold formation and cargo loading to the designed EutM protein scaffolding system, the developed platform was tested with an industrially relevant exemplary enzyme cascade reaction to find out if enzyme co-localization on EutM scaffolds improves the efficiency of biocatalytic reaction systems. A self-sufficient hydrogen borrowing dual enzyme cascade for chiral amine synthesis was selected for this exemplary test (FIG. 9). The chosen co-factor-recycling cascade reaction was recently designed and demonstrated as a one-pot system with soluble enzymes. This particular biocatalytic reaction is of interest for industrial applications, but significant optimization and/or reaction efficiency is needed to develop a commercially viable process; complete substrate conversion of the soluble system as published required a reaction time of 48 hours. In this system, an NADtdependent alcohol dehydrogenase (ADH) and an NADH-dependent-amine-dehydrogenase (AmDH) are combined to convert alcohols to amines in a highly enantioselective manner. Because the two enzymes catalyze redox opposite reactions, this cascade is self-sufficient, using ammonium ion/ammonia in the buffer to regenerate the cofactor.

Figure 17:
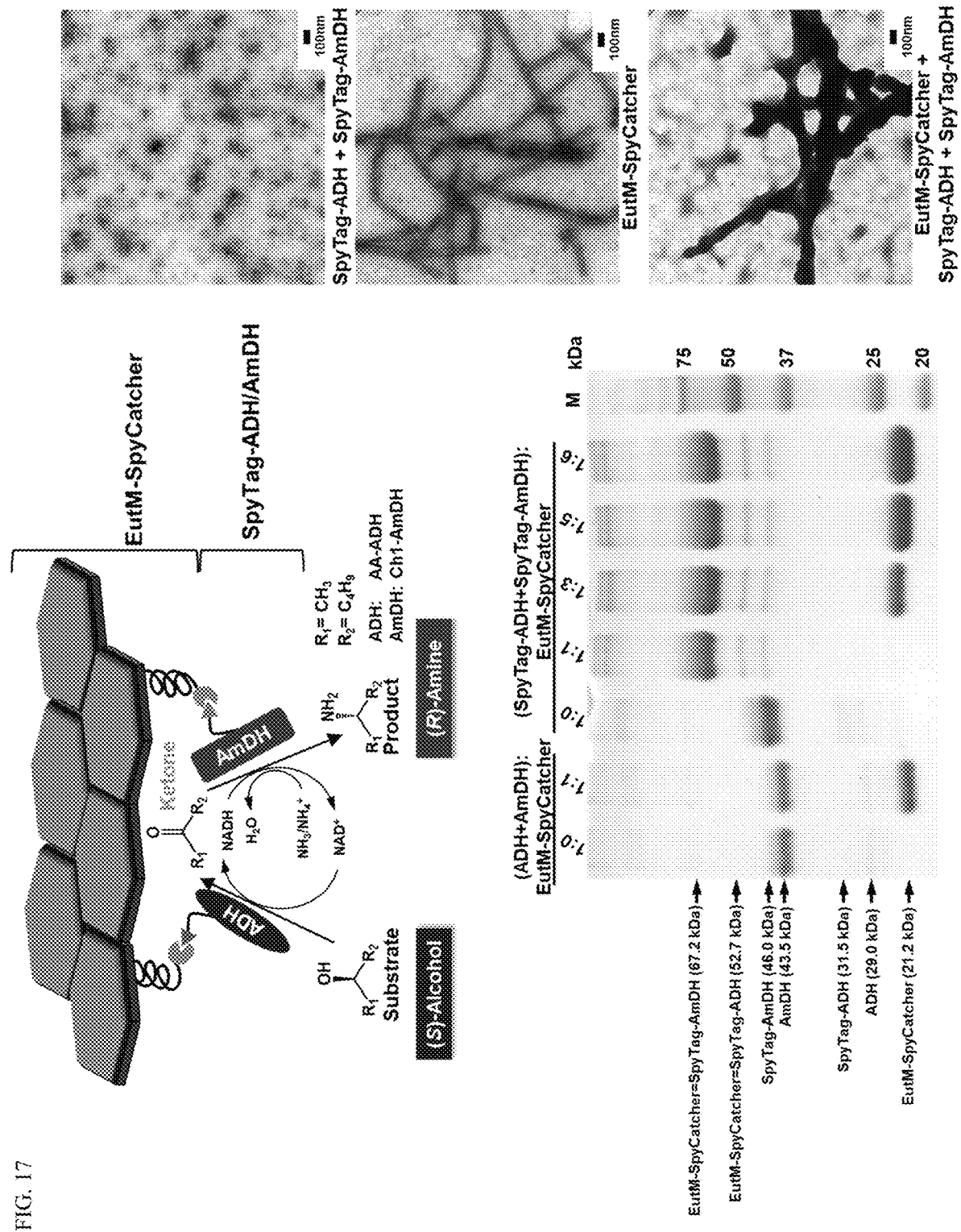
FIG. 17. Co-immobilization of a dual enzyme cascade for chiral amine synthesis. (A) Schematic of dual enzyme cascade co-immobilized on EutM-SpyCatcher protein scaffolds. An alcohol dehydrogenase (ADH) oxidizes an alcohol substrate into the corresponding ketone intermediate that is subsequently reduced by an amine dehydrogenase (AmDH) into a chiral amine. In this study, a Prelog AA-ADH with broad substrate specificity was combined with an engineered, stable chimeric Ch11-AmDH for the conversion (S)-2-hexanol to (R)-2-aminohexane. (B) SDS-PAGE analysis confirms enzyme cargo loading to EutM-SpyCatcher scaffolds under amination reaction conditions (2 M ammonium chloride buffer, pH 8.7) prior to co-factor and substrate additions. Enzyme cascades (SpyTag fused ADH (6 µM) and AmDH (150 µM)) were mixed at different molar ratios with EutM-SpyCatcher. Corresponding control reactions were performed with untagged enzymes. "=" represents the isopeptide formed between SpyTag and SpyCatcher. (C) Visualization of the enzyme-loaded scaffolds under amination reaction conditions by negative stain TEM. Top: free enzyme cascade of SpyTag-ADH (6 µM) and SpyTag-AmDH (150 µM); middle: EutM-SpyCatcher (780 µM) forms fibril-like scaffolds; bottom: large structures are formed by (SpyTag-ADH+SpyTag-AmDH):EutM-SpyCatcher scaffolds at 1:5 ratio. All images were taken at a magnification of 53,000×. The scale bars represent 100 nm.

Prelog AA-ADH (53) (referred to as ADH; Hoffken et al., 2006 *Biochemistry* 45:82-93) with broad substrate specificity, and a stability engineered chimeric Ch1-AmDH (Fu et al., 2012. *J Am Chem Soc* 134:5516-5519) (referred to as AmDH) for co-immobilization on EutM-SpyCatcher scaffolds. As a model reaction, the conversion of (S)-2-hexanol to (R)-2-aminohexane was chosen because substrate and reaction products are commercially available, and the conversion was shown to be catalyzed by the two enzymes in 48 hrs with 95% efficiency and >99% enantiomeric excess (ee) to the R-amine (FIG. 17A).

Figure 10:
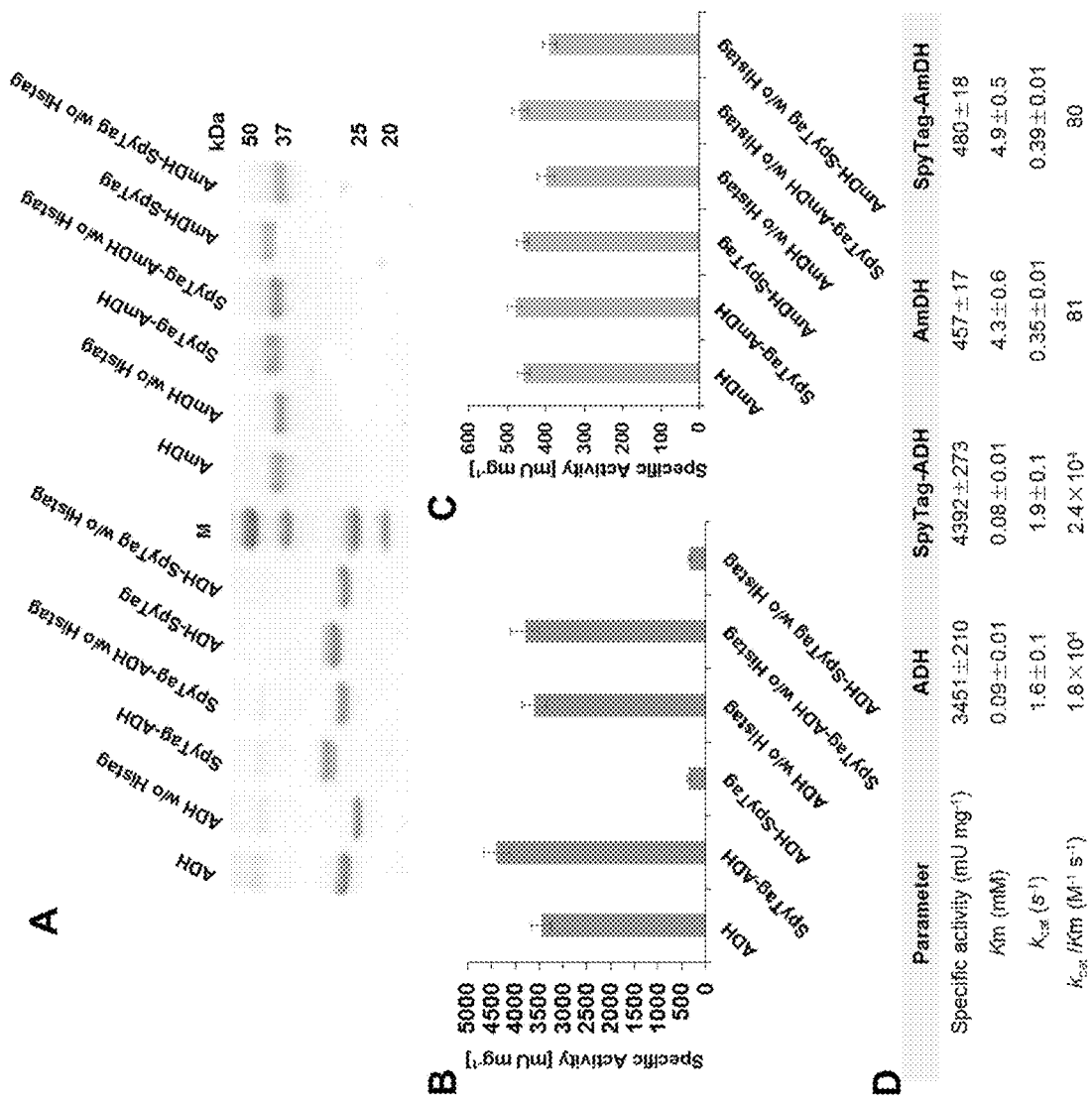
FIG. 10. Enzymatic activities of ADH and AmDH containing a N-terminal or C-terminal SpyTag with untagged enzymes. (A) SDS-PAGE analysis of purified, N-terminally His-tagged ADH and AmDH enzymes fused to an N-terminal SpyTag or C-terminal SpyTag and the same enzymes with the His-tag removed (w/o Histag) by thrombin cleavage. (B) Effect of His-tag and SpyTag on the specific activities (mU mg-1 of protein) of the purified ADH enzyme shown in (A). (C) Effect of His-tag and SpyTag on the specific activities (mU mg-1 of protein) of the purified AmDH enzyme shown in (A). (D) Kinetic properties of ADH and AmDH compared to SpyTag fused enzymes under amination reaction conditions. Enzyme activities were measured with (S)-(+)-2-hexanol and hexanone as substrates for ADH and AmDH, respectively, by monitoring the increase or decrease of NADH at 340 nm.

Because EutM-SpyCatcher scaffolds form under a broad range of reaction conditions, including the high pH and ammonia concentration necessary for the ADH and AmDH hydrogen borrowing enzyme cascade, the next important step was to test whether the two enzymes tolerate a SpyTag fusion without compromising enzyme activity. The SpyTag was fused either to the C-terminus or N-terminus and the specific activity of the purified tagged and untagged enzymes was measured with their respective substrates. AmDH tolerated the SpyTag at either terminus, while ADH only retained activity with an N-terminal SpyTag fusion. The kinetic parameters of the N-terminal Spy-tagged ADH and both Spy-tagged configurations of AmDH are comparable to the untagged enzyme (FIG. 10).

Figure 11:
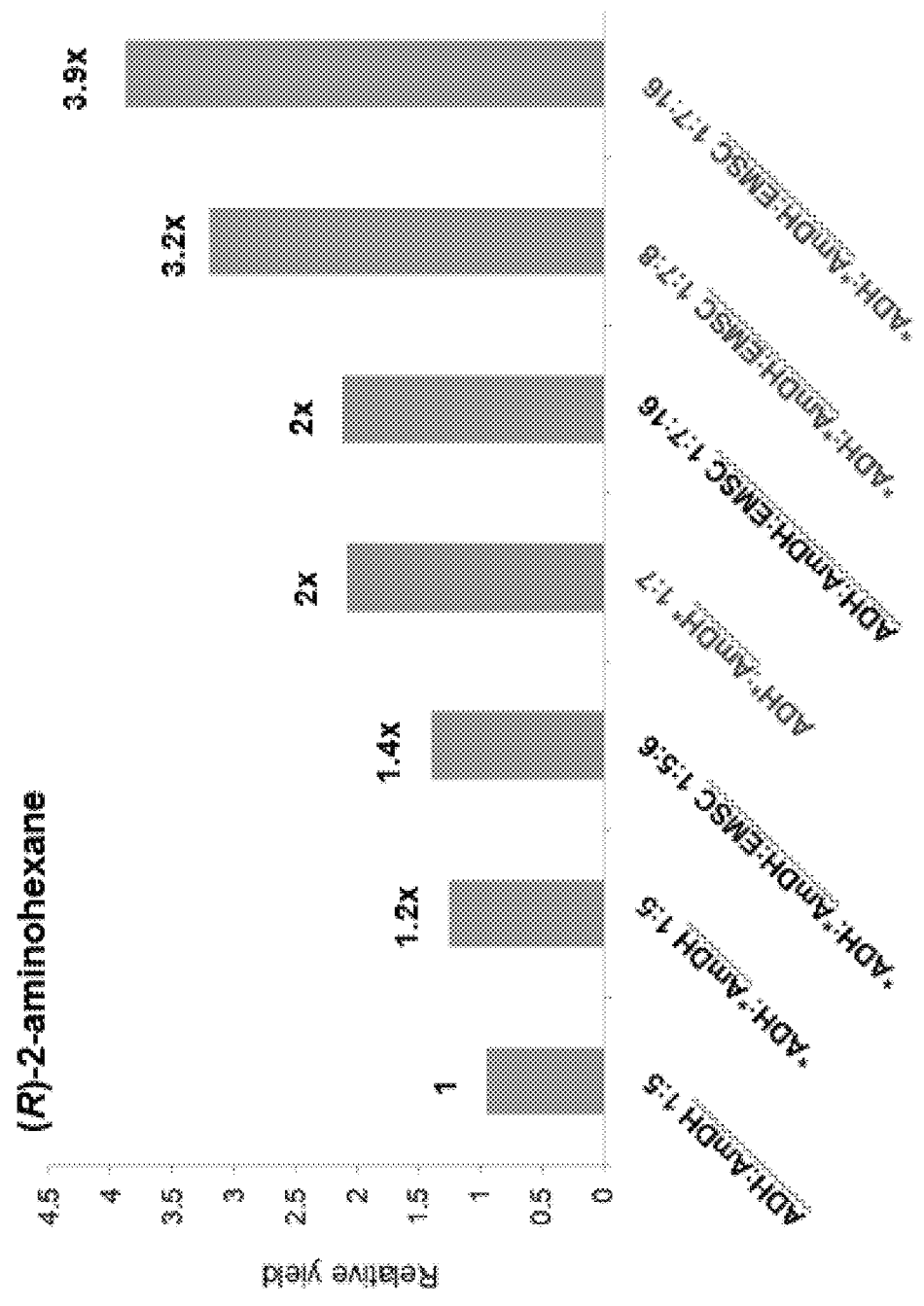
FIG. 11. Comparison of cascade performance with soluble and co-localized ADH and AmDH. Conversion of 20 mM (S)-(+)-2-hexanol to (R)-2-aminohexane after 12 hrs of reaction time with soluble and EutM-SpyCatcher co-localized SpyTag-ADH and SpyTag-AmDH (Asterisks indicates SpyTag). Enzymes and EutM were mixed at a range of molar ratios. Controls were performed with untagged ADH and AmDH.

One-pot dual enzyme cascade reactions were set up with purified, recombinant ADH and AmDH with SpyTags for comparison with a co-localized cascade reaction. Based on the enzyme activity data, ADH was identified as the faster acting enzyme with a higher Vmax and higher affinity for its substrate compared to AmDH (FIG. 10). Consequently, AmDH is expected to be the rate limiting enzyme in the cascade, having an approximately five-fold lower specific activity than ADH. Initial experiments were therefore performed with a 1:5 molar ratio of ADH:AmDH and the product yield of the untagged, soluble cascade reaction set as 1. The SpyTagged enzymes at the same molar ratio gave slightly higher yields. Addition of preformed EutM-SpyCatcher scaffolds at a molar ratio of the combined molar ratios of the two enzymes increased the yield by ~10-15% (FIG. 11). Figuring that AmDH may still be rate limiting in the dual enzyme cascade conditions, the ADH:AmDH molar ratio was increased to 1:7, resulting in a doubling of the product yield of the soluble enzyme cascade (FIG. 11). The addition of preformed EutM-SpyCatcher scaffolds to this enzyme cascade reaction using a 1:7:8 ratio of SpyTag-AA-ADH: SpyTag-Chl-AmDH:EutM-SpyCatcher (1:1 ratio of Spy-tagged enzymes to SpyCatcher scaffolds) now significantly increased cascade performance 3.2-fold. Altering this ratio to 1:7:16 to increase spacing of enzymes on the protein scaffold further increased relative yields to almost four-fold greater than the initial non-scaffolded system (FIG. 11).

Figure 12:
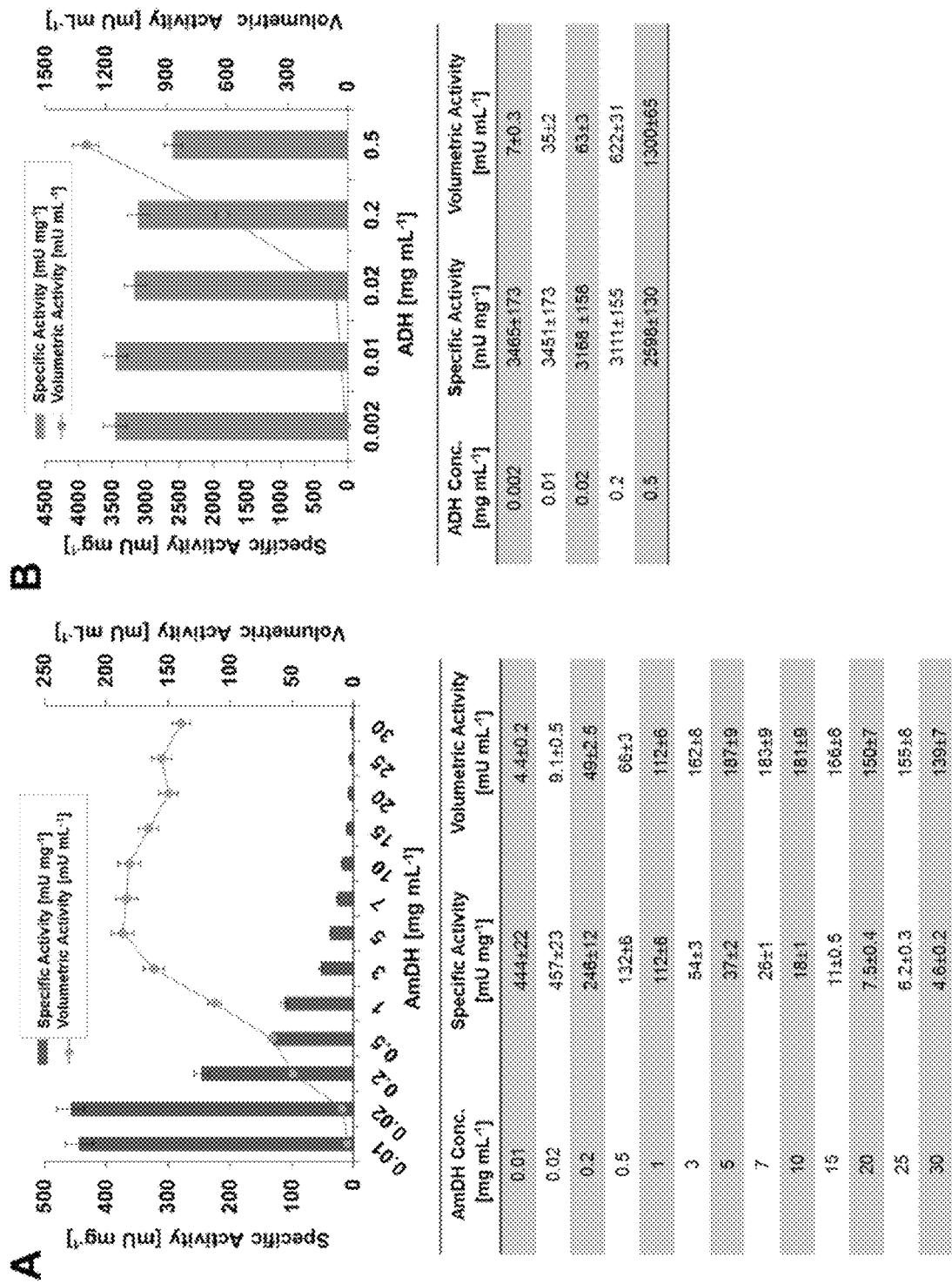
FIG. 12. (A) Specific and volumetric activities of purified AmDH measured with different protein concentrations. (B) Specific and volumetric activities of purified ADH measured with different protein concentrations. Activities of purified His-tagged enzymes were determined using a UV-microplate reader by monitoring the change of NADH concentration at 340 nm ($\varepsilon$=6.22 mM$^{-1}$ cm$^{-1}$) in 2 M ammonium chloride buffer (pH 8.7) for 3 mins at room temperature.

Balancing the lower activity and higher $K_m$ of AmDH with the significantly more active ADH in a cascade reaction would therefore require a higher protein concentration of AmDH compared to ADH. To identify optimal amounts of enzyme for cascade reactions, the volumetric and specific activities of AmDH and ADH in amination buffer at different protein concentrations were measured (FIG. 12). The specific activity of AmDH was strongly dependent on protein concentration (potentially due to the formation of soluble aggregates), decreasing from 457 mU mg$^{-1}$ at a protein concentration of 0.02 mg mL$^{-1}$, to 246 mU mg$^{-1}$ at a protein concentration of 0.2 mg mL$^{-1}$, and decreasing further to 37 mU mg$^{-1}$ at a protein concentration of 5 mg mL$^{-1}$. A concentration of approximately 5-7 mg mL$^{-1}$ of AmDH therefore afforded the best volumetric activity, as such 150 µM (185 mU mL$^{-1}$, 7.4 mg mL$^{-1}$) AmDH was subsequently used in all cascade reactions. To balance the cascade, ADH was added at a concentration of 6 (0.2 mg mL$^{-1}$) to all cascade reactions. This resulted in a 3.5-fold higher total activity (650 mU mL$^{-1}$) of ADH compared to AmDH (185 mU mL$^{-1}$) (FIG. 12).

Finally, isopeptide bond formation under amination reaction conditions was confirmed by mixing EutM-SpyCatcher with SpyTag fused enzymes (and untagged enzymes as a control) at the identified concentrations (6 µM (0.2 mg mL$^{-1}$) for SpyTag-ADH and 150 µM (7.4 mg mL$^{-1}$) for SpyTag-AmDH. Assuming that enzyme distribution on scaffolds would influence cascade efficiency, different molar ratios of enzyme mixture to scaffold were tested (FIG. 17B). As seen with GFP (FIG. 5), isopeptide bond formation proceeded rapidly; at a 1:1 molar ratio (calculated based on measured protein concentrations) all EutM-SpyCatcher was converted into higher molecular weight complexes as detectable by SDS-PAGE analysis. With increasing molar ratios of EutM-SpyCatcher in the mixtures, proportional amounts of EutM-SpyCatcher remained unmodified. A small amount of SpyTag-AmDH remained unbound, even when EutM-Spy-Catcher was present in excess, suggesting that a small portion of SpyTag-AmDH does not display a tag that is conformationally accessible for interaction with the Spy-Catcher domain.

Negative stain TEM of the enzymes immobilized on the scaffolds showed that the attachment of SpyTag fused enzymes to EutM-SpyCatcher resulted in a dense film-like material covering the fibril-like EutM-SpyCatcher scaffolds (FIG. 17C, bottom panel: note that enzyme-immobilized scaffolds appear thicker and more darkly stained than scaffolds lacking enzymes, middle panel). No scaffold-like structures or amorphous aggregates were observed in the enzyme only control. This change in scaffold morphology when loaded with enzymes ADH and AmDH is in contrast to GFP loading on scaffolds, which did not change the appearance of EutM-SpyCatcher and must relate to the properties of the enzymes. ADH is a homotetramer (PDB: 2EW8, 2EWM) (53), while AmDH might associate as a homodimer based on its sequence similarity to PheDH from Rhodococcus sp. M4 (PDB: 1BW9, 1C1D). The quaternary structures of the enzymes and potential multipoint attachment of these multimeric complexes may be responsible for the observed altered scaffold morphology.

Figure 18:
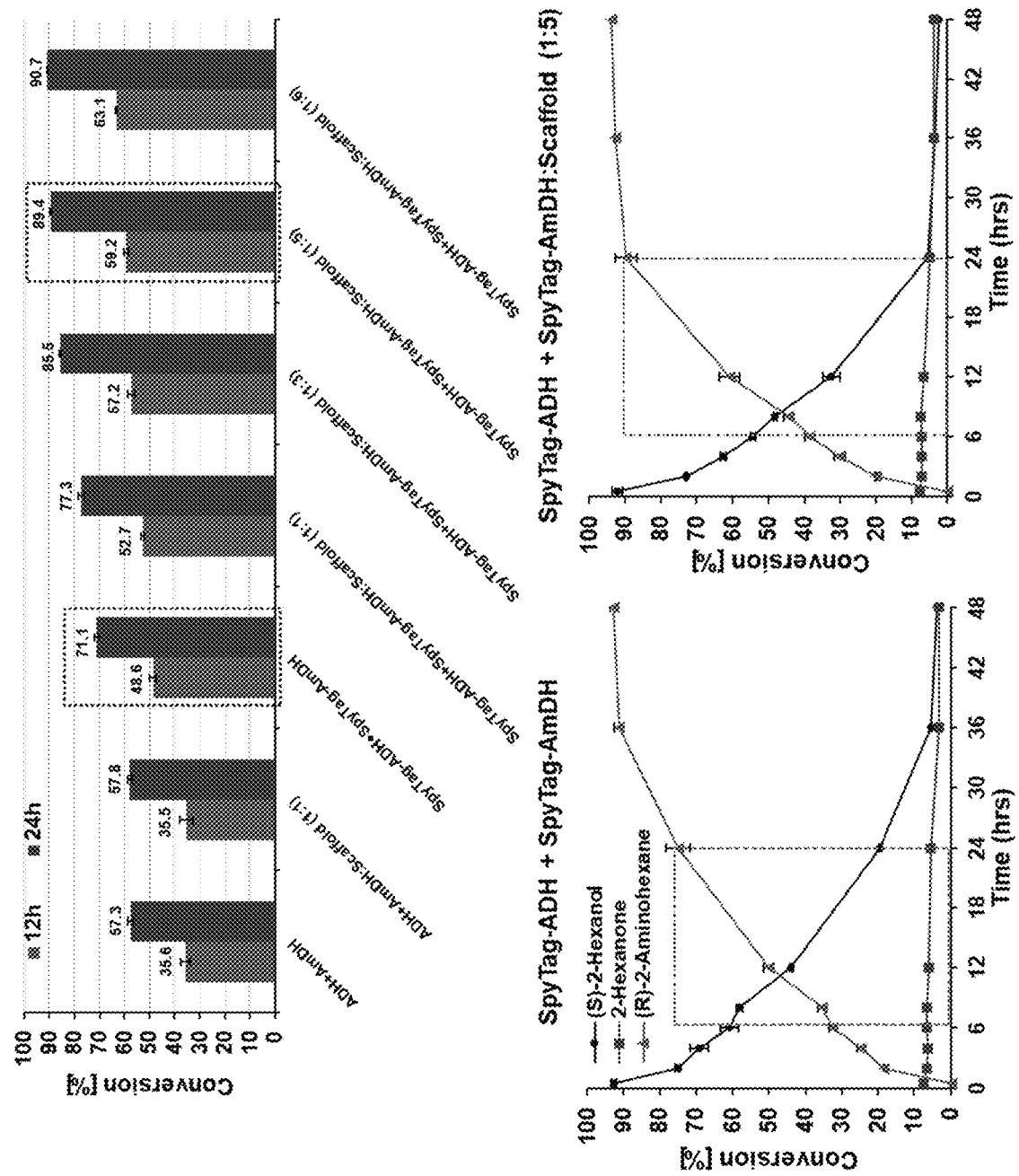
FIG. 18. One-pot amination reaction with free and EutM-SpyCatcher scaffolded dual-enzyme cascade. (A) Characterization of conversion rates of (S)-2-hexanol to (R)-2-aminohexane by free and scaffolded SpyTag-ADH/AmDH dual enzyme cascades (controls contain untagged ADH/AmDH) containing increasing molar ratios of EutM-SpyCatcher. Conversion rates are shown after 12 and 24 hours. (B) Time course of amination reaction by free SpyTag-enzyme cascade. (C) Time course of amination reaction by scaffolded SpyTag-enzyme cascade with 1:5 molar ratio of SpyTag-enzymes and EutM-SpyCatcher. Data are the average of three replicate experiments and error bars are the standard error of the mean. All cascade reactions (A-C) were performed in a 3 mL reaction volume with ammonium chloride buffer (2 M, pH 8.7) at 30° C. and 190 rpm containing 20 mM (S)-2-hexanol, 1 mM NAD$^+$, 6 µM ADH, 150 µM AmDH and EutM-SpyCatcher (scaffold) added to obtain differing molar ratios of enzymes to scaffold. First time point for reaction was analyzed after 0.5 hrs. Conversion rates are shown as percentage (%) of alcohol converted to ketone intermediate and final amine product.

FIG. 18A shows a significant improvement in conversions by the SpyTag-enzyme cascade after 12 hours and after 24 hours. After 12 hours reaction time, conversion by the control reaction cascade ADH+AmDH was 36%, while SpyTag-ADH+SpyTag-AmDH cascade conversion was 49%. This indicates that fusion of SpyTag to the dual enzyme cascade improved activity. When SpyTag-ADH+SpyTag-AmDH on EutM-SpyCatcher scaffolds were co-immobilized at a 1:1, 1:3, 1:5, and 1:6 molar ratio, conversions after 12 hours further increased 4%, 8%, 10% and 16%, respectively. Likewise, conversions after 24 hours were increased further by 6%, 15%, 18% and 20% when SpyTag-ADH+SpyTag-AmDH were co-immobilized on EutM-SpyCatcher scaffolds at a 1:1, 1:3, 1:5 and 1:6 molar ratio. In the case of 1:5 and 1:6 molar ratios, almost complete conversion was reached after 24 hours (89% and 91%, respectively). This indicates that the rate of reaction is significantly improved when the SpyTag-enzyme cascade is immobilized on EutM-SpyCatcher scaffolds at a 1:5 or 1:6 ratio—i.e., reaching almost final conversion in 24 hours as opposed to 36 hours or 48 hours as shown in FIG. 18B and FIG. 18C for the free vs. the scaffolded (at a 1:5 molar ratio) cascades.

Immobilization on EutM-SpyCatcher Scaffolds Stabilizes Enzymes

Figure 19:
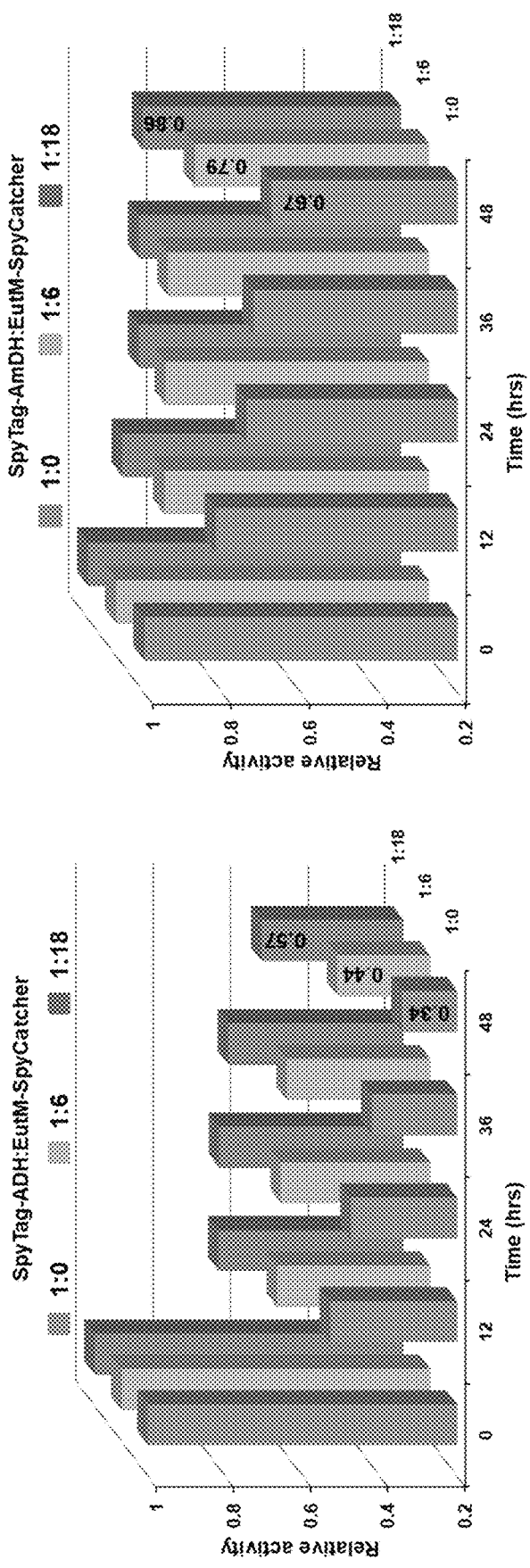
FIG. 19. Effect of EutM-SpyCatcher protein scaffolding on enzyme stabilities. (A) Relative activity of free (1:0) and immobilized on scaffolds (1:6, 1:18) SpyTag-ADH. (B) Relative activity of free (1:0) and immobilized on scaffolds (1:6, 1:18) SpyTag-AmDH. 30 µM purified enzyme was mixed with different molar ratios of EutM-SpyCatcher and incubated under amination reaction conditions at 30° C. and activities were measured every 12 hours for 48 hours. Relative activity assumes 100% activity (set as 1.0) of the enzyme at the beginning of the experiment.

Cascade attachment to the protein scaffolds described herein stabilizes the enzymes, resulting in the shorter reaction times required to reach final conversions of approximately 90%, as shown in FIG. 19. The relative activities of ADH, AmDH, SpyTag-ADH, and SpyTag-AmDH were tested over time in the presence and absence of different molar ratios of EutM-SpyCatcher (FIG. 19). ADH was significantly less stable than AmDH. After 48 hours incubation time, only about 40% relative activity of ADH remained, compared to approximately 65% remaining AmDH relative activity. Adding EutM-SpyCatcher scaffolds (without affording scaffold immobilization) to ADH and AmDH had no significant stabilizing effect. Additionally, control reactions of SpyTag-ADH and SpyTag-AmDH in the absence of EutM-SpyCatcher showed a similar decrease in relative activity over time.

SpyTag-AmDH and SpyTag-ADH stabilities were improved, however, when the enzymes were immobilized on EutM-SpyCatcher scaffolds. In the case of SpyTag-AmDH, stabilization after 48 hours was apparent at all ratios of enzyme:scaffold tested (FIG. 19), with 1:6 SpyTag-AmDH:EutM-SpyCatcher scaffolded enzyme retaining approximately 79% relative activity, compared to about 67% for unscaffolded SpyTag-AmDH. Likewise, at 24 hours, approximately 88% relative activity was retained by 1:6 SpyTag-AmDH:EutM-SpyCatcher scaffolded enzyme, compared to about 74% retained by unscaffolded SpyTag-AmDH. This 14% increase in activity remaining in immobilized SpyTag-AmDH, compared to non-immobilized SpyTag-AmDH, could be partially responsible for the 20% increase in substrate conversion obtained with the immobilized cascade at 24 hours (FIG. 19).

The 1:6 SpyTag-ADH:EutM-SpyCatcher scaffolded enzyme retained approximately 60% relative activity after 24 hours, and approximately 44% relative activity after 48 hours, compared to unscaffolded SpyTag-ADH retaining about 50% relative activity after 24 hours, and about 34% relative activity after 48 hours (FIG. 19). Again, this 10% increase in activity remaining in immobilized SpyTag-ADH, compared to non-immobilized SpyTag-ADH, may play a role in the increase in substrate conversion by the immobilized cascade at 24 hours (FIG. 19). Together, the stabilization of both enzymes in the cascade upon immobilization on EutM-SpyCatcher scaffolds may therefore have increased the rate of reaction compared to the non-immobilized system. The surface of the EutM-SpyCatcher scaffold may provide a favorable microenvironment for enzyme stability.

Additional Features

The EutM protein scaffold platform was expanded by demonstrating and developing additional tools for cargo protein attachment to EutM arrays and creating a toolbox of EutM homologs. For example, cargo proteins may be attached to EutM building blocks using a non-covalent method. Orthogonal coiled-coil interacting peptide pairs were designed based on synthetic peptide sequences shown to interact in vitro. Eight interacting heptade pairs (ABCDEFGH/abcdefgh) were designed and arranged in different combinations of two and four (FIG. 13, showing four interacting heptade blocks) heptade blocks two generate four orthogonal interacting peptide pairs with either two or four heptades. These pairs were fused to the N-terminus of GFP as fluorescent cargo proxy and to the C-terminus of mCherryEutM (mCherry translationally fused to the N-terminus of EutM) using the linker sequences shown in FIG. 14. A complete listing of all peptide pair designs, linkers and color-coded sequences is provided below as Supplemental Information.

Figure 14:
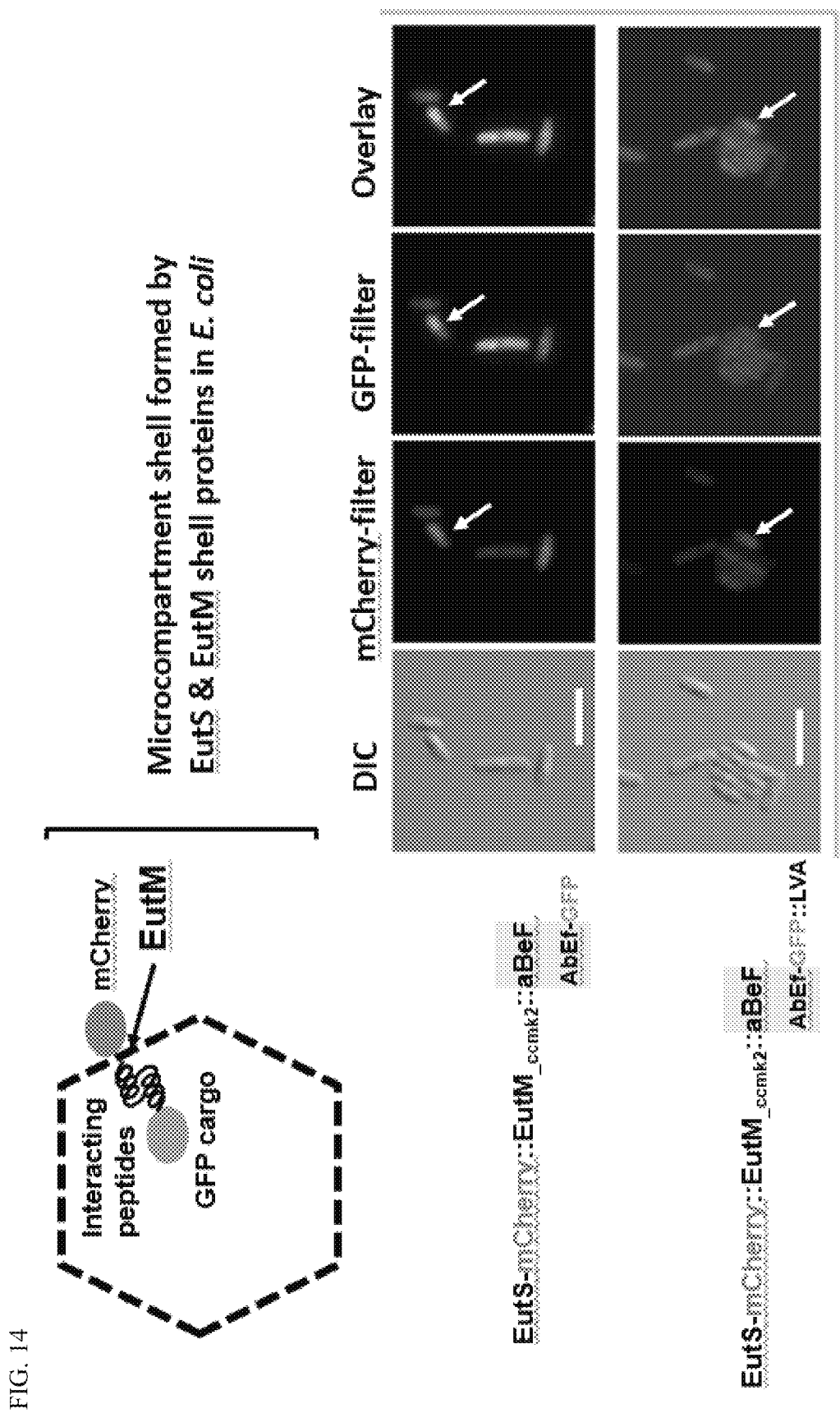
FIG. 14. Non-covalent cargo protein attachment to EutM via orthogonal peptide pairs. Rapid visualization cargo protein interaction with EutM by imaging the formation of recombinant microcompartment shells composed of the shell proteins EutS and mCherryEutM. Co-expression of EutS, mCherryEutM ccmk2 orthogonal peptide aBeF and AbEf-GFP cargo protein results in red and green-donut like protein shells in E. coli that co-localize. Addition of an LVA tag to GFP retains cargo targeting to shells, confirming localization of GFP to the C-terminus and interior of protein shells. Scale bar: 5 µm.

For quick testing of coiled-coil peptide pair interactions between cargo protein and EutM, the system was tested in E. coli by inducing microcompartment formation via the co-expression of the EutS shell protein together with mCherryEutM and GFP cargo fused to cognate peptide pairs. EutS is required to induce microcompartment formation with EutM. Further, mCherryEutM co-expressed with EutS generates red fluorescent donut-like protein shells in E. coli with mCherry, labeling the outside of the shells. The crystal structure of EutM suggests that its C-terminus is located at the opposite site of the EutM hexamer than the N-terminus (see also FIG. 2A) and therefore should be located inside the Eut protein shells. Successful interaction between a EutM C-terminal coiled-coil localization peptide and a cognate N-terminal targeting peptide on GFP cargo should result red fluorescent donut like shells with co-localized green fluorescent, either filling the entire inside of the shells or if tightly bound to the shells, forming a green fluorescent donut-like structure. However, first attempts of direct C-terminal translation fusion of designed orthogonal peptides to mCherryEutM did not target GFP cargo carrying cognate peptide fusions to protein shells in E. coli. Hypothesizing that the orthogonal peptides fused to the C-terminus of EutM may not be assessible for interactions with peptide on the GFP cargo, a chimeric C-terminus was designed by replacing the EutM C-terminus (downstream of the yellow helix in FIG. 3A) with sequences from the carboxysomal shell proteins CcmK2 and Ccmk4. Structural models of CcmK2 and CcmK4 suggest more accessible C-termini. This C-terminal modification of EutM was sufficient to facilitate strong peptide interactions between EutM-containing shells and GFP cargo (FIG. 14). GFP cargo protein remains bound to the EutM-containing protein shells and is not released into the interior, resulting in the visualization of green donut-like shells that co-localize with the red donut-like shells seen for mCherry EutM. Localization to the interior of the shells (i.e., EutM C-terminus facing into the lumen) was validated by adding a commonly used protein degradation tag to GFP.

Whereas GFP carrying this tag is rapidly degraded when expressed in *E. coli*, encapsulation of GFP cargo into the interior or shells prevents degradation and thus, green donut-like shells form as shown in FIG. 14.

The successful design of a strong non-covalent attachment method for cargo proteins (e.g., enzymes) to EutM demonstrates that alternative methods in addition to covalent linkage can be designed to direct protein cargo to EutM arrays. Many natural occurring peptide-peptide/protein-protein interactions as well as designed interactions are known and could be modified for use with EutM. The specificity of peptide-peptide pair interactions provides tools with which to control the co-localization of cargo protein on scaffolds Further, non-covalent interactions for example make it possible to exchange/recycle enzyme cargo on EutM protein scaffolds in situ.

EutM Toolbox

A BLAST search with the *Salmonella enterica* EutM (EutM_SE) in the NCBI sequence database for homologs returned hundreds of sequences from prokaryotes. These identified sequences were screened and reduced to 294 protein sequences with complete sequence information and from identified organisms. Sequences from 51 bacteria isolated from extreme environments suggesting adaptation of their proteins to conditions relevant for conditions under which biocatalytic reactions are performed (e.g., species known to be able to survive at extreme temperature, pH, salinity, or pressure) were phylogenetically analyzed. 13 additional homologs in addition to *S. enterica* EutM_SE were selected to build a EutM toolbox (see Table 3 for sequences and source organisms). Together these 14 EutM's cover the phylogenetic sequence diversity of EuM homologs identified by the BLAST search and group into three clades (FIG. 1C).

Additional design and characterization considerations can further improve a well characterized platform for rapid prototyping and optimization of multi-enzyme cascades of choice. For example, electrostatic properties of the surface on which enzymes are immobilized can influence microenvironments for enzyme function. Therefore, having a diverse range of EutM building blocks for the assembly of protein scaffolds, each with different electrostatic surface properties, could allow one to create tailored scaffolds for different cascades requiring different conditions. Furthermore, spacing between immobilized enzymes can influence the efficiency of cascade catalysis. As such, it would be desirable to have a system for the straightforward assembly of various scaffolding architectures with different building blocks as spacers.

Structural modeling of EutM hexamers shows that the different hexamer models have different surface charge patterns and hexamer interfaces (FIG. 1C), suggesting that they have different self-assembly characteristics and that their surfaces provide various microenvironments for biocatalysis.

Bioinformatic Identification of a Diversity of EutM Homologs

To build a toolbox of scaffold building blocks with diverse properties, a sequence-based approach was used to identify EutM homologs. Initial BLASTp searches using the protein sequence EutM from *S. enterica* (WP 024798609.1) as search template resulted in hits only from the family Enterobacteriaceae (phylum Proteobacteria), indicating a high degree of EutM sequence conservation in this family. To improve the likelihood of identifying diverse homologs, the search parameters were changed by increasing the number of expected hits, by reducing the stringency of the Evalue search parameter, and by excluding taxonomic ID:90370 (*Salmonella enterica* subsp. *enterica* serovar *Typhi*). This resulted in the identification of 483 protein sequences related to EutM from *S. enterica*, from a wide range of prokaryotes.

Proteins from microorganisms living in extreme environments have evolved to be more robust under these conditions, a characteristic that can be useful for biotechnological processes that often require harsh reaction conditions. Therefore, the list of 483 sequences was manually curated to select protein sequences from microorganisms that have been isolated from varied environments, including previously characterized BMC shell proteins PduA from *S. enterica* (WP_098065011.1), PduJ from *S. enterica* (WP_023213491.1), EutM from *C. difficile* (WP_021364550.1), and EutM from *E. coli* (WP_097763906.1) as anchor sequences for initial comparative analyses. Following curation, the list contained 48 homologs of EutM encoded by bacteria belonging to phyla Firmicutes (Clostridia, Bacilli), Proteobacteria (γ-Proteobacteria, δ-Proteobacteria), Spirochaetae (Spirochaeta) and Chloroflexi (Anaerolineae). Some of the bacteria were isolated from environments with extreme conditions, including high temperatures (e.g., 60° C.), low temperatures (e.g., −1.5° C.), acidic conditions (e.g., pH 3.5), alkaline conditions (e.g., pH 10.5), or high salt (e.g., 12% NaCl) conditions.

Figure 21:
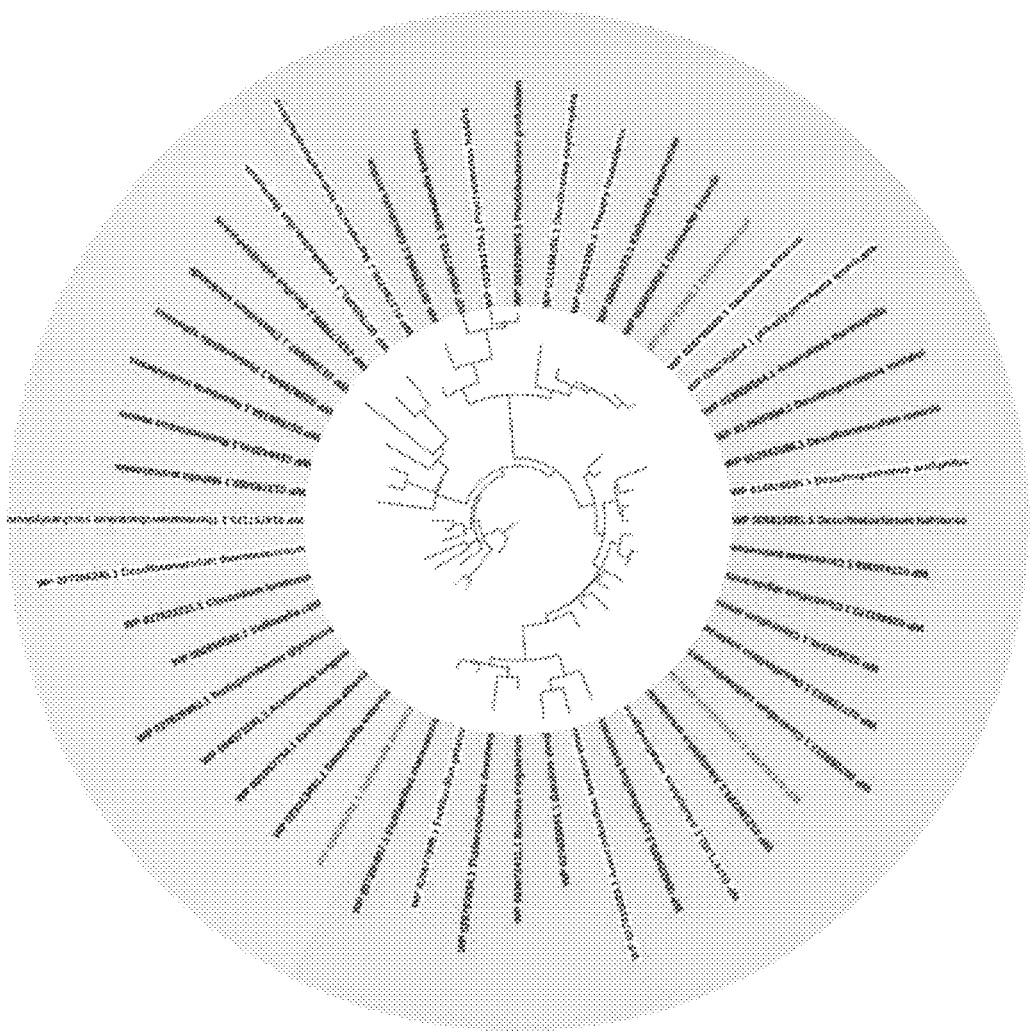
FIG. 21. Phylogenetic analyses of a curated list EutM homologs identified by BLAST search. The curated list of 48 EutM homologs identified includes previously characterized PduA from *S. enterica* (WP 098065011.1), EutM from *E. coli* (WP 097763906.1), and EutM from *C. difficile* (WP 021364550.1) (names highlighted in italics) for comparative analyses. EutM homologs cluster into three distinct clades around each of these characterized proteins. Top: those most closely related to PduA from *S. enterica*; right: those most closely related to EutM from *E. coli*; left and bottom: those most closely related to EutM from *C. difficile*. Names highlighted in white are those homologs that were selected for cloning and characterization in this study, representing members from each clade.

Phylogenetic analyses of the 48 protein sequences indicated that the homologs fell into three broad clades (FIG. 1C, FIG. 21) that formed around the previously characterized BMC shell proteins (PduA from *S. enterica*, EutM from *E. coli*, and EutM from *C. difficile*). EutM from *S. enterica* clustered most closely with EutM from *E. coli*, with which it shares 96% sequence identity. Within each clade, sequences branched into sub-clades, suggesting that members from different clades, and from different sub-clades, could represent proteins with distinct properties. To explore this idea, 13 candidate sequences were selected, including EutM from *S. enterica* as a control, as representatives from each clade for further characterization. Proteins were named according to the bacteria from which they were identified—e.g., EutM from *S. enterica* became "EutM SE", EutM from *Thauera linaloolentis* became "EutM TL" (for the full list of sequences and names, see Table 4).

Sequence-Structure Guided Predictions of EutM Homolog Characteristics

Figure 20:
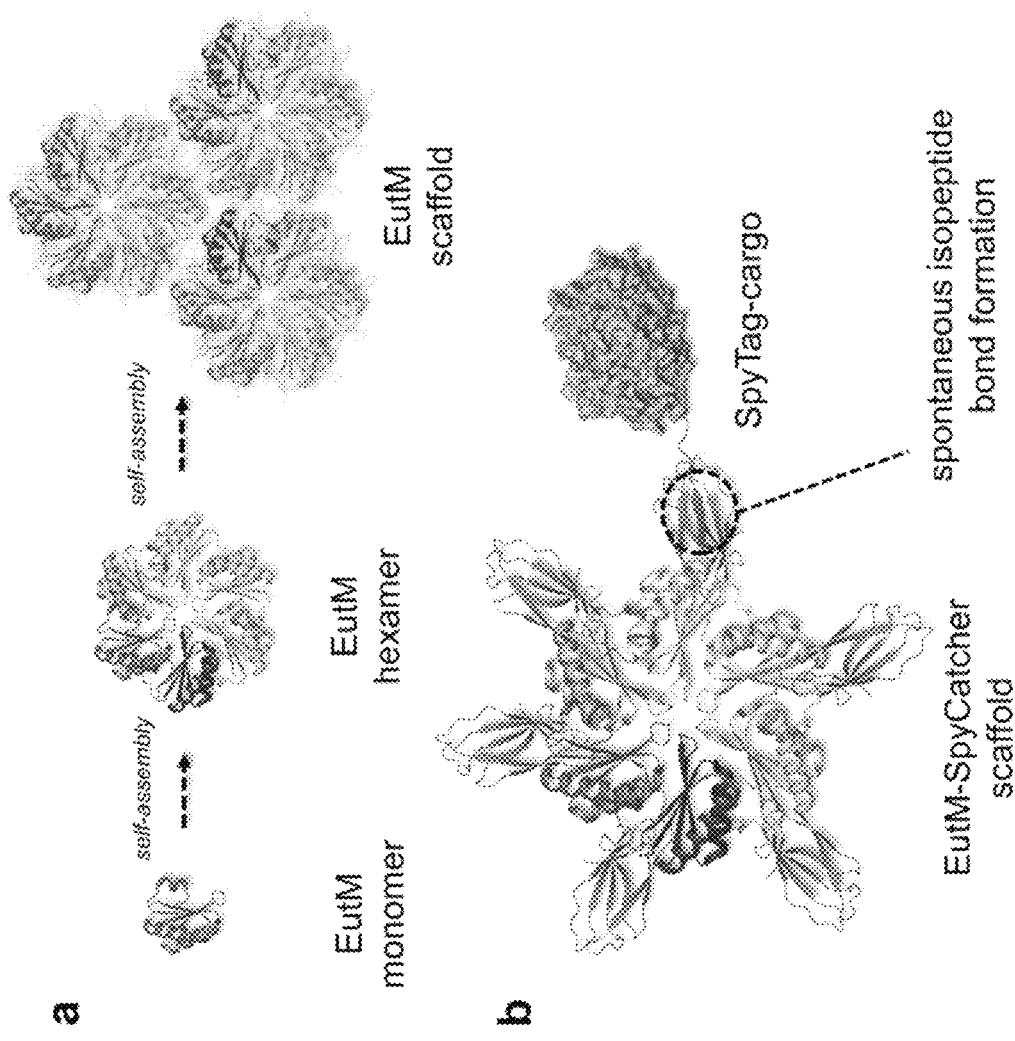
FIG. 20. Illustration of self-assembly of protein scaffolds for enzyme immobilization. (A) EutM monomers (left) can self-assemble into hexamers (middle). The EutM hexamers self-assemble into scaffolds (right) that form the outer shell of bacterial microcompartments (BMCs). (B) A SpyCatcher domain can be fused to the C-terminus of EutM to create EutM-SpyCatcher scaffolds. A SpyTag domain can be fused to the N-terminus (or C-terminus) of cargo proteins of choice. SpyCatcher-SpyTag mediated isopeptide bond formation occurs spontaneously, covalently attaching cargo proteins to EutM-SpyCatcher scaffolds.
Figure 22:
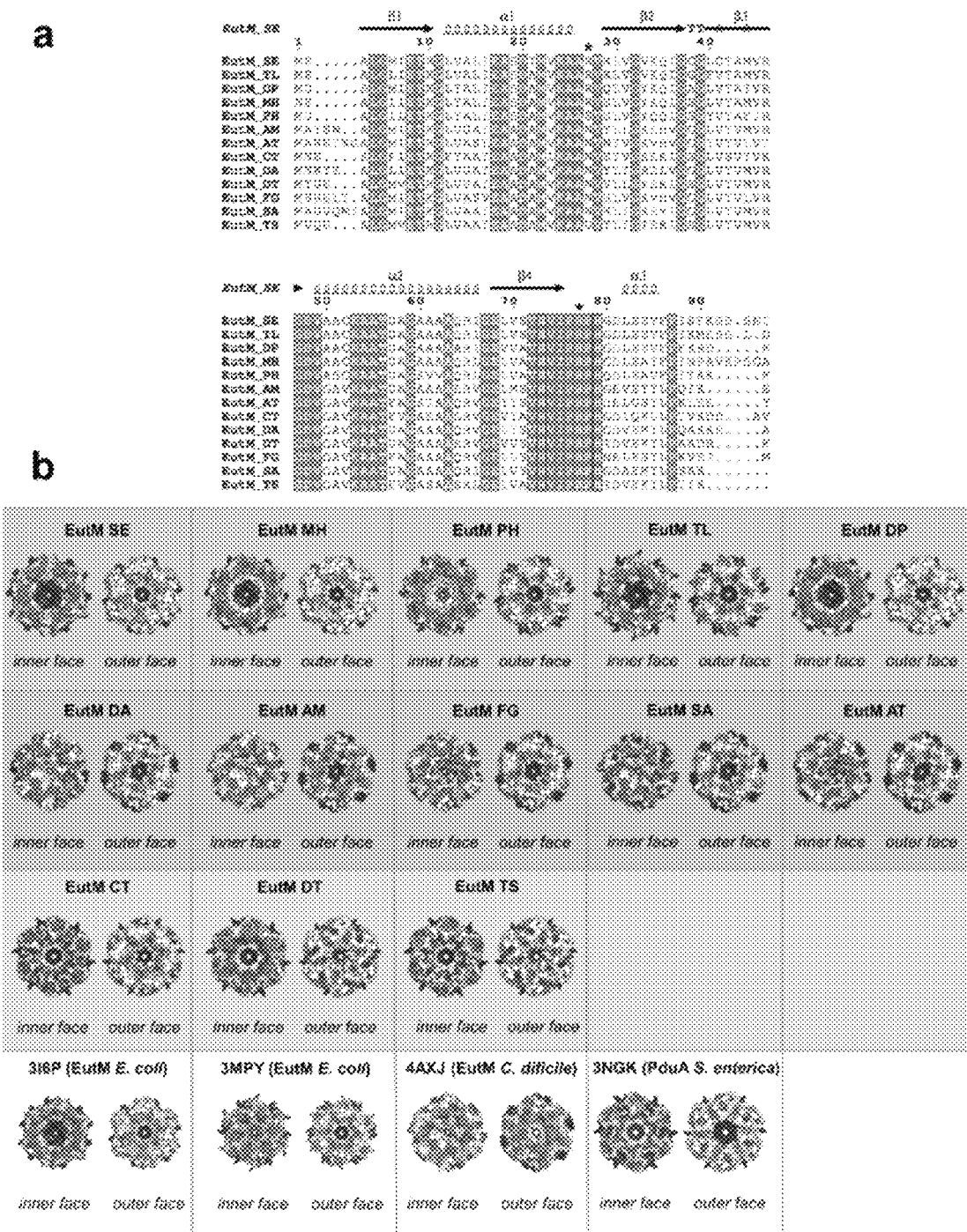
FIG. 22. Protein homology models of 13 EutM homolog candidates. (A) Sequence alignment of the selected EutM homologs (EutM SE, SEQ ID NO:33; EutM TL, SEQ ID NO:55; EutM DP, SEQ ID NO:43; EutM MH, SEQ ID NO:49; EutM PH, SEQ ID NO:51; EutM AM, SEQ ID NO:35; EutM AT, SEQ ID NO:37; EutM CT, SEQ ID NO:39; EutM DA, SEQ ID NO:41; EutM DT, SEQ ID NO:45; EutM FG, SEQ ID NO:47; EutM SA, SEQ ID NO:53; EutM TS, SEQ ID NO:57) indicates that the most variable region of the protein sequences is at the N-terminus and C-terminus. Amino acids that are typically involved in interactions between hexamer interfaces are indicated with an asterisk (*). (B) Protein models were generated using the most closely related structurally characterized homolog. First row: those that were modeled using the crystal structure of EutM from *E. coli* as a template (PDB ID: 3I6P or PDB ID: 3MPY; Second row: those that were modeled using the crystal structure of EutM from *C. difficile* as a template (PDB ID: 4AXJ; Third row: those that were modeled using the crystal structure of PduA from *S. enterica* as a template (PDB ID: 3NGK. Protein models are displayed as hexamers and as electrostatic potential renderings of the surface of the structure, generated using PyMOL. Red represents negative charge and blue represents positive charge. Both faces of the hexamer are shown, with inner face indicating the side that is predicted to point to the interior lumen of bacterial microcompartment shells, and outer face indicating the side that is predicted to point to the cytosol of bacteria. A homology model of EutM SE is also included for comparison, as well as surface representations of crystal structures that were used for modeling.

To gain insight into properties of the 13 selected EutM homologs, the amino acid sequence of each protein was analyzed (FIG. 22A). Calculated molecular weights of the proteins showed that they were all predicted to be in the size range 9.4 kDa to 9.9 kDa, and calculated isoelectric points of the proteins were between 5.0 and 6.7 (Table 4). This did not give any information whether the proteins would likely assemble into hexamers or larger structural arrays similar to other characterized BMC shell proteins, including EutM SE (FIG. 20A). Nor did it provide any information whether any of the potential hexamers had different surface properties, which could provide unique microenvironments for enzymes.

Structural models of the proteins were therefore generated by homology modeling against known crystal structures of BMC shell proteins. All homologs closely related to PduA from *S. enterica* were modeled using PDB ID: 3NGK as a template, while those related to EutM from *C. difficile* were modeled using PDB ID: 4AXJ as a template. Two different crystal structures are available for EutM from *E. coli*, PDB ID: 3MPY (Takenoya et al., 2010. *J Bacteriol* 192:6056-6063) and PDB ID: 3I6P (Tanaka, 2010. *Science* 327:

81-84), providing different models when used as templates. This may be due, at least in part, to 3MPY having a structure that is more complete at the C-terminus than 3I6P. According to sequence identity, EutM SE, EutM DP, and EutM MH were all modeled using 3I6P, and EutM TL and EutM PH were modeled using 3MPY.

Electrostatic potential surface renderings of the structural models indicated that the overall surface charge of these hexameric assemblies appears to vary between homologs (FIG. 22B). Those with the most negatively charged surface are closest to EutM from E. coli. In all homologs, however, the distinctive pattern of charge distribution varies. Additionally, the conformation of arginine side chains that are typically involved in interactions between hexameric interfaces, varies between homologs (FIG. 22A, FIG. 22B). These differences in modeled charge distributions and side-chain conformations at hexameric interfaces could translate into different assembly properties of the homologs.

Purification and In Vitro Characterization of the EutM Homologs

Figure 23:
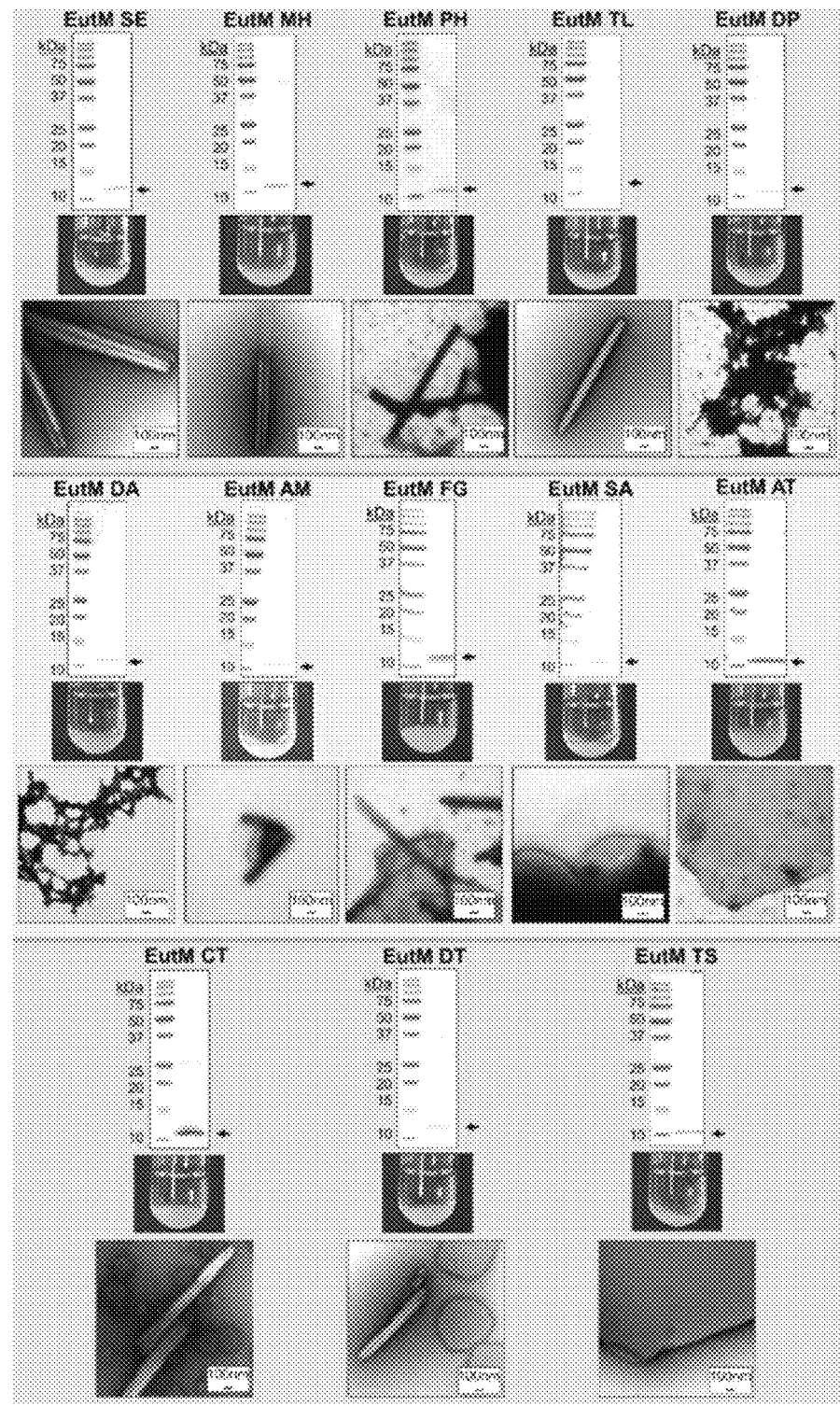
FIG. 23. In vitro characterization of recombinantly expressed and purified EutM homologs. Synthetic genes encoding the EutM homologs were synthesized with codon optimization for expression in *E. coli*. Expressed proteins were purified by $Ni^{2+}$ affinity chromatography. The His-tagged, purified proteins appear as an approximately 12 kDa band on a SDS-PAGE gel (top row, band highlighted with an arrow). Upon purification, the proteins rapidly precipitated out of solution as a whitish precipitate that sank to the bottom of the tube (middle row, photographs). Negative stain TEM analyses (bottom row, grey scale images) of the proteins at ~1.0 mg $mL^{-1}$ showed that the proteins had self-assembled as µm or nm scale structures (e.g. needles, rolled up sheets, flat sheets, gel-like materials). TEM images were taken at a magnification of 53,000× and the scale bar represents 100 nm. Top: those most closely related to EutM from *E. coli*; Middle: are those most closely related to EutM from *C. difficile*; Bottom: those most closely related to PduA from *S. enterica*.

Genes encoding 13 new, uncharacterized EutM homologs were synthesized and expressed in E. coli to determine whether they would also self-assemble into protein arrays as was seen with EutM. All 13 proteins were purified to homogeneity in one step by $Ni^{2+}$ affinity chromatography, with protein concentrations ranging from 0.2 mg $mL^{-1}$ to 2.0 mg $mL^{-1}$. The purified proteins formed a white precipitate in the tube within minutes of separation from the column (FIG. 23). Also, while the His-tagged purified proteins could be detected as bands of approximately 12 kDa (including the 6×His tag) on SDS-PAGE denaturing gels (FIG. 23), at times the proteins behaved aberrantly, running as double bands or as higher molecular weight species, despite boiling (100° C.) in denaturing buffer for 10 minutes. Together, these observations suggested that the proteins rapidly self-assembled into higher order structures in vitro.

The purified proteins were dialyzed to remove salts and the protein concentrations were normalized before visualization by negative stain transmission electron microscopy. In all cases, the EutM homologs formed nanometer or micrometer scale structures (FIG. 23). These appeared as different types of architectures, which fell into categories according to phylogeny of homologs. Some of the EutM from E. coli-like homologs formed well-ordered nanotubes with rigid edges that were approximately 100 nm wide and up to about 1 µm in length, and seemed to be rolled-up but not completely closed (EutM SE, EutM MH, EutM TL). In the case of EutM MH, an apparently "broken" nanotube was observed, which at higher magnifications appeared to be composed of tightly aligned long, thin fibers (<10 nm in diameter). EutM PH also formed tube-like structures but these tended to form larger assemblies of tubes, creating indistinct masses that were micrometers in size. EutM DP behaved very differently to its closest homologs, instead forming a disordered aggregate or gel-like material.

The structures formed by the EutM from C. difficile-like homologs were more varied, both fibril-like structures and flat sheet-like scaffolds were observed. EutM AM and EutM FG assembled as flat sheets that appeared as plate-like structures with rounded edges, as well as fibrils that were reminiscent of the rolled-up tubes seen with the EutM from E. coli-like homologs, but were less wide (20-50 nm in diameter), sometimes longer (>5 µm in length in the case of EutM FG), and not as rigid. The fibril-like structures were not observed in EutM SA and EutM AT, which instead formed only the plate-like flat sheets. In EutM SA these sheets were layered on top of each other to give heavily-stained tiles that seemed multi-dimensional (micrometers in size), while the sheets in EutM AT appeared thinner, not as obviously layered, and were smaller (1-2 µm across). EutM DA formed disordered aggregates.

Finally, the PduA from S. enterica-like homologs also formed both tube-like structures and flat scaffolds. EutM CT and EutM DT formed tubes that were approximately 100 nm in diameter and about 1 µm in length, as well as flat scaffolds that appeared as mottled structures with rounded edges that are approximately 100 nm to 500 nm in diameter. EutM_TS did not form tubes, instead forming plate-like flat sheets (micrometers in size) that were layered to give multidimensional structures.

Temperature Robustness of EutM Scaffolds

Figure 24:
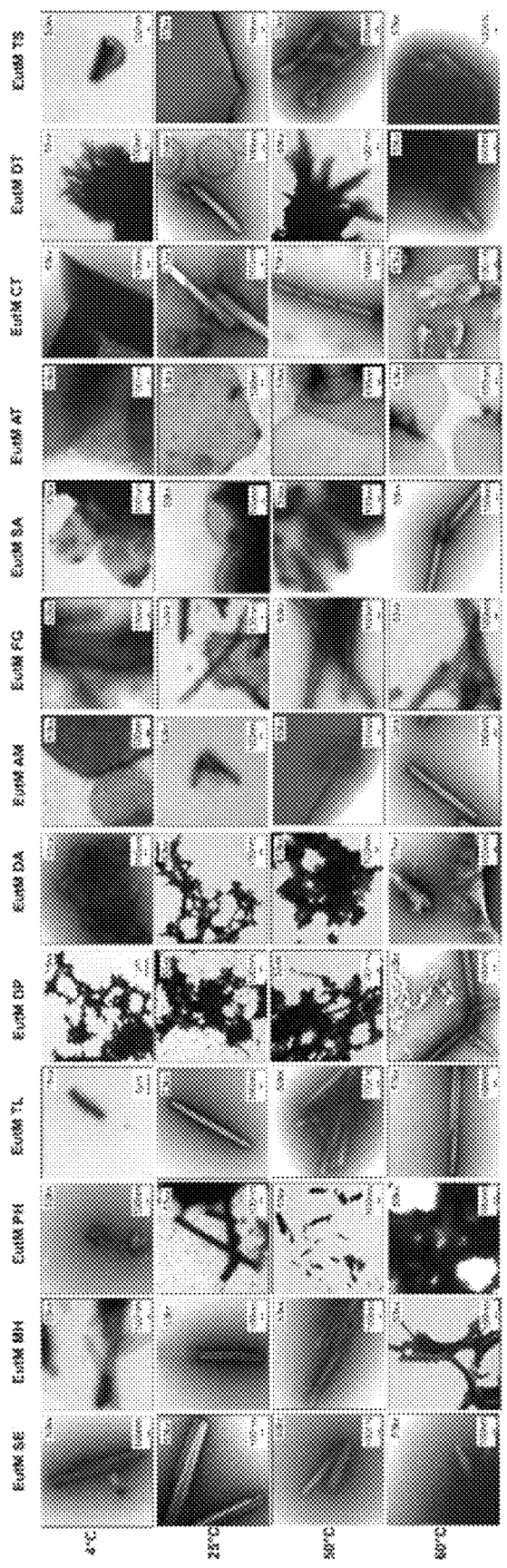
FIG. 24. Shelf-life and temperature robustness of EutM protein scaffolds. Purified proteins (~1.0 mg $mL^{-1}$) were stored at 4° C. for six weeks in Buffer C. Additionally, the proteins were incubated at 50° C., and at 60° C. for 12 hours in Buffer C, and their ability to retain their self-assembly properties into nm or µm scale structures (e.g. needles, rolled up sheets, flat sheets, gel-like materials) was measured by negative stain TEM analyses. Images were taken at a magnification of 53,000× (unless otherwise noted) and the scale bar represents 100 nm. Images at 25° C. are those reported in FIG. 22, included here for comparison.

The EutM homologs were selected, in part, based on the fact that they were identified in bacteria isolated from extreme environments and, therefore, may offer temperature robustness necessary to perform a wide range of biocatalytic reactions. EutM(SE)-SpyCatcher scaffolds remain stable for 12 hours at 50° C. Thus, the temperature robustness of the novel EutM scaffolds was tested upon incubation at 50° C. and 60° C. for 12 hours (FIG. 24). All of the EutM homologs still formed scaffold-like structures after incubation at 50° C. In some cases, however, the morphology of the structures was different than those previously observed after incubation of the protein at room temperature (25° C.) (FIG. 23, FIG. 24). For example, EutM PH formed shorter and thinner (~200 nm×10 nm) needles as opposed to the large masses of tubes that form at after incubation at room temperature. Also, EutM DP began to form needle-like structures within the previously observed disordered gel-like material. Notably, EutM FG no longer assembled as flat sheets, but only as the fibrils that had been previously observed, and EutM SA morphology had completely changed from plate-like sheets to fibril-like structures of approximately 500 nm in length× 100 nm in diameter. This temperature dependent change in morphology became more noticeable after incubation at 60° C. (FIG. 24), particularly in case of EutM DP and EutM SA, both of which now assembled as well-ordered needles that were hundreds of nanometers in length. Some of the homologs began to lose their ability to self-assemble as ordered structures after incubation at 60° C. (e.g., EutM SE, MH, PH, DA, CT, TS), while others remained robust and well-ordered as needles, fibrils, or flat sheets (e.g., EutM TL, DP, AM, FG, SA, AT, DT).

In addition, the long-term stability (i.e., "shelf-life") of the EutM homologs was investigated by confirming that scaffold structures remained after six weeks storage at 4° C. (FIG. 24). EutM SE, MH, TL, AM, FG, SA, CT, DT, and TS retained a well-ordered scaffold structure (e.g., needles, fibrils, flat sheets). On the other hand, EutM PH and AT lost the ability to form large structures. EutM DP and DA remained as disordered aggregates/gel-like materials.

Figure 26:
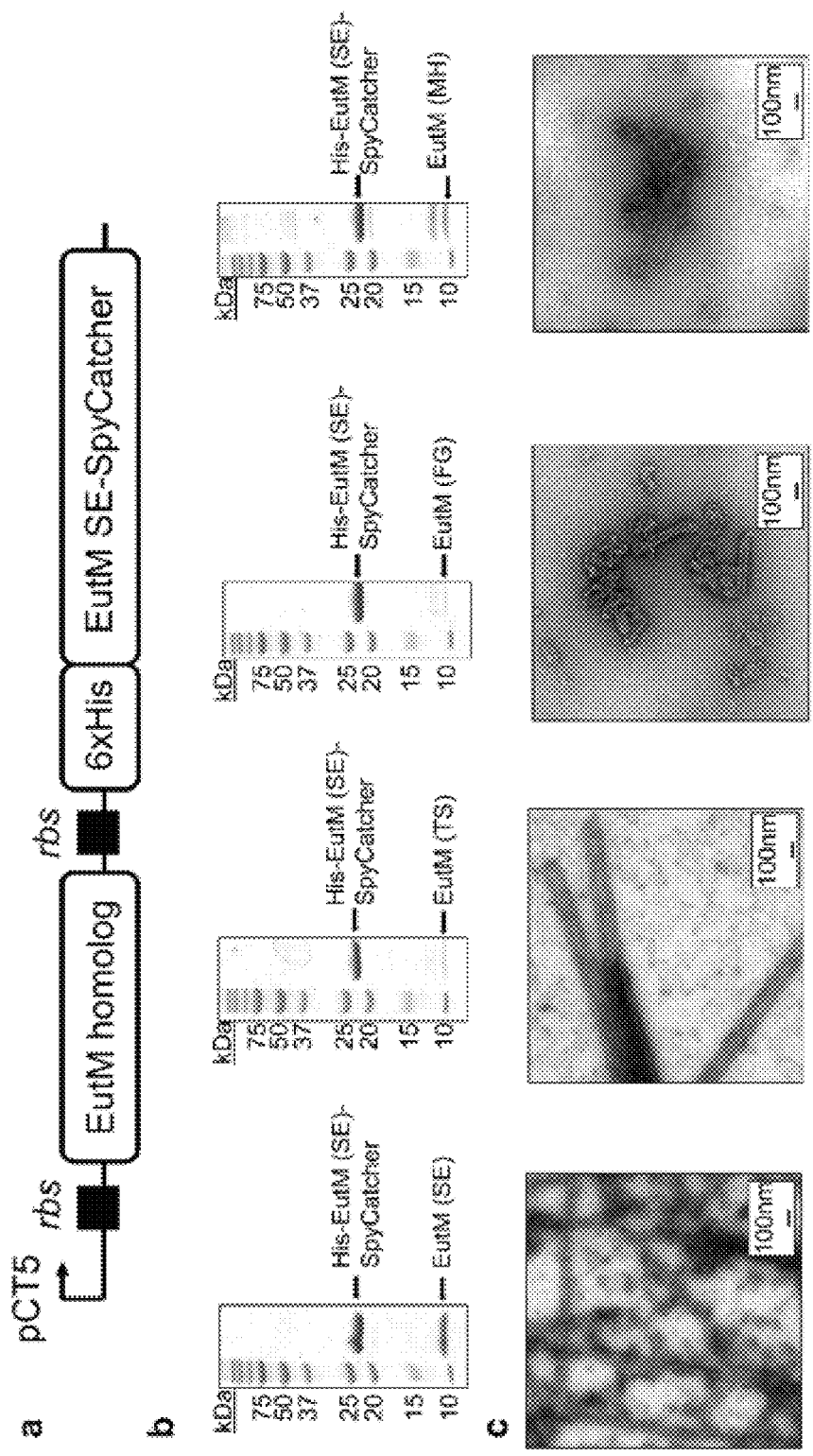
FIG. 26. Design and characterization of hybrid EutM His-EutM-SpyCatcher scaffolds. (A) Schematic design of synthetic operons for the co-production of hybrid scaffolds with spacer building blocks and integrated enzyme attachment points. Both genes eutM(homolog) and His-eutM(SE)-SpyCatcher are under the control of the same cumate inducible promoter pCT5, but have their own synthetic ribosome binding site (rbs) for transcription initiation. (B) Synthetic operons were expressed recombinantly in *E. coli* and the formation of hybrid protein scaffolds consisting of EutM(homolog) and His-EutM(SE)-SpyCatcher was confirmed by $Ni^{2+}$ affinity pulldowns. SDS-PAGE analysis shows that non-His tagged EutMs (10 kDa) co-elute from a Ni²⁺ affinity column with His-EutM(SE)-SpyCatcher (21 kDa). (C) Negative stain TEM analyses of purified hybrid scaffolds from the Ni²⁺ affinity pulldowns confirm self-assembly into nm scale structures. Images were taken at 53,000× and the scale bar represents 100 nm.

Developing Hybrid and Chimeric EutM Scaffolds with Integrated Enzyme Attachment Points The EutM homologs were next used to develop a synthetic biology platform to mix-and-match EutM building blocks of different properties as self-assembled scaffolds with different surface microenvironments, with integrated enzyme attachment points. The S. enterica EutM-Spy-Catcher scaffolds were used as a starting point since they rapidly and spontaneously immobilize and stabilized Spy-Tagged-enzymes. Artificial operons were designed for the co-expression of different EutM homologs with His-tagged EutM(SE)-SpyCatcher under the control of a cumate inducible promoter (FIG. 26A). To test whether hybrid scaffolds would self-assemble, representative EutM homologs from each of the different clades of our phylogenetic tree, with different assembly architectures, were integrated into the artificial operons (FIG. 26A).

Proteins were co-expressed from artificial operons in *E. coli* and were tested for their ability to interact as a hybrid scaffold by $Ni^{2+}$ affinity pulldowns (FIG. 26B). In this experiment, His-tagged EutM(SE)-SpyCatcher would bind to the $Ni^{2+}$ affinity column and would elute in high imidazole buffer, and any non-His-tagged EutM homologs that could interact with His-EutM(SE)-SpyCatcher would coelute from the column. In all four cases, non-His-tagged EutM coeluted with His-EutM(SE)-SpyCatcher, detected as two bands on SDS-PAGE gels (EutM(homolog) is ~10 kDa and His-EutM(SE)-SpyCatcher is ~21 kDa). The relative amount of non-His-tagged EutM that coeluted from the column varied, with EutM_SE and MH appearing the most abundant. These results suggested that hybrid scaffolds may form when different EutM homologs are co-expressed with His-EutM(SE)-SpyCatcher.

To further explore the possibility that hybrid scaffolds could form, the proteins obtained from $Ni^{2+}$ affinity pulldown experiments (FIG. 26B) were analyzed by negative stain TEM (FIG. 26C). The control protein EutM(SE) His-EutM(SE)-SpyCatcher appeared as long flexible fibrils (hundreds of nanometers in length and ~40 nm in diameter). Protein EutM(TS) His-EutM(SE)-SpyCatcher had a similar long flexible fibril morphology, however, the fibrils were thicker than EutM(SE) His-EutM(SE)-SpyCatcher (i.e., 100 nm in diameter as opposed to 40 nm in diameter). In contrast, proteins EutM(FG) His-EutM(SE)-SpyCatcher and EutM(MH) His-EutM(SE)-SpyCatcher had significantly different structures compared to the control protein. Instead of long flexible fibrils, these appeared as short tubes (~200 nm in length×~20 nm in diameter) or small plate-like structures (~100 nm in length×~100 nm in diameter). These structures were also very different from those formed by the individual EutM homologs. These data suggest that the different EutM homologs were capable of interacting with His-EutM(SE)-SpyCatcher, and the interacting proteins were assembling as hybrid scaffolds.

Figure 25:
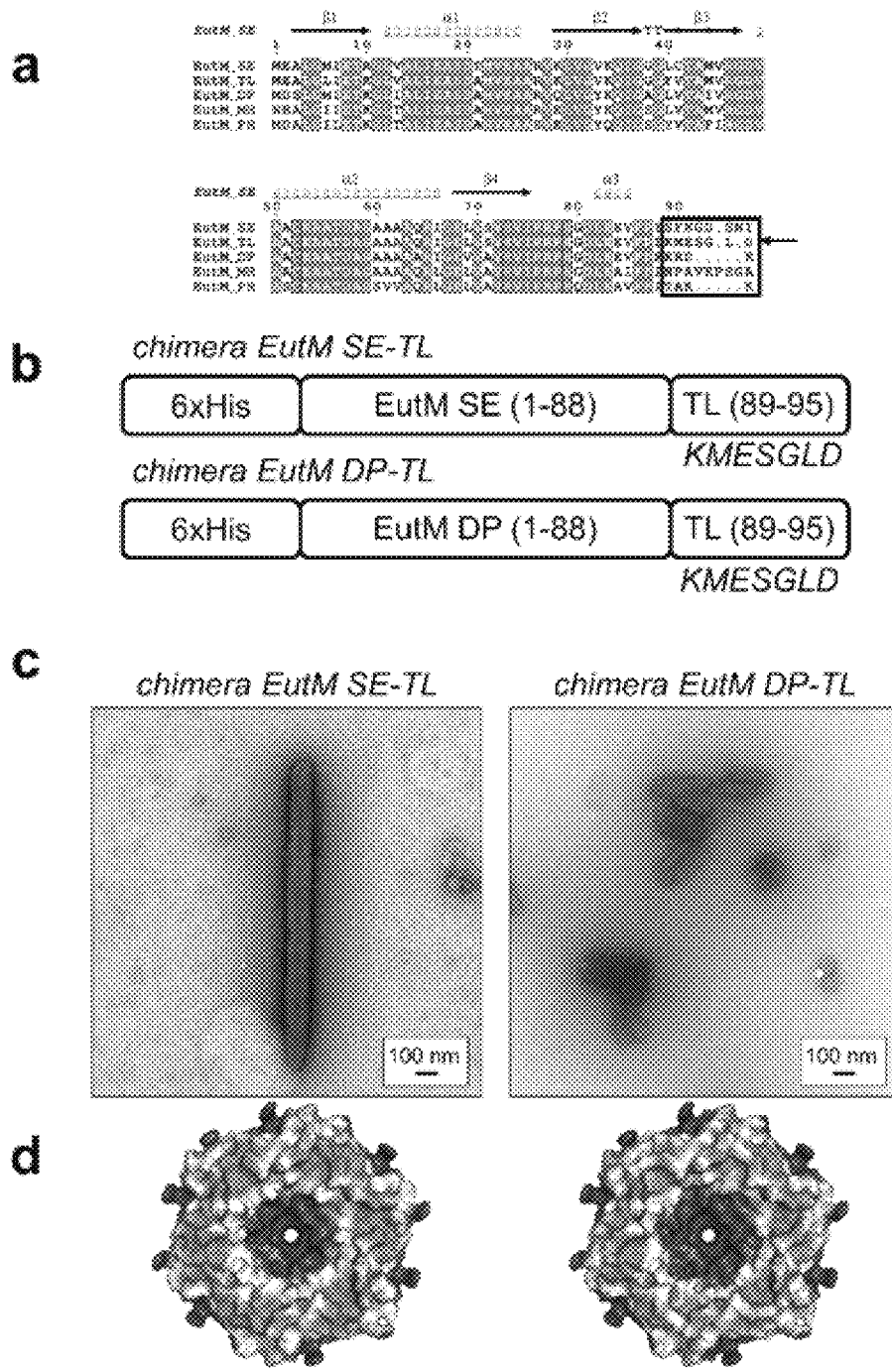
FIG. 25. Design and characterization of chimeric EutM proteins. (A) Protein sequence alignments of EutM homologs (EutM SE, SEQ ID NO:33; EutM TL, SEQ ID NO:55; EutM DP, SEQ ID NO:43; EutM MH, SEQ ID NO:49; EutM PH, SEQ ID NO:51) most closely related to EutM SE show that the C-terminus of the proteins is the most variable region (box). The final seven amino acids of EutM TL (arrow) was used to replace the C-terminus of EutM SE or EutM DP to create chimeras EutM SE-TL and EutM DP-TL. (B) Schematic design of chimeras EutM SE-TL and EutM DP-TL. The amino acid sequence that was used to replace the C-terminus of proteins is provided in italics. (C) Chimeric proteins were purified by Ni' affinity and their self-assembly characteristics were analyzed by negative stain TEM. Images were taken at a magnification of 53,000X and the scale bars represent 100 nm. (D) Protein homology models (generated using PDB ID: 3I6P as a template) of the chimeric proteins are displayed as electrostatic potential surface renderings, with red representing negative charge and blue representing positive charge.

Finally, chimeric EutM homologs with non-native sequences were engineered so that they still self-assemble and potentially form new scaffolds with different electrostatic surface properties (FIG. 25C). Based on sequence alignments EutM homologs (FIG. 25A), the C-terminal region was identified as highly variable between homologs (FIG. 25B). Two chimeric EutM homologs (HisEutM(SE-TL) and EutM(DP-TL) with a C-terminal sequence from EutM(TL) were designed, purified and characterized for scaffold formation by negative stain TEM (FIG. 25C). Both chimeric EutM still formed different scaffolds from their parental sequences; EutM(SE-TL) forming tightly rolled up tubes and EutM(DP-TL) short, tube-like structures (FIG. 25B).

Cargo Loading on Hybrid EutM Scaffolds

As initial proof of concept that the scaffolds could serve as immobilization platforms, the model cargo protein GFP was loaded onto the hybrid EutM(homolog) His-EutM(SE)-SpyCatcher scaffolds. By taking advantage of the well-characterized SpyCatcher-SpyTag technology, which enables the covalent linkage of proteins via an isopeptide bond, cargo loading on scaffolds should happen spontaneously (FIG. 20B). SpyTag-GFP, or GFP as a control, was mixed with the EutM(homolog) His-EutM(SE)-SpyCatcher proteins at a 1:1 molar ratio and incubated at room temperature for one hour. SpyTag-GFP formed a covalent bond with His-EutM(SE)-SpyCatcher, which could be detected as a higher molecular weight 53 kDa band on a denaturing SDS-PAGE gel. In contrast, no 53 kDa band could be seen on a denaturing SDS-PAGE gel when GFP lacking SpyTag was mixed with the scaffolds. The isopeptide bond formation between SpyTag-SpyCatcher occurred with all four hybrid proteins EutM(SE) His-EutM(SE)-SpyCatcher, EutM(MH) His-EutM(SE)-SpyCatcher, EutM(TS) His-EutM(SE)-SpyCatcher, and EutM(FG) His-EutM(SE)-SpyCatcher, indicating that the presence of different EutM homologs in the scaffold does not hinder cargo loading. In all cases, a small amount of SpyTag-GFP remained unattached to the scaffolds despite the one-hour incubation.

Figure 27:
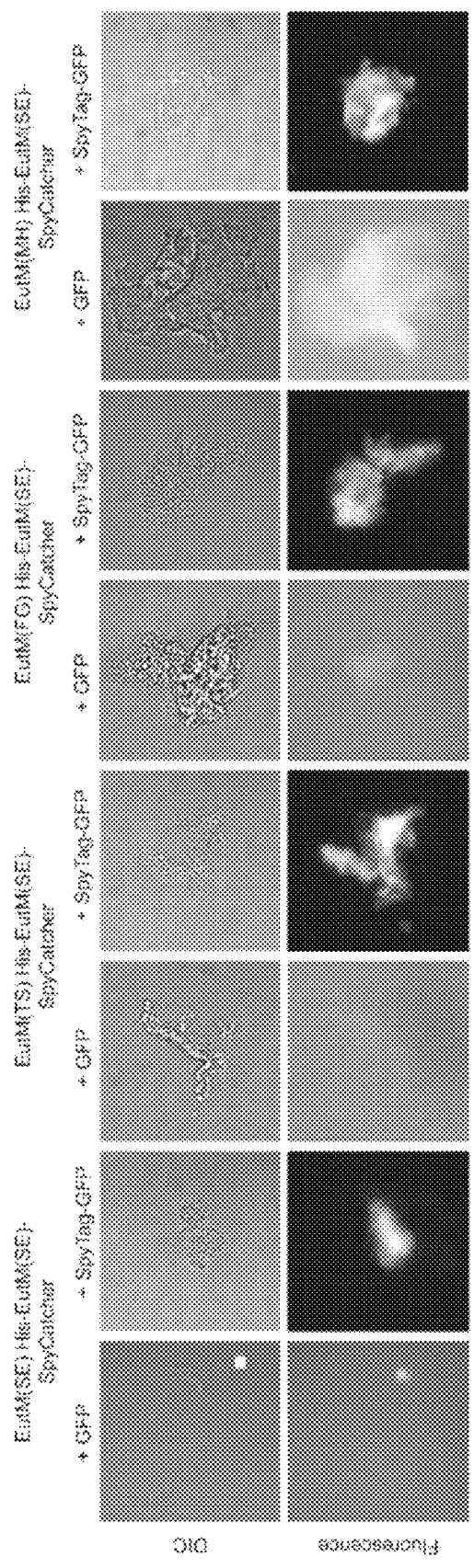
FIG. 27. Cargo loading on hybrid EutM His-EutM-Spy-Catcher scaffolds. Fluorescence microscopy imaging of EutM His-EutM-SpyCatcher hybrid protein scaffolds mixed with SpyTag-GFP, or GFP as a control, shows that SpyTag-GFP localizes to scaffolds in vitro, while GFP remains diffuse. DIC images were taken to highlight protein scaffold boundaries. Images were taken at 100× and the scale bar represents 5 μm.

Finally, cargo loading onto pre-assembled scaffolds was confirmed by light microscopy. As previously described, the scaffolds appear as flexible film-like materials (~100 μm in size) when viewed at lower magnifications. Similar films were observed when EutM(homolog) His-EutM(SE)-SpyCatcher scaffolds were viewed using the light microscope (FIG. 27), with sizes of the films ranging from approximately 10 μm in diameter to approximately 100 μm in diameter. When SpyTag-GFP was mixed with the scaffolds, the films became fluorescent, indicating that SpyTag-GFP can be immobilized on pre-assembled scaffolds. On the other hand, GFP lacking SpyTag did not bind to the films and remained diffuse. These data confirm that the self-assembling hybrid scaffolds can be used to immobilize cargo proteins.

Thus, differences in surface charges, interfaces, and/or self-assembly into different types of protein arrays provides a valuable toolbox with which to tune and optimize protein scaffolds towards the specific requirements of multi-enzyme cascade reactions. The ability to mix different ratios of EutM building block homologs and to control ratios and attachment of cargo enzyme creates a powerful platform for the design of efficient multi-enzyme biocatalytic pathways.

This disclosure therefore describes a protein scaffold that generally includes a plurality of EutM subunits that form a scaffold structure. The scaffold generally includes enzymes of an enzyme cascade attached to the scaffold, as described in more detail, below.

As used herein, the term "EutM subunits" refers to a EutM polypeptide, such as, for example, any of the EutM polypeptides set forth in Table 3 or any other native EutM (i.e., published wild-type) amino acid sequence of a EutM polypeptide. Alternatively, a "EutM subunit" may be a homolog of a native EutM polypeptide. As used herein, a polypeptide is a homolog of a native EutM polypeptide if the amino acid sequence of the polypeptide possesses a specified amount of similarity or identity compared to a native EutM polypeptide and self-assembles into a protein scaffold as described herein. The sequence identity of two polypeptides can be determined by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the native EutM polypeptide. A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In comparing two amino acid sequences, "sequence identity" refers to the presence of identical amino acids. "Sequence similarity" refers to the presence of not only identical amino acids but also the presence of conservative substitutions. A conservative substitution for an amino acid in a EutM polypeptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$. Likewise, biologically active analogs of a polypeptide containing deletions or additions of one or more contiguous or noncontiguous amino acids that do not eliminate a functional activity of the polypeptide are also contemplated.

A EutM subunit can therefore include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to a native EutM amino acid sequence, so long as the polypeptide self-assembles into a scaffold structure as described herein.

In some embodiments, a EutM subunit can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a native EutM amino acid sequence, so long as the polypeptide self-assembles into a scaffold structure as described herein.

A EutM subunit also can be designed to provide additional sequences, such as, for example, the addition of added C-terminal or N-terminal amino acids that can, for example, facilitate purification by trapping on columns or use of antibodies. Such tags include, for example, histidine-rich tags that allow purification of polypeptides on nickel columns. Such gene modification techniques and suitable additional sequences are well known in the molecular biology arts. In some embodiments, a EutM subunit may be engineered to possess at least one chemically modified amino acid to facilitate attaching an enzyme to the EutM subunit.

A scaffold may include a homogeneous population of EutM subunit polypeptides or, alternatively, may include a heterogenous mixture of EutM subunit polypeptides, thereby forming a hybrid protein scaffold. When heterogeneous, the various species of EutM subunit polypeptides can include native EutM polypeptides, homologs of native EutM polypeptides, and/or modified EutM polypeptides.

An enzyme may be attached to its respective EutM subunit by any suitable attachment chemistry including, but not limited to, a covalent attachment, and affinity attachment, or an ionic attachment. Exemplary covalent attachment strategies include, for example, covalent crosslinking that may or may not involve chemically-modified amino acid subunits that facilitate the crosslinking or translationally fusing the EutM subunit and enzyme. Exemplary affinity attachment strategies include ligand-receptor affinity, peptide-peptide affinity, avidin-biotin affinity, etc.

Figure 15:
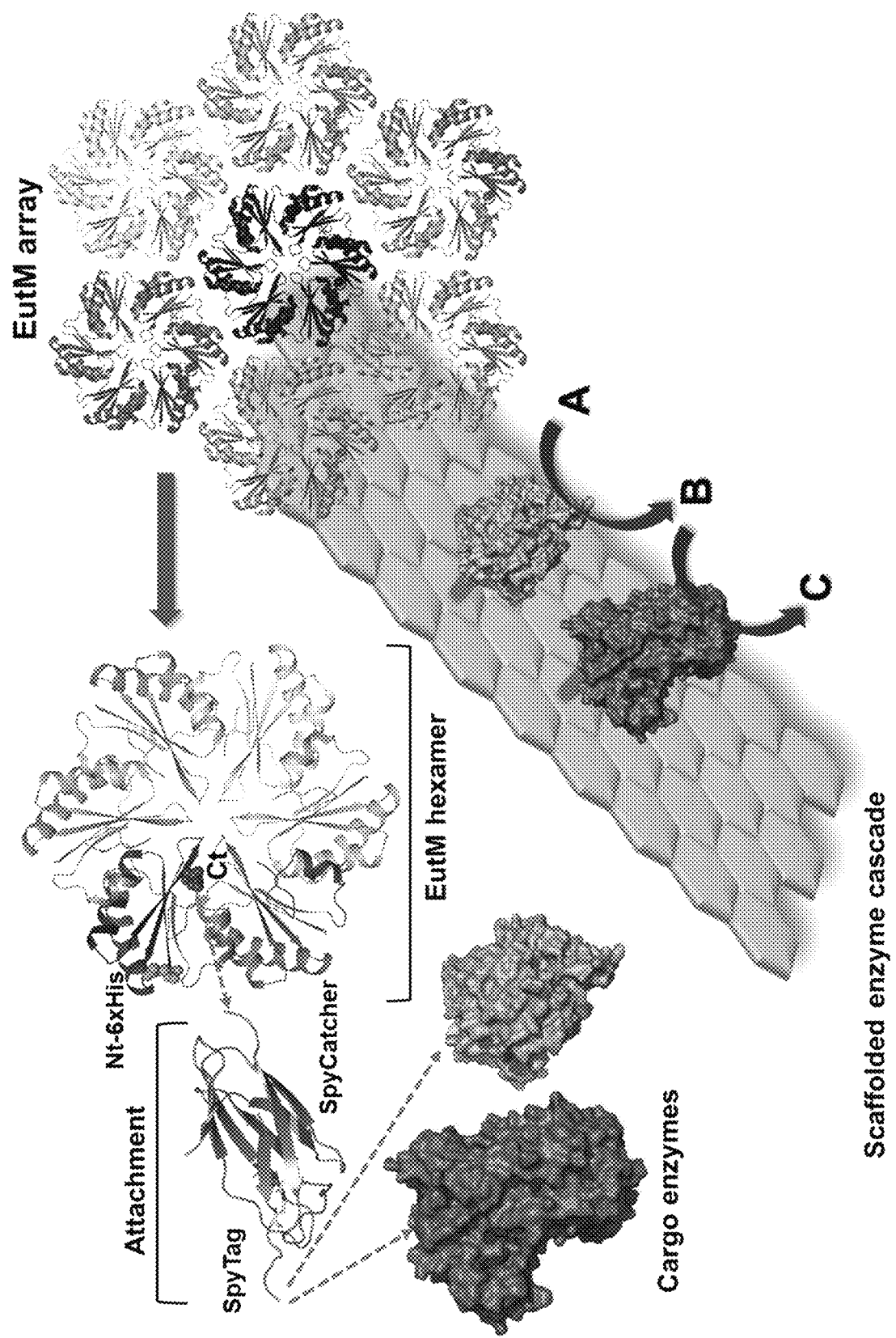
FIG. 15. Enzymes are covalently attached to scaffolds by fusing a SpyCatcher domain (green) to the C-terminus of EutM monomers and a SpyTag peptide sequence (blue) to the N-terminus or C-terminus of cargo-enzymes. SpyCatcher and SpyTag form a covalent isopeptide bond (yellow), attaching enzymes to scaffolds.

The scaffold provides a framework for a multi-enzyme cascade that includes two or more enzymes, such as, for example, as illustrated in FIG. 9 and FIG. 15. FIG. 9 shows an illustrative two-enzyme cascade that includes a first enzyme (ADH) attached to a first EutM subunit and a second enzyme (AmDH) attached to a second EutM subunit. The EutM protein scaffold platform described herein can be designed to include any number of enzymes required for a desired enzymatic cascade.

FIG. 9 and FIG. 15 also show the EutM subunits to which the enzymes are attached can be modified to include a reactive group (SpyCatcher) that facilitates attaching the enzyme through a complementary reactive group (SpyTag) that is attached to each enzyme. While illustrated showing both enzymes being attached to the EutM scaffold using the same attachment technology, a scaffold may be designed so that different enzymes are attached to their respective EutM subunits using different attachment chemistries. In this way, one can design a scaffold that includes different enzymes selectively attached to the scaffold through individualized attachment chemistries in a pre-designed array to control the spatial proximity of enzymes in a sequential enzyme cascade.

Also, while FIG. 9 illustrates a single enzyme being attached to a EutM subunit, it may be possible to design a scaffold that includes multiple enzymes attached to a single EutM subunit.

In another aspect, this disclosure describes a method of making a protein scaffold. Generally, the method includes simply incubating a plurality of EutM subunits under conditions allowing the EutM subunits to self-assemble into a protein scaffold. The completed scaffold will include, as described, immediately above, a first enzyme of a multi-enzyme cascade attached to a first EutM subunit and a second enzyme of the multi-enzyme cascade attached to a second EutM subunit.

Each enzyme may be attached to its respective EutM subunit independently of any other enzyme that is attached to the protein scaffold. Moreover, each enzyme may be, independently of any other enzyme, attached before the scaffold is assembled or after the scaffold is assembled. For example, one can first attach a cargo enzyme to its EutM subunit and then allow the EutM subunits to self-assemble to form the protein scaffold. Alternatively, one can preform scaffolds and then load one or more cargo enzymes onto the preformed scaffold.

Scaffold self-assembly can occur either in vitro or in vivo. In vivo self-assembly can occur by simply co-expressing EutM subunits and allowing the EutM subunits to self-assemble. A single cell may be engineered to express a single EutM subunit, which can self-assemble into a homogeneous scaffold. Alternatively, a single cell may be engineered to express multiple EutM subunits (e.g., multiple native EutM polypeptides and/or homologs), which can self-assemble to form a heterogeneous (or hybrid) scaffold. In some embodiments, a cell may be engineered to express a EutM subunit translationally fused to a cargo enzyme and the EutM-enzyme fusions may be allowed to self-assemble. In vitro self-assembly can involve isolating EutM subunits—again, either a homogeneous population of EutM polypeptides or a heterogeneous mixture of EutM polypeptides—and incubating the EutM polypeptides under conditions that allow the EutM subunits to self-assemble into a scaffold.

Likewise, each enzyme may be, independently of any other enzyme, attached to the scaffold in vivo or in vitro. In vivo attachment can involve, for example, co-expressing the EutM subunit and the cargo enzyme in a single cell and allowing the EutM and enzyme to attach (e.g., by peptide-peptide affinity) in vitro. Attachment of the enzyme to its EutM subunit also can be considered in vivo when the enzyme and the EutM subunit are translationally fused. In vitro attachment can involve, for example, mixing EutM subunits with cargo enzymes. In some of these embodiments, a scaffold can include a subpopulation of EutM subunits possessing one attachment chemistry that is complementary to the attachment chemistry of a one enzyme, and a second population of EutM subunits that possess a second attachment chemistry that is complementary to a second enzyme. In this way, a plurality of different enzymes may be attached to specific addressable locations on the scaffold in a single attachment reaction.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials

All chemical reagents were purchased from Sigma-Aldrich, unless otherwise indicated. PHUSION DNA polymerase for PCR amplifications, Q5 Site-Directed Mutagenesis kit for Q5-site directed mutagenesis, HIFI DNA assembly master mix for HiFi-assembly of DNA fragments, T4 DNA ligase, and all restriction endonucleases were purchased from New England BioLabs, Inc. (Ipswich, Mass.).

Molecular Biology

All plasmids generated in this work are listed and described in Table 1. Sequences for EutM_SE scaffold building blocks, reporter and enzyme cargo are provided in Table 2. Table 3 lists sequences for EutM homologs. Cloning and routine molecular biology methods follow standard methods. Q5-mutagenesis and HiFi-assembly reactions were carried out according to NEB's instructions and using NEB's online tools for optimal primer and DNA fragment design and for optimal annealing temperatures. All sequences were verified by Sanger sequencing. Synthetic DNA fragments and genes were either synthesized as GBLOCKS from Integrated DNA Technologies, Inc. (Coralville, Iowa) or as synthetic DNA fragments from GenScript (Piscataway, N.J.).

Three plasmid backbones were used to construct the expression vectors: the in-house BIOBRICK (iGEM, Cambridge, Mass.) compatible pBRBB for protein expression from a constitutive lac promoter, a commercial pET28a expression vector for IPTG inducible protein expression from a T7 promoter (Invitrogen Corp., Carlsbad, Calif.) and pCT5BB which was derived from pUCBB-pCT5-ntH6-eGFP (a pUCBB vector with cumate-inducible $P_Q5$ promoter; Vick et al., 2015. *Appl Environ Microbiol* 81(4): 1406-1416) by removing a BamHI site and making the multiple cloning site fully compatible with pBRBB and other in-house BioBrick expression plasmids.

Cloning of SpyTagged eGFP/mCherry and EutM-Spycatcher

A SpyTag with GS linker was translationally fused to the N-terminus or C-terminus of eGFP and mCherry in pBBRBB-eGFP and pBBRBB-mCherry, respectively, by Q5-mutagenesis to generate pBBRBB-SpyTag-eGFP/mCherry and pBBRBB-eGFP/mCherry-SpyTag for in vivo co-location experiments. The SpyTag fused reporter genes were amplified for cloning into the NdeI and NotI sites of pET28a and a N-terminal 6×His-tag followed by a thrombin cleavage site and GS-linker was added by Q5 mutagenesis. The resulting plasmids were name pET28a-SpyTag-eGFP and pET28a-eGFP-SpyTag. The pCT5BB-EutM-Spycatcher (EMSC) plasmid was generated by HiFi-assembly of pCT5BB vector backbone and *S. enterica* EutM_SE (Choudhary, et al., 2012. *PLoS One* 7(3):e33342) PCR products and SpyCatcher fragment amplified from GBLOCKS (Integrated DNA Technologies, Inc., Coralville, Iowa). The pCT5BB-SpyCatcher control plasmid was generated from pCT5BB-EMSC by in frame deletion of EutM using Q5-mutagenesis.

Cloning of SpyTag ADH and AmDH

Sequences encoding the alcohol dehydrogenase from *Aromatoleum aromaticum* (AA-ADH) and chimeric amine dehydrogenase chimera (AmDH:Ch1-AmDH a chimera of the N-terminal domain (1-149) of PheDH from *Bacillus badius* and C-terminal domain (140-366) of Leu-DH from *Bacillus stearothermophilus*; Bommarius et al., 2014. *Chemical Communications*, 50(95): 14953-14955) reported by Mutti et al. (*Science* 349(6255): 1525-1529. 2015) were synthesized as GBLOCKS (Integrated DNA Technologies, Inc., Coralville, Iowa). For the N-terminal SpyTag plasmids, AA-ADH and Ch1-AmDH genes were cloned into pET28a-SpyTag-eGFP using SalI and NotI to replace eGFP. For C-terminal SpyTag plasmids, the two genes were cloned into pET28a-eGFP-SpyTag using NdeI and SalI to replace eGFP. To construct control plasmids without SpyTag, the SpyTag was cleaved from the pET28a-AA-ADH/Chl-AmDH-SpyTag plasmids.

Cloning of EutM Homologs

EutM-SE was subcloned from a pUCBB plasmid (Choudhary et al., 2012. *PLoS One* 7(3): e33342) into the BamHI and NotI sites of pCT5BB to generate pCT5BB EutM_SE. Sequences encoding EutM homologs EutM-DP, EutM-PH, and EutM-TL were synthesized by GenScript and subcloned from its source plasmid pUC57-Kan into pCT5BB using BamHI and NotI (see Table 3 for sequences and bacterial sources of EutM homologs). Histidine immobilized metal affinity chromatography (IMAC) tags (hexahistidine followed by six Gly-Ser repeats) were added to the 5' end of genes encoding EutM-SE, EutM-DP, EutM-PH, and EutM-TL by Q5-mutagenesis. Sequences encoding EutM-AM, EutM-AT, EutM-CT, EutM-DA, EutM-DT EutM-FG, EutM-MH, EutM-SA, and EutM-TS were directly synthesized with the 5' histidine tags by GenScript and also subcloned into pCT5BB. EutM_BM was amplified from *B. megaterium* genomic DNA for cloning into pCT5BB.

Cloning of Fluorescent Cargo and EutS mCherryEutM Constructs for Orthogonal Peptide Targeting Plasmid pCT5BB-EutS-mCherryEutM was created first as template for all subsequent C-terminal modifications of mCherryEutM for orthogonal peptide targeting. This plasmid was created by first individually cloning EutS and mCherryEutM (Quin et al., 2016. *Appl Microbiol Biotechnol* 100(21): 9187-9200) each into the BamHI and XhoI sites of pCT5BB to create pCT5BB-EutS and pCT5-mCherryEutM followed by BioBrick stacking of the mCherryEutM expression cassette (including promoter and terminator) into pCT5BB-EutS. All modifications at the C-terminus of mCherryEutM, including replacement of EutM's C-terminal region with those of the carboxysomal shell proteins CcmK2 and CcmK4 (Samborska, B. and M. S. Kimber, 2012. *Structure* 20(8): 1353-1362) and fusion sequences encoding orthogonal peptide tags were achieved by one or several rounds of Q5-mutagenes with appropriate primers. The pBRBB-eGFP constructs with N-terminal orthogonal peptide tags to GFP were likewise constructed by Q-5 mutagenesis. A C-terminal LVA degradation tag (Andersen et al., 1998. *Appl Environ Microbiol* 64(6): 2240-2246) was also fused to GFP by Q-5 mutagenesis.

In Vivo Co-Localization Studies

In Vivo Co-Localization of Fluorescent Cargo Proteins and EutM Scaffolds pBRBB-SpyTag-eGFP/mCherry and pCT5-EMSC and other control combinations of pBRBB cargo and pCT5 scaffold plasmids (Table 1) were co-transformed into *E. coli* C2566. Cells containing both plasmids were cultivated at 30° C. overnight in LB supplemented with ampicillin (100 μg mL$^{-1}$) and kanamycin (30 μg mL$^{-1}$). For EutM scaffold formation alone, only the pCT5-EutM plasmids were transformed into *E. coli* C2566 cells that were grown with ampicillin only. Overnight cultures were transferred into fresh LB (1:100 dilution) and grown at 30° C. for 2-3 hours to an OD of $A_{600}$=0.4-0.6. Expression of EMSC was then induced with 50 cumate after which cultures were grown at 37° C. for five hours. SpyTag-eGFP is expressed from a constitutive lac promoter on the low-copy number plasmid pBBRBB (Vick et al. 2011. *Appl Microbiol Biotechnol* 92(6): 1275-1286). Cells were pelleted and washed in PBS (pH 7.4) for light microscopy and TEM imaging.

In Vivo Co-Localization of mCherry-Labeled Protein Shells and Fluorescent Cargo for Orthogonal Peptide Studies pBRBB fluorescent cargo plasmids and pCT5-EutS-mCherryEutM orthogonal peptide plasmids (and control combinations) (Table 1) were co-transformed into *E. coli* C2566. Proteins were expressed and cells collected for microscopy as described above for in vivo co-localization of fluorescent cargo proteins and EutM scaffolds.

Imaging of Cells and Purified Scaffolds

Fluorescence Emission Spectroscopy

Static images of *E. coli* C2566 cells and scaffolds were acquired using a Nikon Eclipse 90i microscope equipped with bright field, DIC, phase, and fluorescence optics including a 120 W X-Cite epi-fluorescence illuminator with blue (excitation filter 470-490 nm, barrier 520-580 nm) and green (excitation filter 510-560 nm, barrier 570-620 nm) filter sets. The samples were viewed using a 100×, 1.4 n.a. plan apo objective. Post-capture image analyses and cropping was conducted in Nikon NIS Elements Viewer 4.6 and GIMP 2. For fluorescence microscopy, 16-bit digital images were collected using a Roper Cool Snap HQ monochrome camera and captured using Image Pro Plus software. DIC microscopy was performed using a 1.4 n.a. oil condenser.

Transmission Electron Microscopy (TEM) of Bacterial Cells

Bacterial cells were fixed in 2.5% glutaraldehyde in 0.1 M phosphate buffer, followed by three washes with 0.1 M phosphate buffer. Triton X-100 was added to the glutaraldehyde solution and rinse buffer to a final concentration of 0.1%. Subsequently, the pellets were post-fixed with 1% osmium tetroxide in 0.1 M phosphate buffer, washed with nanopure water, and embedded in 2% low melting agarose. The cell-agarose pellet was cut into 1 mm$^3$ cubes, and dehydrated using an ethanol gradient. The cell agarose cubes were then incubated in 1:1 mixture of Embed 812 resin and 100% ethanol for four hours, followed by an 18-hour incubation in 100% Embed 812 resin. Next, they were suspended in a fresh Embed 812 resin-N, N-dimethylbenzylamine (BDMA) solution and polymerized at 60° C. for 48 hours. 90 nm sections were sliced, placed on 200 mesh formvar-coated copper grids, and post-stained with 3% uranyl acetate and Triple lead stain. Specimens were observed and photographed with a Philips CM12 transmission electron microscope. Post-capture alignment and cropping was conducted in GIMP 2.

Negative Stain TEM of EutM Scaffolds In Vitro

10 μL protein scaffold sample was pipetted onto a 200 μm mesh copper coated grid and left for a few minutes. 10 μL Trumps fixative reagent was pipetted on top of the protein drop and again left for a few minutes before excess fluid was wicked off using filter paper. 10 μL dH$_2$O was pipetted onto the grid and excess fluid immediately wicked off. Next, 10 μL 2% uranyl acetate was pipetted onto the grid, left for 15-30 secs and excess fluid wicked off. Grids were allowed to air dry before storage or imaging. Scaffolds were imaged on a Phillips CM12 TEM with magnifications of 15,000×, 53,000×, and 175,000×.

Protein Expression and Purification

Expression of His-Tagged Proteins from pCT5BB

Cells transformed with pCT5BB plasmids for expression of His-tagged EutM_SE, EutM-SpyCatcher, EutM-SpyCatcher::SpyTag-eGFP and EutM homologs were grown overnight at 30° C. in LB supplemented with 50 μg/ml ampicillin. Overnight cultures were diluted 100-fold and grown at 30° C. to and OD of $A_{600}$=0.4-0.6. Protein expression was then induced with 50 μm cumate and the cultures were grown at 37° C. for six hours.

For protein purification, cells were resuspended in lysis buffer (20 mM imidazole, 50 mM Tris, 250 mM NaCl, pH8) and disrupted by sonication (30 min, power 50%, pulse on 20 s, and pulse off 40 s). The lysed cells were centrifuged (12,000 rpm, 40 min, 4° C.) and the supernatant passed through am 0.22 µm ultra-filter. Nickel affinity chromatography following standard HisTrap HP and AKTAFPLC techniques (GE Healthcare Life Sciences, Pittsburgh, Pa.) were used to purify all proteins. After elution from the columns, proteins were subjected to centrifugal filters (Amicon/Millipore-Sigma) (3 kDa for EutM and 10 kDa for other proteins) to remove salt and keep them in 50 mM Tris-HCl buffer pH 8.0. Protein concentrations were determined using Bradford Reagent (Amresco, Solon, Ohio), following the manufacturer's instructions. Proteins were analyzed by SDS-PAGE using standard methods.

For enzyme co-localization experiments, purified EutM-SpyCatcher was dialyzed against ammonium chloride buffer (pH 8.7, 2M), concentrated to 20 mg/ml and the pre-formed scaffolds stored at 4° C. until use.

Cargo Proteins Expression and Purification

For cultures expressing His-tagged GFP, SpyTag-GFP, GFP-SpyTag in the pET28a backbone, cells were grown overnight at 37° C. in LB supplemented with 30 µg/ml kanamycin. These overnight cultures were diluted 100-fold, grown to an OD of $A_{600}$=0.4-0.6 and protein expressed induced with 0.5 mM IPTG at 30° C. for six hours. For His-tagged AA-ADH and AmDH (with or without SpyTag), proteins were also expressed in E. coli C2566. A single colony was inoculated in LB (30 µg/ml Kan) and grown overnight at 37° C. to seed a larger culture (700 ml) with a 1:100 inoculum. Protein expression was induced with 0.5 mM IPTG at an OD of $A_{600}$=0.6. Cultures were grown for 24 hours at 170 rpm and 20° C. until cells were harvested, centrifuged and washed with PBS (pH7.4). Pellets were frozen and stored at −20° C. For purification cells were resuspended in lysis buffer (20 mM imidazole, 50 mM $KH_2PO_4$, 300 mM NaCl, and pH 8.0) and disrupted by sonication (30 min, power 50%, pulse on 20 s, and pulse off 40 s). Protein purification from the cell lysate followed the procedure described above.

In Vitro Formation of EutM Scaffolds

In Vitro Characterization of SpyTag-Spycatcher Assisted Cargo Loading on EutM Scaffolds Amide bond formation between purified protein and peptide binding partners was first monitored by SDS-PAGE. To demonstrate covalent reconstitution, proteins were at a 1:1 molar ratio (at 10 µM each) mixed in PBS pH 7.4 at 25° C. for different times. To stop reactions, samples were heated in SDS loading buffer at 95° C. for 10 minutes. SDS-PAGE was performed on 15% polyacrylamide gels and stained with Blue Coomassie stain and band intensities were quantified using ODYSSEY Fc imaging system (LI-COR). The in vitro reconstitution of SpyTagged ADH and AmDH with EutM-SpyCatcher scaffolds were also as following the same procedure.

For imaging of cargo loading onto EutM scaffolds, purified GFP, SpyTag-GFP, GFP-SpyTag (each at 1 mg/ml) were mixed with an equal volume of EutM-Spycatcher scaffolds (1.5 mg/ml) in Bis-tris buffer pH7, respectively. The mixtures were kept for 30 min at RT prior to pipetting 10 µl onto a slide for fluorescence emission spectroscopy.

In vitro analysis of EutM-SpyCatcher scaffold formation under different buffer conditions Purified EutM-SpyCatcher was diluted to a concentration of 0.1 mg/ml into the following buffers: 0.2 M Na Acetate (pH4/pH5), 0.2 M Bis-tris (pH6/pH7), 0.2 M Tris-HCl (pH8/pH9), 0.2 M $NH_4Cl$—$NH_3$ (pH8.7) and 2 M $NH_4Cl$—$NH_3$ (pH 8.7). The EutM-SpyCatcher protein solutions (15 ml) were then concentrated in Amicon centrifugal filters (MWCO 10K) at 3000×g and 4° C. Every 10-20 mins an aliquot was removed to monitor absorbance at 600 nm and measure protein concentration by Bradford Reagent (Amresco, Solon, Ohio). Formation of scaffolds was confirmed by TEM (example shown in FIG. 7 for EutM-SpyCatcher scaffolds at 1.5 mg/ml in 0.2 M Bis-tris buffer at pH 7.0.

Enzyme Cascade Catalysis

Enzyme Kinetics

Activity of purified SpyTagged and untagged ADH and AmDH (1 mg/ml purified enzymes) was determined using a UV-microplate reader by monitoring the change of NADH concentration at 340 nm ($\varepsilon$=6.22 $mM^{-1}$ $cm^{-1}$) in 2M ammonium chloride buffer (pH 8.7). The reactions were started by the addition of substrate (0-20 mM (S)-2-hexanol for ADH and 2-hexanone for AmDH) to the mixture and were then measured at room temperature. One unit is defined as the amount of protein that produces or consumes 1 µmol of NADH per minute. Control reactions were performed under the same conditions without enzyme. Activities were measured in triplicate with biological and technical replicates.

Enzyme Cascade Reaction

Cascade reactions were performed in ammonium chloride buffer (pH 8.7, 2 M) containing a catalytic concentration of $NAD^+$ (1 mM) in a total volume of 1.5 ml. Purified untagged and SpyTagged ADH, AmDH and EutM-SpyCatcher were mixed at different molar ratios prior to starting the reaction by the addition of 20 mM (S)-2-hexanol substrate. The ADH concentration was fixed at a 30 µM concentration. Reactions were shaken at 30° C. in an orbital shaker at 150 rpm for 12-48 hours. At different time intervals, small aliquots (220 µL) of reaction mixture were taken, treated with treated with KOH (10 N, 80 µL) and extracted with EtOAc (300 µL). The organic phase was analyzed by GC-FID to quantify alcohol substrate, ketone intermediate and amine product levels. For initial optimization and testing of the cascade reaction, reactions were performed in a small scale for real-time spectrophotometric monitoring of NADH at 340 nm.

GC Analysis

Conversion of (S)-2-hexanol into the 2-hexanone and (R)-2-aminohexane measured by gas chromatography using an Agilent 7890A GC systems, equipped with an FID detector and using an Agilent J&W DB-1701 column (30 m, 250 µm, 0.1 µm). Helium was used as carrier gas and ethyl acetate (EtOAc) was used as solvent. Gas chromatography analysis was performed with the following parameters: injector 250° C.; constant pressure 14.60 psi; temperature program: 60° C./hold 6.5 min; 100° C./rate 20° C. $min^{-1}$/ hold 1 min; 280° C./rate 20° C. $min^{-1}$/hold 1 minute. The conversation rate was obtained from consumed substrate hexanol and product 2-aminohexane, which quantified by standard samples. All the standard samples were purchased from Sigma-Aldrich (St. Louis, Mo.).

EutM Toolbox

Bioinformatic Identification of EutM Homologs

More than five hundred putative EutM homologs were identified using the Basic Local Alignment Search Tool (BLAST; NCBI) with the Salmonella enterica EutM (EutM_SE) (NP_461400) protein sequence as the query. An expect threshold of one was used in the BLAST search; all homologs returned by the search has E-values less than 8×10−29. Duplicate or incomplete protein sequences, or sequences from organisms not identified to species, were removed from further analyses, leaving a total of 294 protein sequences for EutM homologs. From this group, sequences from 51 bacteria isolated from extreme environments suggesting adaptation of their proteins to conditions relevant for conditions under which biocatalytic reactions are performed (e.g., the species is known to be able to survive at extreme temperature, pH, salinity, or pressure) were phylogenetically analyzed. The Molecular Evolution Genetic Analysis version 7 (MEGA7; Kumar et al., 2016. *Mol Biol Evol* 33(7): 1870-1874) program was used to generate sequence alignments. Phylogenetic trees were constructed in MEGA7 by inferring evolutionary history using the Maximum Likelihood method, with the structurally distinct *Clostridium difficile* EutS (PDB: 4AXI) as an outgroup. A sampling of 13 homologs, including the *S. enterica* EutM, from across the observed phylogenetic clades were selected, favoring again the selection of bacteria from unusual environments (e.g., the ability to grow at extreme temperatures or in high salinity environments) suggesting that the proteins will likely be highly stable and robust under industrially relevant conditions. Sequences and accession numbers of the 12 selected EutM homologs in addition to EutM_SE are shown in Table 3.

Structural Modeling of EutM Homologs

Structural models of EutM homologs (FIG. 1, Table 3) were generated using the SWISS-MODEL (Biasini et al., 2014. *Nucleic Acids Res* 42 (Web Server issue): W252-258) web interface using as templates the crystal structures of EutM (PDB: 3MPW) from *Escherichia coli* for Eut DP, BM, MH, PH, SE, and TL; EutM (PDB: 4AXJ) from *Clostridium difficile* for EutM AM, AT, DA, FG, and SA; and PduA (PDB: 4P7T) from *Citrobacter freundii* for Eut CT, DT, and TS. The templates were chosen by SWISS-MODEL as the most appropriate based on sequence identity. PyMOL Molecular Graphics System, version 1.6 (Schrödinger, LLC, Cambridge, Mass.) was used to visualize the models and to generate predicted electrostatic potential maps for surface renderings of modeled structures of EutM homologs.

TABLE 1

List of plasmids and strains.

| Name | Description | Source |
|---|---|---|
| E. coli TOP10 | For plasmid construction | ^ |
| E. coli C2566 | fhuA2 lacZ::T7 gene1 [lon] ompT gal sulA11 R(mcr-73::miniTn10--Tet$^S$)2 [dcm] R(zgb-210::Tn10--Tet$^S$) endA1 Δ(mcrC-mrr)114::IS10 | # |
| pUCBB | BioBrick™ compatible pUC vector | 1 |
| pUCBB-pCT5-ntH6-eGFP | pUCBB vector with cumate inducible $P_{Q5}$ promoter, 6xHis-GFP, $P_{Q5}$ promoter, Amp$^r$ | 4 |
| pCT5BB | Derived from pUCBB-pCT5-ntH6-eGFP by removing a BamHI site and replacing 6xHis-GFP with the BioBrickTm compatible multiple cloning site from pUCBB, $P_{Q5}$ promoter, Amp$^r$ | This study |
| pCT5BB-EutM_SE | EutM_SE cloned into pCT55B, $P_{Q5}$ promoter, Amp$^r$ | This study |
| pCT5BB-EutM_XY | EuM_XY: His-GS_EutM homologs (DP, PH, TL, AM, AT, CT, DA, DT, FG, MN, SA, TS) containing N-terminal 6xHis tag followed by a 6xGS linker cloned into the BamHI and NotI sites of pCT5BB, $P_{Q5}$ promoter, Amp$^r$ | This study |
| pCT5BB_EutS-mCherryEutM | EutS and mCherryEutM (N-terminal fusion of mCherry to EutM) cloned into pCT5BB as two individual expression cassettes each with their own $P_{Q5}$ promoter and terminator from pCT55BB, $P_{Q5}$ promoter, Amp$^r$ | This study |
| pCT5BB-EutS-mCherryEutM_orthogonal peptide tags | C-terminus of mCherryEutM in pCT55_EutS_mCherryEutM translationally fused with orthogonal peptide sequences (sequences in Supplementary Information S1), $P_{Q5}$ promoter, Amp$^r$ | This study |
| pCT5BB-EM | EutM_SE containing a N-terminal 6xHis tag fused via a GS-linker to generate N-His-GS-EutM (EM), $P_{Q5}$ promoter, Amp$^r$ | This study |
| pCT5BB-EMSC | Fusion protein of N-His-GS-EutM to a SpyCatcher domain via a GS linker to generate: N-His-GS-EutM-GS-SpyCatcher (EMSC), $P_{Q5}$ promoter, Amp$^r$ | This study |
| pCT5BB-SpyCatcher | Derived from pCT5BB-EMSC by deleting EutM, $P_{Q5}$ promoter, Amp$^r$ | This study |
| pCT5BB-EMSC::SpyTag-eGFP | Translational fusion of SpyTag-GFP directly downstream of EMSC, $P_{Q5}$ promoter, Amp$^r$ | This study |
| pBBRBB-eGFP | GFP, constitutive lac promoter, Km$^r$ | 1 |
| pBBRBB-eGFP_LVA | Three amino acid LVA degradation tag fused to the C-terminus of GFP, constitutive lac promoter, Km$^r$ | 2 |
| pBBRBB-orthogonal peptide tag::GFP | N-terminal fusion orthogonal peptide tag to GFP in pBBRBB_GFP, constitutive lac promoter, Km$^r$ | This study |
| pBBRBB-orthogonal peptide tag::eGFP_LVA | Three amino acid LVA degradation tag fused to the C-terminus of GFP, constitutive lac promoter, Km$^r$ | This study |
| pBBRBB-mCherry | mCherry, constitutive lac promoter, Km$^r$ | 2, 3 |
| pBBRBB-SpyTag-eGFP | SpyTag-eGFP, constitutive lac promoter, Km$^r$ | This study |
| pBBRB-eGFP-SpyTag | GFP-SpyTag, constitutive lac promoter, Km$^r$ | This study |
| pBBRBB-SpyTag-mCherry | SpyTag-mCherry, constitutive lac promoter, Km$^r$ | This study |
| pBBRBB-mCherry-SpyTag | mCherry-SpyTag, constitutive lac promoter, Km$^r$ | This study |
| pET28a | T7 promoter, Km$^r$ (6xHis-tag downstream of MCS in pET28) | Invitrogen |
| pET28a-eGFP | N-terminal 6xHis tag followed by a thrombin cleavage site fused to eGFP, T7 promoter, Km$^r$ | This study |

TABLE 1-continued

List of plasmids and strains.

| Name | Description | Source |
| --- | --- | --- |
| pET28a-SpyTag-eGFP | N-terminal 6xHis tag followed by a thrombin cleavage site and GS linker (N-His-thrombin-GS) fused to SpyTag-eGFP, T7 promoter, Km$^r$ | This study |
| pET28a-eGFP-SpyTag | N-His-thrombin-GS fused to eGFP-SpyTag, T7 promoter, Km$^r$ | This study |
| pET28a-AA-ADH | N-His-thrombin-GS fused to AA-ADH from *Aromatoleum aromaticum*, T7 promoter, Km$^r$ | This study |
| pET28a-Ch1-AmDH | N-His-thrombin-GS fused to Ch1-AmDH chimera (chimera of PheDH from *Bacillus badius* and LeuDH from *Bacillus stearothermophilus*), T7 promoter, Km$^r$ | This study |
| pET28a-SpyTag-AA-ADH | N-His-thrombin-GS-SpyTag fused to the N-terminus of AA-ADH, T7 promoter, Km$^r$ | This study |
| pET28a-AA-ADH-SpyTag | SpyTag fused to C-terminus of N-His-thrombin-GS-AA-ADH, T7 promoter, Km$^r$ | This study |
| pET28a-SpyTag-Ch1-AmDH | N-His-thrombin-GS-SpyTag fused to the N-terminus of Ch1-AmDH, T7 promoter, Km$^r$ | This study |
| pET28a-Ch1-AmDH-SpyTag | SpyTag fused to C-terminus of N-His-thrombin-GS-Ch1-AmDH, T7 promoter, Km$^r$ | This study |

^ Invitrogen, Carlsbad, CA.
New England BioLabs, Inc., Ipswich, MA.
1- Vick et al., 2011. *Appl Microbiol Biotechnol* 92(6): 1275-1286.
2- Quin et al., 2016. *Appl Microbiol Biotechnol* 100(21): 9187-9200.
3- Held et al., 2016. *Sci Rep* 6: 24359.
4- Vick et al., 2015. *Appl Environ Microbiol* 81(4): 1406-1416.

TABLE 2

List of sequences for EutM_SE scaffolds, fluorescent cargo, and enzyme cargo.

SpyCatcher

GDSATHIKFS KRDEDGKELA GATMELRDSS GKTISTWISD GQVKDFYLYP GKYTFVETAA PDGYEVATAI TFTVNEQGQV
TVNG(SEQ ID NO: 1)

GGCGATAGTG CTACCCATAT TAAATTCTCA AAACGTGATG AGGACGGCAA AGAGTTAGCT GGTGCAACTA TGGAGTTGCG
TGATTCATCT GGTAAAACTA TTAGTACATG GATTTCAGAT GGACAAGTGA AAGATTTCTA CCTGTATCCA GGAAAATATA
CATTTGTCGA AACCGCAGCA CCAGACGGTT ATGAGGTAGC AACTGCTATT ACCTTTACAG TTAATGAGCA AGGTCAGGTT
ACTGTAAATG GCTGA(SEQ ID NO: 2)

N-SpyTag

AHIVMVDAYK PT(SEQ ID NO: 3)

GCCCACATCG TGATGGTGGA CGCCTACAAG CCGACGAAG(SEQ ID NO: 4)

C-SpyTag

AHIVMVDAYK PT(SEQ ID NO: 5)

GCCCACATCG TGATGGTGGA TGCCTACAAA CCTACG(SEQ ID NO: 6)

GFP

ATGGTGAGCA AGGGCGAGGA GCTGTTCACC GGGGTGGTGC CCATCCTGGT CGAGCTGGAC GGCGACGTAA ACGGCCACAA
GTTCAGCGTG TCCGGCGAGG GCGAGGGCGA TGCCACCTAC GGCAAGCTGA CCCTGAAGTT CATCTGCACC ACCGGCAAGC
TGCCCGTGCC CTGGCCCACC CTCGTGACCA CCCTGACCTA CGGCGTGCAG TGCTTCAGCC GCTACCCCGA CCACATGAAG
CAGCACGACT TCTTCAAGTC CGCCATGCCC GAAGGCTACG TCCAGGAGCG CACCATCTTC TTCAAGGACG ACGGCAACTA
CAAGACCCGC GCCGAGGTGA AGTTCGAGGG CGACACCCTG GTGAACCGCA TCGAGCTGAA GGGCATCGAC TTCAAGGAGG
ACGGCAACAT CCTGGGGCAC AAGCTGGAGT ACAACTACAA CAGCCACAAC GTCTATATCA TGGCCGACAA GCAGAAGAAC
GGCATCAAGG TGAACTTCAA GATCCGCCAC AACATCGAGG ACGGCAGCGT GCAGCTCGCC GACCACTACC AGCAGAACAC
CCCCATCGGC GACGGCCCCG TGCTGCTGCC CGACAACCAC TACCTGAGCA CCCAGTCCGC CCTGAGCAAA GACCCCAACG
AGAAGCGCGA TCACATGGTC CTGCTGGAGT TCGTGACCGC CGCCGGGATC ACTCTCGGCA TGGACGAGCT GTACAAGTAA
(SEQ ID NO: 7)

MVSKGEELFT GVVPILVELD GDVNGHKFSV SGEGEGDATY GKLTLKFICT TGKLPVPWPT LVTTLTYGVQ CFSRYPDHMK
QHDFFKSAMP EGYVQERTIF FKDDGNYKTR AEVKFEGDTL VNRIELKGID FKEDGNILGH KLEYNYNSHN VYIMADKQKN
GIKVNFKIRH NIEDGSVQLA DHYQQNTPIG DGPVLLPDNH YLSTQSALSK DPNEKRDHMV LLEFVTAAGI TLGMDELYK
(SEQ ID NO: 8)

mCherry

ATGGTGAGCA AGGGCGAGGA GGATAACATG GCCATCATCA AGGAGTTCAT GCGCTTCAAG GTGCACATGG AGGGCTCCGT
GAACGGCCAC GAGTTCGAGA TCGAGGGCGA GGGCGAGGGC CGCCCCTACG AGGGCACCCA GACCGCCAAG CTGAAGGTGA

TABLE 2-continued

List of sequences for EutM_SE scaffolds, fluorescent cargo, and enzyme cargo.

CCAAGGGTGG CCCCCTGCCC TTCGCCTGGG ACATCCTGTC CCCTCAGTTC ATGTACGGCT CCAAGGCCTA CGTGAAGCAC
CCCGCCGACA TCCCCGACTA CTTGAAGCTG TCCTTCCCCG AGGGCTTCAA GTGGGAGCGC GTGATGAACT TCGAGGACGG
CGGCGTGGTG ACCGTGACCC AGGACTCCTC CCTGCAGGAC GGCGAGTTCA TCTACAAGGT GAAGCTGCGC GGCACCAACT
TCCCCTCCGA CGGCCCCGTA ATGCAGAAGA AGACCATGGG CTGGGAGGCC TCCTCCGAGC GGATGTACCC CGAGGACGGC
GCCCTGAAGG GCGAGATCAA GCAGAGGCTG AAGCTGAAGG ACGGCGGCCA CTACGACGCT GAGGTCAAGA CCACCTACAA
GGCCAAGAAG CCCGTGCAGC TGCCCGGCGC CTACAACGTC AACATCAAGT TGGACATCAC CTCCCACAAC GAGGACTACA
CCATCGTGGA ACAGTACGAA CGCGCCGAGG CCGCCACTC CACCGGCGGC ATGGACGAGC TGTACAAGTA A(SEQ ID NO: 9)

MVSKGEEDNM AIIKEFMRFK VHMEGSVNGH EFEIEGEGEG RPYEGTQTAK LKVTKGGPLP FAWDILSPQF MYGSKAYVKH
PADIPDYLKL SFPEGFKWER VMNFEDGGVV TVTQDSSLQD GEFIYKVKLR GTNFPSDGPV MQKKTMGWEA SSERMYPEDG
ALKGEIKQRL KLKDGGHYDA EVKTTYKAKK PVQLPGAYNV NIKLDITSHN EDYTIVEQYE RAEGRHSTGG MDELYKAAAS
SITITITDSP YASVRYFTPH VLVNFRTCSL V(SEQ ID NO: 10)

N-SpyTag-GFP or mcherry: N-His-thrombin-GS-SpyTag-GS-[GFP/mCherry]

ATGGGCAGCA GC-CATCATCA TCATCATCAC- AGCAGCGGCC TGGTGCCGCG CGGCAGCCAT ATG-ATGGGCA
GCAGCGGC-GC CCACATCGTG ATGGTGGACG CCTACAAGCC GACGAAG-GGT TCAGGGGAT CCGGTGTCGA
C-[*GFP/mCherry](SEQ ID NO: 11)

MGSS-HHHHHH- SSGLVPRGSH MM-MGSSG-AHI VMVDAYKPT-K GSGGSGVD(SEQ ID NO: 12)
*includes ATG GFP or mCherry-C-SpyTag: N-His-thrombin-[GFP/mCherry]-GS-SpyTag ATGGGCAGCA G-CCATCATCA TCATCATCAC- AGCAGCGGCC TGGTGCCGCG CGGCAGCCAT ATG-[GFP/mCherry*]-
GTCGACTCCG GATCAGGATC CGGCGGC-GCC CACATCGTGA TGGTGGATGC CTACAAACCT ACGTAA(SEQ ID NO: 13)

MGSS-HHHHHH- SSGLVPRGSH M-[GFP/mCherry]-VDSGSGSGG- AHIVMVDAYK PT(SEQ ID NO: 14)
*excludes TAA EutM_SE ATGGAAGCAT TAGGAATGAT TGAAACCCGG GGCCTGGTTG CGCTGATTGA GGCCTCCGAT GCGATGGTAA AAGCCGCGCG
CGTGAAGCTG GTCGGCGTGA AGCAGATTGG CGGTGGCCTG TGTACTGCCA TGGTGCGTGG CGATGTGGCG GCGTGCAAAG
CCGCAACCGA TGCTGGCGCC GCTGCGGCGC AGCGCATTGG CGAGTTGGTC TCCGTACACG TGATTCCACG CCCGCACGGC
GATCTGGAAG AAGTGTTCCC GATCAGCTTC AAAGGCGACA GCAACATTTG A(SEQ ID NO: 15)

MEALGMIETR GLVALIEASD AMVKAARVKL VGVKQIGGGL CTAMVRGDVA ACKAATDAGA AAAQRIGELV SVHVIPRPHG
DLEEVFPISF KGDSNI(SEQ ID NO: 16)

EutM_SE-GS-SpyCatcher

ATGGAAGCAT TAGGAATGAT TGAAACCCGG GGCCTGGTTG CGCTGATTGA GGCCTCCGAT GCGATGGTAA AAGCCGCGCG
CGTGAAGCTG GTCGGCGTGA AGCAGATTGG CGGTGGCCTG TGTACTGCCA TGGTGCGTGG CGATGTGGCG GCGTGCAAAG
CCGCAACCGA TGCTGGCGCC GCTGCGGCGC AGCGCATTGG CGAGTTGGTC TCCGTACACG TGATTCCACG CCCGCACGGC
GATCTGGAAG AAGTGTTCCC GATCAGCTTC AAAGGCGACA GCAACATT-GT CGACGGGAGT GGTGGCAGCG GA-GGCGATAG
TGCTACCCAT ATTAAATTCT CAAAACGTGA TGAGGACGGC AAAGAGTTAG CTGGTGCAAC TATGGAGTTG CGTGATTCAT
CTGGTAAAAC TATTAGTACA TGGATTTCAG ATGGACAAGT GAAAGATTTC TACCTGTATC CAGGAAAATA TACATTTGTC
GAAACCGCAG CACCAGACGG TTATGAGGTA GCAACTGCTA TTACCTTTAC AGTTAATGAG CAAGGTCAGG TTACTGTAAA
TGGCTGA(SEQ ID NO: 17)

MEALGMIETR GLVALIEASD AMVKAARVKL VGVKQIGGGL CTAMVRGDVA ACKAATDAGA AAAQRIGELV SVHVIPRPHG
DLEEVFPISF KGDSNIVD-GS GGSG-GDSATH IKFSKRDEDG KELAGATMEL RDSSGKTIST WISDGQVKDF YLYPGKYTFV
ETAAPDGYEV ATAITFTVNE QGQVIVNG(SEQ ID NO: 18)

N-His-GS-[EutM_SE/EutM_SE-GS-SpyCatcher]

ATG-CATCATC ATCACCACCA C-GGTTCTGGT TCTGGTTCTG GTTCTGGTTC TGGTTCT[*EutM_SE/EutM_SE-
GS_SpyCatcher](SEQ ID NO: 19)

M-HHHHHH-GSG SGSGSGSGS-[*EutM_SE/EutM_SE-GS_SpyCatcher](SEQ ID NO: 20)
*without ATG AA-ADH from Aromatoleum aromaticum ATGACACAAA GACTGAAAGA TAAACTTGCC GTCATTACAG GCGGAGCTAA TGGAATTGGA CGCGCTATAG CGGAAAGATT
TGCTGTAGAA GGCGCTGATA TCGCTATCGC AGACCTTGTA CCGGCCCCTG AGGCGGAGGC AGCCATCCGC AATCTTGGCC
GGCGTGTTTT AACAGTGAAA TGTGATGTTA GCCAGCCAGG GGACGTCGAA GCGTTCGGGA AACAGGTTAT CTCGACGTTC
GGGAGATGTG ATATTCTTGT CAACAATGCA GGTATATATC CTTTGATTCC GTTTGACGAG CTTACATTCG AGCAATGGAA
GAAAACATTT GAGATCAATG TCGATAGCGG GTTCTTGATG GCTAAGCCT TTGTACCAGG AATGAAGCGC AATGGCTGGG
GGCGTATCAT TAACTTAACG AGCACTACCT ATTGGCTTAA AATAGAAGCG TATACCCATT ATATAAGTAC GAAGGCGGCA
AACATTGGAT TTACCCGCGC CCTTGCCTCC GACCTGGGCA AAGATGGTAT AACCGTGAAT GCCATAGCCC CCTCGTTGGT
TAGAACGGCG ACTACTGAAG CATCTGCACT GAGCGCAATG TTTGACTGT TACCCAATAT GTTACAGGCT ATCCCACGTC
TGCAAGTCCC ACTTGATCTG ACAGGAGCGG CTGCTTTTTT GGCATCCGAT GACGCTTCGT TCATTACAGG ACAAACCCTT
GCAGTAGACG GTGGGATGGT CCGTCATTAA (SEQ ID NO: 21)

MTQRLKDKLA VITGGANGIG RAIAERFAVE GADIAIADLV PAPEAEAAIR NLGRRVLTVK CDVSQPGDVE AFGKQVISTF
GRCDILVNNA GIYPLIPFDE LTFEQWKKTF EINVDSGFLM AKAFVPGMKR NGWGRIINLT STTYWLKIEA YTHYISTKAA

TABLE 2-continued

List of sequences for EutM_SE scaffolds, fluorescent cargo, and enzyme cargo.

NIGFTRALAS DLGKDGITVN AIAPSLVRTA TTEASALSAM FDVLPNMLQA IPRLQVPLDL TGAAAFLASD DASFITGQTL
AVDGGMVRH (SEQ ID NO: 22)

N_His_thrombin_SpyTag-GS-AA-ADH

ATGGGCAGCA GC-CATCATCA TCATCATCAC- AGCAGCGGCC TGGTGCCGCG CGGCAGCCAT ATGATG-GGCA
GCAGCGGC-GC CCACATCGTG ATGGTGGACG CCTACAAGCC GACGAAG-GGT TCAGGGGGAT CCGGTGTCGA
C-ATGCACAA AGACTGAAAG ATAAACTTGC CGTCATTACA GGCGGAGCTA ATGGAATTGG ACGCGCTATA GCGGAAAGAT
TTGCTGTAGA AGGCGCTGAT ATCGCTATCG CAGACCTTGT ACCGGCCCCT GAGGCGGAGG CAGCCATCCG CAATCTTGGC
CGGCGTGTTT TAACAGTGAA ATGTGATGTT AGCCAGCCAG GGGACGTCGA AGCGTTCGGG AAACAGGTTA TCTCGACGTT
CGGGAGATGT GATATTCTTG TCAACAATGC GGGTATATAT CCTTTGATTC CGTTTGACGA GCTTACATTC GAGCAATGGA
AGAAAACATT TGAGATCAAT GTCGATAGCG GGTTCTTGAT GGCTAAAGCC TTTGTACCAG GAATGAAGCG CAATGGCTGG
GGGCGTATCA TTAACTTAAC GAGCACTACC TATTGGCTTA AAATAGAAGC GTATACCCAT TATATAAGTA CGAAGGCGGC
AAACATTGGA TTTACCCGCG CCCTTGCCTC CGACCTGGGC AAAGATGGTA TAACCGTGAA TGCCATAGCC CCTCGTTGG
TTAGAACGGC GACTACTGAA GCATCTGCAC TGAGCGCAAT GTTTGACGTG TTACCCAATA TGTTACAGGC TATCCCACGT
CTGCAAGTCC CACTTGATCT GACAGGAGCG GCTGCTTTTT TGGCATCCGA TGACGCTTCG TTCATTACAG GACAAACCCT
TGCAGTAGAC GGTGGGATGG TCCGTCATTA A (SEQ ID NO: 23)

MGSS-HHHHHH- SSGLVPRGSH MM-GSSG-AHIV MVDAYKPTK-G SGGSGVD-MTQ RLKDKLAVIT GGANGIGRAI
AERFAVEGAD IAIADLVPAP EAEAAIRNLG RRVLTVKCDV SQPGDVEAFG KQVISTFGRC DILVNNAGIY PLIPFDELTF
EQWKKTFEIN VDSGFLMAKA FVPGMKRNGW GRIINLTSTT YWLKIEAYTH YISTKAANIG FTRALASDLG KDGITVNAIA
PSLVRTATTE ASALSAMFDV LPNMLQAIPR LQVPLDLTGA AAFLASDDAS FITGQTLAVD GGMVRH (SEQ ID NO: 24)

N_His_thrombin_AA_ADH_GS_SpyTag

ATGGGCAGCA GC-CATCATCA TCATCATCAC- AGCAGCGGCC TGGTGCCGCG CGGCAGCCAT ATG-ATGACAC
AAAGACTGAA AGATAAACTT GCCGTCATTA CAGGCGGAGC TAATGGAATT GGACGCGCTA TAGCGGAAAG ATTTGCTGTA
GAAGGCGCTG ATATCGCTAT CGCAGACCTT GTACCGGCCC CTGAGGCGGA GGCAGCCATC CGCAATCTTG GCCGGCGTGT
TTTAACAGTG AAATGTGATG TTAGCCAGCC AGGGGACGTC GAAGCGTTCG GAAACAGGT TATCTCGACG TTCGGGAGAT
GTGATATTCT TGTCAACAAT GCGGGTATAT ATCCTTTGAT TCCGTTTGAC GAGCTTACAT CGAGCAATG GAAGAAAACA
TTTGAGATCA ATGTCGATAG CGGGTTCTTG ATGGCTAAAG CCTTTGTACC AGGAATGAAG CGCAATGGCT GGGGGCGTAT
CATTAACTTA ACGAGCACTA CCTATTGGCT TAAAATAGAA GCGTATACCC ATTATATAAG TACGAAGGCG GCAAACATTG
GATTTACCCG CGCCCTTGCC TCCGACCTGG GCAAAGATGG TATAACCGTG AATGCCATAG CCCCTCGTT GGTTAGAACG
GCGACTACTG AAGCATCTGC ACTGAGCGCA ATGTTTGACG TGTTACCCAA TATGTTACAG GCTATCCCAC GTCTGCAAGT
CCCACTTGAT CTGACAGGAG CGGCTGCTTT TTTGGCATCC GATGACGCTT CGTTCATTAC AGGACAAACC CTTGCAGTAG
ACGGTGGGAT GGTCCGTCAT-G TCGACTCCGG ATCAGGATCC GGCGGC-GCCC ACATCGTGAT GGTGGATGCC
TACAAACCTA CGTAA (SEQ ID NO: 25)

MGSS-HHHHHH S-SGLVPRGSH M-MTQRLKDKL AVITGGANGI GRAIAERFAV EGADIAIADL VPAPEAEAAI
RNLGRRVLTV KCDVSQPGDV EAFGKQVIST FGRCDILVNN AGIYPLIPFD ELTFEQWKKT FEINVDSGFL MAKAFVPGMK
RNGWGRIINL TSTTYWLKIE AYTHYISTKA ANIGFTRALA SDLGKDGITV NAIAPSLVRT ATTEASALSA MFDVLPNMLQ
AIPRLQVPLD LTGAAAFLAS DDASFITGQT LAVDGGMVRH- VDSGSGSGG-A HIVMVDAYKP T (SEQ ID NO: 26)

Ch1-AmDH: Chimera of *Bacillus badius* Leu-DH and *Geobacillus kaustophilus* PheDH ATGTCGTTGG TGGAAAAAAC CTCCATTATT AAAGACTTCA CATTGTTCGA AAAAATGTCA GAACATGAGC AGGTAGTCTT
TTGCAACGAT CCCGCGACGG GTCTTCGGGC TATTATTGCG ATCCATGACA CGACTTTAGG GCCTGCTCTT GGCGGTTGCC
GTATGCAGCC GTATAACAGT GTAGAAGAAG CTCTCGAAGA TGCTTTGCGT TTGAGCAAGG GAATGACGTA CAGCTGCGCG
GCGTCTGACG TTGACTTCGG GGGAGGCAAA GCGGTGATAA TCGGGGATCC TCAAAAGGAT AAAAGCCCTG AGTTGTTTCG
TGCATTTGGG CAATTTGTAG ACAGCCTTGG CGGTAGATTT TACACAGGCA CTGATATGGG CACTAACATG GAGGACTTTA
TCCATGCCAT GAAGGAAACT AACTGCATCG TCGGAGTCCC AGAGGCCTAT GGGTCTAGCG GTAACCCCTC CCCCGCGACA
GCATATGGCG TGTATCGTGG AATGAAGGCT GCTGCCAAGG AAGCGTTCGG ATCCGACTCC TTGGAAGGTA AGGTAGTGGC
GGTTCAAGGC GTCGGGAATG TCGCGTATCA TCTGTGTCGG CATCTGCATG AGGAAGGAGC CAAGTTAATA GTTACGGACA
TAAACAAGGA AGCCGTGGCT CGCGCCGTAG AAGAATTCGG GGCAAAGGCC GTCGATCCTA ATGACATCTA TGGCGTCGAA
TGCGACATCT TCGCCCCATG TGCCCTGGGT GGTATAATAA ATGATCAAAC AATTCCACAG CTTAAAGCAA AAGTGATCGC
GGGATCTGCA TTAAACCAAC TGAAAGAGCC CCGTCACGGC GACATGATTC ACGAAATGGG GATAGTTTAT GCCCCTGACT
ATGTCATCAA CGCGGGAGGA TGTATCAATG TAGCGGATGA ACTTTATGGA TACAATCGTG AACGCGCAAT GAAAAAGATC
GAGCAAATCT ATGACAATAT AGAAAAAGTC TTCGCAATCG CAAAACGTGA TAATATACCC ACTTATGTCG CCGCCGATCG
TATGGCTGAG AACGGATAG AGACTATGCG TAAGGCACGG AGTCAATTTC TTCAGAACGG GCATCATATT TTGAGCCGCA
GAAGAGCGAG ATA A (SEQ ID NO: 27)

MSLVEKTSII KDFTLFEKMS EHEQVVFCND PATGLRAIIA IHDTTLGPAL GGCRMQPYNS VEEALEDALR LSKGMTYSCA
ASDVDFGGGK AVIIGDPQKD KSPELFRAFG QFVDSLGGRF YTGTDMGTNM EDFIHAMKET NCIVGVPEAY GSSGNPSPAT
AYGVYRGMKA AKEAFGSDS LEGKVVAVQG VGNVAYHLCR HLHEEGAKLI VTDINKEAVA RAVEEFGAKA VDPNDIYGVE
CDIFAPCALG GIINDQTIPQ LKAKVIAGSA LNQLKEPRHG DMIHEMGIVY APDYVINAGG CINVADELYG YNRERAMKKI
EQIYDNIEKV FAIAKRDNIP TYVAADRMAE ERIETMRKAR SQFLQNGHHI LSRRRAR(SEQ ID NO: 28)

N-His-thrombin-SpyTag-GS-Ch1-AmDH

ATGGGCAGCA GC-CATCATCA TCATCATCAC- AGCAGCGGCC TGGTGCCGCG CGGCAGCCAT ATGATGGGCA
GCAGCGGC-GC CCACATCGTG ATGGTGGACG CCTACAAGCC GACGAAG-GGT TCAGGGGGAT CCGGTGTCGA
C-ATGTCGTTG GTGGAAAAAA CCTCCATTAT TAAAGACTTC ACATTGTTCG AAAAAATGTC AGAACATGAG CAGGTAGTCT
TTTGCAACGA TCCCGCGACG GGTCTTCGGG CTATTATTGC GATCCATGAC ACGACTTTAG GGCCTGCTCT TGGCGGTTGC
CGTATGCAGC CGTATAACAG TGTAGAAGAA GCTCTGGAAG ATGCTTTGCG TTTGAGCAAA GGAATGACGT ACAGCTGCGC
GGCGTCTGAC GTTGACTTCG GGGGAGGCAA AGCGGTGATA TCGGGGATC TCAAAAGGA TAAAAGCCCT GAGTTGTTTC
GTGCATTTGG GCAATTTGTA GACAGCCTTG CGGTAGATT TACACAGGC ACTGATATGG GCACTAACAT GGAGGACTTT
ATCCATGCCA TGAAGGAAAC TAACTGCATC GTCGGAGTCC CAGAGGCCTA TGGGTCTAGC GGTAACCCCT CCCCCGCGAC
AGCATATGGC GTGTATCGTG GAATGAAGGC TGCTGCCAAG GAAGCGTTCG GATCCGACTC CTTGGAAGGT AAGGTAGTGG

TABLE 2-continued

List of sequences for EutM_SE scaffolds, fluorescent cargo, and enzyme cargo.

CGGTTCAAGG CGTCGGGAAT GTCGCGTATC ATCTGTGTCG GCATCTGCAT GAGGAAGGAG CCAAGTTAAT AGTTACGGAC
ATAAACAAGG AAGCCGTGGC TCGCGCCGTA GAAGAATTCG GGGCAAAGGC CGTCGATCCT AATGACATCT ATGGCGTCGA
ATGCGACATC TTCGCCCCAT GTGCCCTGGG TGGTATAATA AATGACTAAA CAATTCCACA GCTTAAAGCA AAAGTGATCG
CGGGATCTGC ATTAAACCAA CTGAAAGAGC CCCGTCACGG CGACATGATT CACGAAATGG GGATAGTTTA TGCCCCTGAC
TATGTCATCA ACGCGGGAGG ATGTATCAAT GTAGCGGATG AACTTTATGG ATACAATCGT GAACGCGCAA TGAAAAAGAT
CGAGCAAATC TATGACAATA TAGAAAAAGT CTTCGCAATC GCAAACGTG ATAATATACC CACTTATGTC GCCGCCGATC
GTATGGCTGA GGAACGGATA GAGACTATGC GTAAGGCACG GAGTCAATTT CTTCAGAACG GCATCATAT TTTGAGCCGC
AGAAGAGCGA GATAA(SEQ ID NO: 29)

MGSS-HHHHHH- SSGLVPRGSH MMGSSG-AHIV MVDAYKPTK-G SGGSGVD-MSL VEKTSIIKDF TLFEKMSEHE
QVVFCNDPAT GLRAIIAIHD TTLGPALGGC RMQPYNSVEE ALEDALRLSK GMTYSCAASD VDFGGGKAVI IGDPQKDKSP
ELFRAFGQFV DSLGGRFYTG TDMGTNMEDF IHAMKETNCI VGVPEAYGSS GNPSPATAYG VYRGMKAAAK EAFGSDSLEG
KVVAVQGVGN VAYHLCRHLH EEGAKLIVTD INKEAVARAV EEFGAKAVDP NDIYGVECDI FAPCALGGII NDQTIPQLKA
KVIAGSALNQ LKEPRHGDMI HEMGIVYAPD YVINAGGCIN VADELYGYNR ERAMKKIEQI YDNIEKVFAI AKRDNIPTYV
AADRMAEERI ETMRKARSQF LQNGHHILSR RRAR(SEQ ID NO: 30)

N-His-thrombin-Ch1-AmDH-GS-SpyTag

ATGGGCAGCA GC-CATCATCA TCATCATCAC- AGCAGCGGCC TGGTGCCGCG CGGCAGCCAT ATG-ATGTCGT
TGGTGGAAAA AACCTCCATT ATTAAAGACT TCACTGTTGTT CGAAAAAATG TCAGAACATG AGCAGGTAGT CTTTTGCAAC
GATCCCGCGA CGGGTCTTCG GGCTATTATT GCGATCCATG ACACGACTTT AGGGCCTGCT CTTGGCGGTT GCCGTATGCA
GCCGTATAAC AGTGTAGAAG AAGCTCTGGA AGATGCTTTG CGTTTGAGCA AAGGAATGAC GTACAGCTGC GCGGCGTCTG
ACGTTGACTT CGGGGGAGGC AAAGCGGTGA TAATCGGGGA TCCTCAAAAG GATAAAAGCC CTGAGTTGTT TCGTGCATTT
GGGCAATTTG TAGACAGCCT TGGCGGTAGA TTTTACACAG GCACTGATAT GGGCACTAAC ATGGAGGACT TTATCCATGC
CATGAAGGAA ACTAACTGCA TCGTCGGAGT CCCAGAGGCC TATGGGTCTA GCGGTAACCC CTCCCCCGCG ACAGCATATG
GCGTGTATCG TGGAATGAAG GCTGCTGCCA AGGAAGCGTT CGGATCCGAC TCCTTGGAAG GTAAGGTAGT GGCGGTTCAA
GGCGTCGGGA ATGTCGCGTA TCATCTGTGT CGGCATCTGC ATGAGGAAGG AGCCAAGTTA ATAGTTACGG ACATAAACAA
GGAAGCCGTG GCTCGCGCCG TAGAAGAATT CGGGGCAAAG GCCGTCGATC CTAATGACAT CTATGGCGTC GAATGCGACA
TCTTCGCCCC ATGTGCCCTG GGTGGTATAA TAAATGACCA AACCATTCCA CAAAAGTGAT CGCGGGATCT
GCATTAAACC AACTGAAAGA GCCCCGTCAC GGCGACATGA TTCACGAAAT GGGGATAGTT TATGCCCCTG ACTATGTCAT
CAACGCGGGA GGATGTATCA ATGTAGCGGA TGAACTTTAT GGATACAATC GTGAACGCGC AATGAAAAAG ATCGAGCAAA
TCTATGACAA TATAGAAAAA GTCTTCGCAA TCGCAAAACG TGATAATATA CCCACTTATG TCGCCGCCGA TCGTATGGCT
GAGGAACGGA TAGAGACTAT GCGTAAGGCA CGGAGTCAAT TCTTCAGAA CGGGCATCAT ATTTTGAGCC GCAGAAGAGC
GAGA-GTCGAC TCCGGATCAG GATCCGGCGG C-GCCCACATC GTGATGGTGG ATGCCTACAA ACCTACGTAA(SEQ ID NO: 31)

MGSS-HHHHHH- SSGLVPRGSH M-MSLVEKTSI IKDFTLFEKM SEHEQVVFCN DPATGLRAII AIHDTTLGPA
LGGCRMQPYN SVEEALEDAL RLSKGMTYSC AASDVDFGGG KAVIIGDPQK DKSPELFRAF GQFVDSLGGR FYTGTDMGTN
MEDFIHAMKE TNCIVGVPEA YGSSGNPSPA TAYGVYRGMK AAAKEAFGSD SLEGKVVAVQ GVGNVAYHLC RHLHEEGAKL
IVTDINKEAV ARAVEEFGAK AVDPNDIYGV ECDIFAPCAL GGIINDQTIP QLKAKVIAGS ALNQLKEPRH GDMIHEMGIV
YAPDYVINAG GCINVADELY GYNRERAMKK IEQIYDNIEK VFAIAKRDNI PTYVAADRMA EERIETMRKA RSQFLQNGHH
ILSRRRAR-VD SGSGSGG-AHI VMVDAYKPT(SEQ ID NO: 32)

"-": denotes divisions between fragments in fusion sequences

TABLE 3

Toolbox of 14 EutM homologs selected for expression and characterization. Microbial sources, accession numbers, protein sequences and coding sequences for expression in E. coli under the control of a cumate inducible $P_{QS}$ promoter on expression vector pCT5BB

| EutM | Source organism | Accession # | Protein Sequence | Expression construct | pI Mw (Da) |
|---|---|---|---|---|---|
| EutM_SE | Salmonella enterica | WP_024798609.1 | MEALGMIETR GLVALIEASD TMVKAARVKL VGVKQIGGGL CTAMVRGDVA ACKAATDAGA AAAQRIGELV SVHVIPRPHG DLEEVFPISF KGDSNI (SEQ ID NO: 33) | >His-GS-EutM_BM ATGCATCATC ATCACCACCA CGGTTCTGGT TCTGGTTCTG GTTCTGGTTC TGGTTCTGAA GCATTAGGAA TGATTGAAAC CCGGGGCCTG GTTGCGCTGA TTGAGGCCTC CGATGCGATG GTAAAAGCCG CGCGCGTGAA GCTGGTCGGC GTGAAGCAGA TTGGCGGTGG CCTGTGTACT GCCATGGTGC GTGGCGATGT GGCGGCGTGC AAAGCCGCAA CCGATGCTGG CGCCGCTGCG GCGCAGCGCA TTGGCGAGTT GGTCTCCGTA CACGTGATTC CACGCCCGCA CGGCGATCTG GAAGAAGTGT TCCCGATCAG CTTCAAAGGC GACAGCAACA TT (SEQ ID NO: 34) | 6.06 9872 |

TABLE 3-continued

Toolbox of 14 EutM homologs selected for expression and characterization. Microbial sources, accession numbers, protein sequences and coding sequences for expression in *E. coli* under the control of a cumate inducible $P_{O5}$ promoter on expression vector pCT5BB

| EutM | Source organism | Accession # | Protein Sequence | Expression construct | pI Mw (Da) |
|---|---|---|---|---|---|
| EutM_AM | *Alkaliphilus metalliredigens* | WP_011971402.1 | MAISNALGMI ETKGLVGAIE AADAMVKAAN VTLLGKEHVG GGLVTVMVRG DVGAVKAATD AGAAAAERVG ELMSVHVIPR PHGEVETILP QIKE (SEQ ID NO: 35) | >His-GS-EuM_AM ATGCATCATC ATCATCACCA CGGCAGCGGT AGCGGCAGCG GTAGCGGCAG CGGTAGCGCA CTGGGTATGA TCGAAACCAA GGGCCTGGTT GGTGCGATTG AAGCGGCGGA CGCGATGGTT AAGGCGGCGA ACGTGACCCT GCTGGGTAAA GAGCACGTGG GTGGCGGTCT GGTGACCGTT ATGGTGCGTG GCGACGTTGG TGCGGTGAAA GCGGCGACCG ATGCGGGTGC TGCGGCGGCG GAGCGTGTTG GTGAACTGAT GAGCGTTCAT GTGATCCCGC GTCCGCACGG CGAGGTGGAA ACCATTCTGC CGTAA (SEQ ID NO: 36) | 5.50 9482 |
| EutM_AT | *Aneurinibacillus terranovensis* | WP_027415023.1 | MAREINGALG MIETRGLVAS LEAADAMVKA ANVNIVGKVH VGGGIVTVLV TGDVGAVKAA TEAGSTAAQR VGEIISVHVI PRPHHELGSI LPKLEEY (SEQ ID NO: 37) | >His-GS-EutM_AT ATGCATCATC ATCATCACCA CGGCAGCGGT AGCGGCAGCG GTAGCGGCAG CGGTAGCGCA CTGGGTATGA TCGAAACCCG TGGTCTGGTG GCGAGCCTGG AGGCGGCGGA TGCGATGGTG AAGGCGGCGA ACGTTAACAT CGTGGGCAAA GTGCACGTTG GTGGCGGTAT TGTGACCGTT CTGGTGACCG GCGATGTTGG TGCGGTGAAA GCGGCGACCG AGGCGGGCAG CACCGCGGCG CAGCGTGTTG GTGAAATCAT TAGCGTTCAT GTGATCCCGC GTCCGCACCA TGAGCTGGGT AGCATTCTGC CGTAA (SEQ ID NO: 38) | 6.04 9904 |
| EutM_CT | *Caldalkali-bacillus thermarum* | WP_007505381.1 | MNESLGFIET RGFTAAIEAA DAMLKAANVE IVGSEKIGSG LVSVIVKGDV GAVKAATEVG AEAAGRVGEV IAVHVIPRPH GDIQKLLPTV KDDAV (SEQ ID NO: 39) | >His-GS-EutM_CT ATGCATCATC ATCATCACCA CGGTAGCGGC AGCGGTAGCG GCAGCGGTAG CGGCAGCGAG AGCCTGGGTT TCATCGAAAC CCGTGGCTTT ACCGCGGCGA TTGAAGCGGC GGATGCGATG CTGAAGGCGG CGAACGTTGA GATCGTGGGT AGCGAAAAAA TTGGTAGCGG CCTGGTGAGC GTTATCGTGA AGGGTGATGT TGGCGCGGTG AAAGCGGCGA CCGAGGTTGG TGCGGAAGCG GCGGGTCGTG TTGGCGAAGT GATCGCGGTT CACGTGATTC CGCGTCCGCA CGGCGACATT CAGAAGCTGC TGCCGTAA (SEQ ID NO: 40) | 5.02 9648 |
| EutM_DA | *Desulfosporosinus acidiphdus* | WP_014826595.1 | MNKTEALGLI ETKGLVGAIE AADAMVKAAN VYLIGRELVG GGLVTVMVRG DVGAVKAATD AGAAAAQRVG ELISVHVIPR PHGDVEMILP QAKKEA (SEQ ID NO: 41) | >His-GS-EutM_DA ATGCATCATC ATCATCACCA CGGCAGCGGT AGCGGCAGCG GTAGCGGCAG CGGTAGCGAG CGCTGGGCC TGATCGAAAC CAAGGGCCTG GTTGGTGCGA TTGAGGCGGC GGACGCGATG GTTAAAGCGG CGAACGTGTA CCTGATCGGT CGTGAACTGG TGGGTGGCGG TCTGGTGACC GTTATGGTTC GTGGCGACGT TGGTGCGGTG AAAGCGGCGA CCGATGCGGG TGCTGCGGCG GCGCAGCGTG TTGGCGAGCT GATCAGCGTT CACGTGATTC CGCGTCCGCA CGGCGATGTG |

TABLE 3-continued

Toolbox of 14 EutM homologs selected for expression and characterization. Microbial sources, accession numbers, protein sequences and coding sequences for expression in *E. coli* under the control of a cumate inducible P$_{O5}$promoter on expression vector pCT5BB

| EutM | Source organism | Accession # | Protein Sequence | Expression construct | pI Mw (Da) |
|---|---|---|---|---|---|
| | | | | GAAATGATTC TGCCGCAAGC GAAGAAATAA (SEQ ID NO: 42) | |
| EutM_DP | *Desulfotalea psychrophila* | WP_011190286.1 | MDSLGMIETK GLIALIEASD AMVKAARVQL VGYKQIGAGL VTAIVRGDVA ACKAATDAGA AAAARIGEVV AVHVIPRPHG DLEEVFPFKR DK (SEQ ID NO: 43) | >His-GS-EutM_DP ATGCATCATC ATCACCACCA CGGTTCTGGT TCTGGTTCTG GTTCTGGTTC TGGTTCTGAT TCATTAGGAA TGATTGAAAC TAAGGGCTTG ATCGCACTTA TTGAAGCTTC AGATGCAATG GTAAAGGCTG CTCGTGTACA ACTTGTAGGT TACAAACAAA TTGGTGCTGG TTTGGTAACT GCGATTGTTC GTGGTGATGT TGCAGCATGT AAAGCAGCAA CCGATGCAGG TGCAGCAGCA GCCGCACGTA TTGGCGAGGT GGTAGCTGTA CACGTTATTC CACGTCCACA TGGTGACCTG GAAGAAGTAT TTCCCTTCAA ACGTGACAAA TAG (SEQ ID NO: 44) | 6.72 9512 |
| EutM_DT | *Desulfotomaculum thermocisternum* | WP_027356248.1 | MTGEALGMVE TRGLVPAIEA ADAMVKAANV VLLGYEKIGS GLVTVMVRGD VGAVKAATDA GAAAAKRVGE VVSVHVIPRP HTDVEKILPA ADRK (SEQ ID NO: 45) | >His-GS-EutM_DT ATGCATCATC ATCATCACCA CGGTAGCGGC AGCGGTAGCG GCAGCGGTAG CGGCAGCGAG GCGCTGGGTA TGGTTGAAAC CCGTGGCCTG GTGCCGGCGA TTGAGGCGGC GGATGCGATG GTTAAGGCGG CGAACGTGGT TCTGCTGGGT TACGAAAAAA TTGGTAGCGG CCTGGTGACC GTTATGGTTC GTGGTGACGT TGGTGCGGTG AAAGCGGCGA CCGATGCGGG TGCTGCGGCG GCGAAACGTG TTGGCGAGGT GGTTAGCGTT CACGTGATCC CGCGTCCGCA CACCGATGTG GAAAAGATTC TGCCGTAA (SEQ ID NO: 46) | 6.72 9559 |
| EutM_FG | *Fictibacillus gelatini* | WP_026677998.1 | MSRELTALGM IETKGLVASV EAADAMVKAA NVHLVGKVHV GGGLVTVLVR GDVGAVKAAT EAGAAAAQRV GELLSVHVIP RPHNELESIL PKVETM (SEQ ID NO: 47) | >His-GS-EutM_FG ATGCATCATC ATCATCACCA CGGCAGCGGT AGCGGCAGCG GTAGCGGCAG CGGTAGCCTG ACCGCGCTGG GCATGATCGA AACCAAGGGT CTGGTTGCGA GCGTGGAAGC GGCGGATGCG ATGGTTAAGG CGGCGAACGT TCACCTGGTG GGCAAAGTGC ACGTTGGTGG CGGTCTGGTG ACCGTTCTGG TGCGTGGCGA TGTTGGTGCG GTGAAAGCGG CGACCGAGGC GGGTGCTGCG GCGGCGCAGC GTGTGGGTGA ACTGCTGAGC GTTCACGTGA TCCCGCGTCC GCACAACGAG CTGGAAAGCA TTCTGCCGTA A (SEQ ID NO: 48) | 6.40 9815 |
| EutM_MH | *Marinobacter hydrocarbono-clasticus* | WP_011784738.1 | MNEALGIIET KGLTALIEAS DAMVKAARVE LVGYKQIGSG LVTAMVRGDV AACKAATDAG AAAAQRLGEL VAVHVIPRPH GDLEAIFPIN PAVKPSGA (SEQ ID NO: 49) | >His-GS-EutM_MH ATGCATCATC ATCATCACCA CGGTAGCGGC AGCGGTAGCG GCAGCGGTAG CGGCAGCGAG GCGCTGGGTA TCATTGAAAC CAAAGGCCTG ACCGCGCTGA TTGAGGCGAG CGATGCGATG GTGAAGGCGG CGCGTGTTGA ACTGGTGGGT TACAAACAGA TTGGTAGCGG CCTGGTTACC GCGATGGTGC GTGGCGACGT | 6.05 9916 |

TABLE 3-continued

Toolbox of 14 EutM homologs selected for expression and characterization. Microbial sources, accession numbers, protein sequences and coding sequences for expression in *E. coli* under the control of a cumate inducible P$_{QS}$promoter on expression vector pCT5BB

| EutM | Source organism | Accession # | Protein Sequence | Expression construct | pI Mw (Da) |
|---|---|---|---|---|---|
| | | | | GGCGGCGTGC AAAGCGGCGA CCGATGCGGG TGCTGCGGCG GCGCAACGTC TGGGCGAGCT GGTTGCGGTT CACGTGATCC CGCGTCCGCA CGGTGATCTG GAAGCGATCT TCCCGATTAA CTAA (SEQ ID NO: 50) | |
| EutM_PH | *Psychromonas hadalis* | WP_022941754.1 | MDALGILETK GLTALIEASD AMVKAASVEL VGYQQIGSGY VTAFIRGDVA SCKAATDAGS VVAQRLGELV AVHVIPRPHQ DLEAVFPITA KK (SEQ ID NO: 51) | >His_GS-EutM-PH ATGCATCATC ATCACCACCA CGGTTCTGGT TCTGGTTCTG GTTCTGGTTC TGGTTCTGAC GCTTTAGGTA TTTTAGAAAC AAAAGGGTTA ACGGCATTGA TCGAAGCATC TGATGCAATG GTTAAGGCTG CAAGTGTTGA ATTAGTTGGC TATCAGCAAA TAGGCTCTGG TTATGTCACG GCTTTCATTC GAGGTGATGT TGCATCTTGC AAAGCCGCTA CTGATGCAGG CTCTGTTGTT GCACAACGCT TAGGTGAGTT AGTGGCTGTC CATGTGATAC CGCGACCACA TCAAGATCTG GAAGCTGTTT TTCCTATCAC AGCAAAAAAG TAA (SEQ ID NO: 52) | 5.53 9551 |
| EutM_SA | *Spirochaeta alkalica* | WP_026245254.1 | MADVQMIALG MIETKGLVAA IEAADAMVKA ANVKLIGKEY IGGGLVTVMV RGDVGAVKAA TDAGAAAAQR IGELVSVHVI PRPHGDAEMI LPSAK (SEQ ID NO: 53) | >His_GS-EutM-SA ATGCATCATC ATCATCACCA CGGCAGCGGT AGCGGCAGCG GTAGCGGCAG CGGTAGCATG ATCGCGTGGG CATGATTGA AACCAAGGGT CTGGTGGCGG CGATTGAAGC GGCGGATGCG ATGGTGAAAG CGGCGAACGT TAAGCTGATC GGCAAAGAGT ACATTGGTGG CGGTCTGGTG ACCGTTATGG TTCGTGGCGA CGTGGGTGCG GTTAAAGCGG CGACCGATGC GGGTGCTGCG GCGGCGCAGC GTATCGGCGA GCTGGTTAGC GTGCACGTTA TTCCGCGTCC GCACGGTGAT GCGGAAATGA TTCTGCCGTAA (SEQ ID NO: 54) | 6.05 9592.3 |
| EutM_TL | *Thauera linaloolentis* | WP_004333389.1 | MEALGLIETK GLVALIEASD AMVKAARVKL VGVKQIGGGF VTAMVRGDVA ACKAATDAGA AAAQRIGELV SVHVIPRPHG DLEEVFPIKM ESGLD (SEQ ID NO: 55) | >His-GS-EutM_TL ATGCATCATC ATCACCACCA CGGTTCTGGT TCTGGTTCTG GTTCTGGTTC TGGTTCTGAA GCCCTGGGAC TGATCGAAAC GAAAGGCCTG GTTGCATTGA TCGAAGCCTC CGACGCCATG GTCAAGGCCG CGCGCGTCAA GTTGGTCGGC GTCAAGCAGA TCGGCGGCGG TTTCGTCACC GCGATGGTGC GTGGCGACGT GGCCGCCTGC AAGGCCGCCA CCGATGCCGG CGCGGCTGCC GCGCAACGGA TTGGCGAACT GGTGTCGGTA CACGTGATTC CGCGTCCGCA CGGCGATCTG GAAGAAGTGT TCCCGATCAA GATGGAAAGC GGACTGGACT GA (SEQ ID NO: 56) | 5.59 9738.4 |

TABLE 3-continued

Toolbox of 14 EutM homologs selected for expression and characterization. Microbial sources, accession numbers, protein sequences and coding sequences for expression in E. coli under the control of a cumate inducible $P_{QS}$ promoter on expression vector pCT5BB

| EutM | Source organism | Accession # | Protein Sequence | Expression construct | pI Mw (Da) |
|---|---|---|---|---|---|
| EutM_TS | Thermoanaero-bacterium saccharolyticum | AFK85252 | MVQEALGMVE TRGLVAAIEA ADAMVKAADV TLIGTEKIGS GLVTVMVRGD VGAVKAATEV GASAASKLGE LVAVHVIPRP HTDVEKILPT IK (SEQ ID NO: 57) | >His-GS-EutM_TS ATGCATCATC ATCATCACCA CGGTAGCGGC AGCGGTAGCG GCAGCGGTAG CGGCAGCGAG GCGCTGGGTA TGGTGGAAAC CCGTGGCCTG GTTGCGGCGA TTGAGGCGGC GGATGCGATG GTGAAGGCGG CGGATGTTAC CCTGATCGGC ACCGAAAAAA TTGGTAGCGG CCTGGTGACC GTTATGGTTC GTGGTGACGT TGGTGCGGTT AAAGCGGCGA CCGAGGTGGG TGCGAGCGCG GCGAGCAAAC TGGGCGAACT GGTTGCGGTG CACGTTATCC CGCGTCCGCA CACCGATGTT GAGAAGATTC TGCCGTAA (SEQ ID NO: 58) | 5.58 9345.0 |
| EutM_BM | Bacillus megaterium | WP_063672411 | MARELTALGM IETKGLVAS VEAADAMVKA ANVHLVDKVH VGGGIVTVLV RGDVGAVKAA TDSGAAAAQR VGELISVHVI PRPHNELESI LPKIDSEL (SEQ ID NO: 59) | >EutM_BM ATGGCAAGAG AACTAACAGC ATTAGGCATG ATTGAAACAA AAGGATTAGT AGCATCAGTA GAGGCAGCAG ACGCAATGGT AAAAGCAGCA AATGTACATT TAGTTGGTAA AGTTCACGTA GGTGGAGGAA TTGTAACGGT TTTAGTACGC GGTGACGTAG GCGCGGTAAA AGCAGCGACA GATTCTGGTG CAGCAGCTGC ACAGCGCGTT GGAGAACTTA TTTCCGTTCA CGTTATCCCA CGCCCACACA ATGAATTAGA AAGTATTTTA CCGAAAATCG ATAGTGAACT ATAA (SEQ ID NO: 60) | 5.72 9956.5 |

Example 2

Bioinformatics Analyses

Homologs of EutM from S. enterica (WP_024798609.1) were identified using NCBI BLASTp (Altschul et al., 1990. J Mol Biol 215:403-410) to search the non-redundant protein sequence database. Searches were carried out using the BLOSUM62 scoring matrix (Eddy SR, 2004. Nat Biotechnol 22:1035-1036) and 500 target sequences were selected, with the Evalue search parameter set to 15. The list of identified EutM protein homologs was manually curated to remove duplicates, incorrectly annotated sequences, or sequences from unidentified bacterial species. Alignments of the curated list of protein sequences were computed using MUSCLE (Edgar RC, 2004. Nucleic Acids Res 32:1792-1797) and phylogenetic analyses were conducted in MEGA 7 (Kumar et al., 2016., Mol Biol Evol 33:1870-1874) using default parameters for the Neighbor-Joining method (Saitou and Nei, 1987. Mol Biol Evol 4:406-425) with a bootstrap test of phylogeny (500 replicates). Phylogenetic trees were visualized using the iTOL interface (Letunic and Bork, 2016. Nucleic Acids Res 44:W242-245), and protein sequence alignments were visualized using the T-Coffee server (Notredame et al., 2000. J Mol Biol 302:205-217). Protein homology models of selected EutM homologs were created using SWISS-MODEL (Biasini et al., 2014. Nucleic Acids Res 42:W252-258). Selection of crystal structure template for modeling in SWISS-MODEL was guided by using NCBI BLASTp to search the Protein Data Bank (Berman et al., 2000. Nucleic Acids Res 28:235-242) for templates with the highest sequence identity to EutM homologs. To ensure that models were comparable and reliable, the length of sequence to be modeled was manually truncated, and QMEAN values were used as an estimate of accuracy (Benkert et al., 2009. Nucleic Acids Res 37:W510-514). Structural models were visualized using the PyMOL Molecular Graphics System, Version 2.0 Schrödinger, LLC.

TABLE 4

Protein sequences, calculated molecular weights and isoelectric points of the EutM homologs identified and characterized in this study. Molecular weights and isoelectric points were calculated using the ProtParam tool on the ExPASy server.

| Protein name/identifier | Protein sequence | Calculated molecular weight (kDa) | Calculated isoelectric point (pI) |
| --- | --- | --- | --- |
| EutM SE WP_024798609.1 | MEALGMIETR GLVALIEASD TMVKAARVKL VGVKQIGGGL CTAMVRGDVA ACKAATDAGA AAAQRIGELV SVHVIPRPHG DLEEVFPISF KGDSNI (SEQ ID NO: 61) | 9.87 | 6.06 |
| EutM DP WP_011190286.1 | MDSLGMIETK GLIALIEASD AMVKAARVQL VGYKQIGAGL VTAIVRGDVA ACKAATDAGA AAAARIGEVV AVHVIPRPHG DLEEVFPFKR DK (SEQ ID NO: 62) | 9.51 | 6.72 |
| EutM MH WP_011784738.1 | NEALGIIETK GLTALIEASD AMVKAARVEL VGYKQIGSGL VTAMVRGDVA ACKAATDAGA AAAQRLGELV AVHVIPRPHG DLEAIFPINP AVKPSGA (SEQ ID NO: 63) | 9.79 | 6.09 |
| EutM TL WP_004333389.1 | MEALGLIETK GLVALIEASD AMVKAARVKL VGVKQIGGGF VTAMVRGDVA ACKAATDAGA AAAQRIGELV SVHVIPRPHG DLEEVFPIKM ESGLD (SEQ ID NO: 64) | 9.74 | 5.59 |
| EutM PH WP_022941754.1 | MDALGILETK GLTALIEASD AMVKAASVEL VGYQQIGSGY VTAFIRGDVA SCKAATDAGS VVAQRLGELV AVHVIPRPHQ DLEAVFPITA KK (SEQ ID NO: 65) | 9.55 | 5.53 |
| EutM CT WP_007505381.1 | MNESLGFIET RGFTAAIEAA DAMLKAANVE IVGSEKIGSG LVSVIVKGDV GAVKAATEVG AEAAGRVGEV IAVHVIPRPH GDIQKLLPTV KDDAV (SEQ ID NO: 66) | 9.65 | 5.02 |
| EutM DT WP_027356248.1 | MTGEALGMVE TRGLVPAIEA ADAMVKAANV VLLGYEKIGS GLVTVMVRGD VGAVKAATDA GAAAAKRVGE VVSVHVIPRP HTDVEKILPA ADRK (SEQ ID NO: 67) | 9.56 | 6.72 |
| EutM TS WP_014757175.1 | MVQEALGMVE TRGLVAAIEA ADAMVKAADV TLIGTEKIGS GLVTVMVRGD VGAVKAATEV GASAASKLGE LVAVHVIPRP HTDVEKILPT IK (SEQ ID NO: 68) | 9.35 | 5.58 |
| EutM AM WP_011971402.1 | MAISNALGMI ETKGLVGAIE AADAMVKAAN VTLLGKEHVG GGLVTVMVRG DVGAVKAATD AGAAAAERVG ELMSVHVIPR PHGEVETILP QIKE (SEQ ID NO: 69) | 9.48 | 5.50 |
| EutM AT WP_027415023.1 | MAREINGALG MIETRGLVAS LEAADAMVKA ANVNIVGKVH VGGGIVTVLV TGDVGAVKAA TEAGSTAAQR VGEIISVHVI PRPHHELGSI LPKLEEY (SEQ ID NO: 70) | 9.90 | 6.04 |
| EutM DA WP_014826595.1 | MNKTEALGLI ETKGLVGAIE AADAMVKAAN VYLIGRELVG | 9.77 | 6.07 |

TABLE 4-continued

Protein sequences, calculated molecular weights and isoelectric points of the EutM homologs identified and characterized in this study. Molecular weights and isoelectric points were calculated using the ProtParam tool on the ExPASy server.

| Protein name/identifier | Protein sequence | Calculated molecular weight (kDa) | Calculated isoelectric point (pI) |
|---|---|---|---|
| | GGLVTVMVRG DVGAVKAATD AGAAAAQRVG ELISVHVIPR PHGDVEMILP QAKKEA (SEQ ID NO: 71) | | |
| EutM FG WP_026677998.1 | MSRELTALGM IETKGLVASV EAADAMVKAA NVHLVGKVHV GGGLVTVLVR GDVGAVKAAT EAGAAAAQRV GELLSVHVIP RPHNELESIL PKVETM (SEQ ID NO: 72) | 9.82 | 6.4 |
| EutM SA WP_026245254.1 | MADVQMIALG MIETKGLVAA IEAADAMVKA ANVKLIGKEY IGGGLVTVMV RGDVGAVKAA TDAGAAAAQR IGELVSVHVI PRPHGDAEMI LPSAK (SEQ ID NO: 73) | 9.59 | 6.05 |

DNA Synthesis and Cloning

Synthetic genes encoding EutM homologs of interest were designed with codon optimization for expression in *E. coli* and were synthesized by GenScript (Piscataway, N.J.). Synthetic genes were assembled into an in-house cumate inducible plasmid (Held et al., 2016. *Sci Rep* 6:24359; Vick et al., *Appl Environ Microbiol* 81:1406-1416) in frame with an N-terminal 6×His tag for protein purification purposes using the NEBUILDER HiFi DNA Assembly Master Mix (New England BioLabs, Inc., Ipswich, Mass.) with reaction conditions and assembly primers as specified by the NEBUILDER design tool. All primers were purchased from Integrated DNA Technologies, Inc. (Coralville, Iowa). Hybrid operons encoding non-His-tagged EutMs and His-EutM-SpyCatcher were assembled in the same way, using synthetic EutMs and previously constructed plasmids (Zhang et al., 2018. *ACS Catal* 8(6):5611-5620) as templates for the amplification of *S. enterica* EutM and EutM-Spy-Catcher genes. To create chimeric proteins, the C-terminus of proteins was altered using the Q5 Site-Directed Mutagenesis Kit (New England BioLabs, Inc., Ipswich, Mass.). Following transformation into *E. coli* ONE SHOT TOP10 cells (ThermoFisher Scientific, Waltham, Mass.), plasmids were isolated from individual colonies using the WIZARD Plus SV Minipreps DNA Purification Kit (Promega, Madison, Wis.) and correct sequences were confirmed by Sanger sequencing (University of Minnesota Genomics Center, Minneapolis, Minn.). Primers used in this study are listed in Table 5, and DNA sequences of all genetic constructs are provided in Tables 6, 7, and 8.

TABLE 5

Primers used to assemble synthetic genes encoding EutM homologs into plasmid backbone pCuminBB

| Primer name | Primer sequence |
|---|---|
| pCuminBB_FWD | GCGGCCGCCT CGAGGCCC (SEQ ID NO: 74) |
| pCuminBB_REV | GGATCCAGAT CCCTCCTTCG (SEQ ID NO: 75) |
| EutM_AM_FWD | cgaaggaggg atctggatcc GCACTGGGTA TGATCGAAAC (SEQ ID NO: 76) |
| EutM_AM_REV | ttgggcctcg aggcggccgc TTACGGCAGA ATGGTTTC (SEQ ID NO: 77) |
| EutM_AT_FWD | cgaaggaggg atctggatcc GCGCGCGAAA TTAACGGC (SEQ ID NO: 78) |
| EutM_AT_REV | ttgggcctcg aggcggccgc TTAATATTCT TCCAGTTTCG GCAGAATG (SEQ ID NO: 79) |
| EutM_CT_FWD | cgaaggaggg atctggatcc GAGAGCCTGG GTTTCATC (SEQ ID NO: 80) |
| EutM_CT_REV | ttgggcctcg aggcggccgc TTACGGCAGC AGCTTCTG (SEQ ID NO: 81) |

TABLE 5-continued

Primers used to assemble synthetic genes encoding EutM homologs into plasmid backbone pCuminBB

| Primer name | Primer sequence |
|---|---|
| EutM_DA_FWD | cgaaggaggg atctggatcc GAGGCGCTGG GCCTGATC (SEQ ID NO: 82) |
| EutM_DA_REV | ttgggcctcg aggcggccgc TTATTTCTTC GCTTGCGGCA GAATC (SEQ ID NO: 83) |
| EutM_DP_FWD | cgaaggaggg atctggatcc GATTCATTAG GAATGATTGA AC (SEQ ID NO: 83) |
| EutM_DP_REV | ttgggcctcg aggcggccgc CTATTTGTCA CGTTTGAAG (SEQ ID NO: 84) |
| EutM_DT_FWD | cgaaggaggg atctggatcc GAGGCGCTGG GTATGGTTG (SEQ ID NO: 85) |
| EutM_DT_REV | ttgggcctcg aggcggccgc TTACGGCAGA ATCTTTTCC ACATC (SEQ ID NO: 86) |
| EutM_FG_FWD | cgaaggaggg atctggatcc CTGACCGCGC TGGGCATG (SEQ ID NO: 87) |
| EutM_FG_REV | ttgggcctcg aggcggccgc TTACGGCAGA ATGCTTTC CAGCTC (SEQ ID NO: 88) |
| EutM_MH_FWD | cgaaggaggg atctggatcc GAGGCGCTGG GTATCATTG (SEQ ID NO: 89) |
| EutM_MH_REV | ttgggcctcg aggcggccgc TTAGTTAATC GGGAAGATC GC (SEQ ID NO: 90) |
| EutM_PH_FWD | cgaaggaggg atctggatcc GACGCTTTAG GTATTTTAG AAAC (SEQ ID NO: 91) |
| EutM_PH_REV | ttgggcctcg aggcggccgc TTACTTTTTT GCTGTGATA GG (SEQ ID NO: 92) |
| EutM_SA_FWD | cgaaggaggg atctggatcc ATGATCGCGC TGGGCATG (SEQ ID NO: 93) |
| EutM_SA_REV | ttgggcctcg aggcggccgc TTACGGCAGA ATCATTTCCG C (SEQ ID NO: 94) |
| EutM_SE_FWD | cgaaggaggg atctggatcc GAAGCATTAG GAATGATTGA AC (SEQ ID NO: 95) |
| EutM_SE_REV | ttgggcctcg aggcggccgc TCAAATGTTG CTGTCGCC (SEQ ID NO: 96) |
| EutM_TL_FWD | cgaaggaggg atctggatcc GAAGCCCTGG GACTGATC (SEQ ID NO: 97) |
| EutM_TL_REV | ttgggcctcg aggcggccgc TCAGTCCAGT CCGCTTTC (SEQ ID NO: 98) |
| EutM_TS_FWD | cgaaggaggg atctggatcc GAGGCGCTGG GTATGGTG (SEQ ID NO: 99) |
| EutM_TS_REV | ttgggcctcg aggcggccgc TTACGGCAGA ATCTTCTCAA CATC (SEQ ID NO: 100) |

TABLE 6

DNA sequences of synthetic genes encoding the EutM homologs that were cloned and characterized in this study. A 6xHis tag (underlined) was included at the 5' end of the gene for protein purification purposes.

| Protein name | Synthetic gene sequence (6xHis underlined) |
|---|---|
| EutM SE | <u>ATGCATCATCATCACCACCAC</u>GGTTCTGGTTCTGGTTCTGGTTCTGGTTCTGGTTC TGAAGCATTAGGAATGATTGAAACCCGGGGCCTGGTTGCGCTGATTGAGGCCTCCG ATGCGATGGTAAAAGCCGCGCGCGTGAAGCTGGTCGGCGTGAAGCAGATTGGCGGT GGCCTGTGTACTGCCATGGTGCGTGGCGATGTGGCGGCGTGCAAAGCCGCAACCGA TGCTGGCGCCGCTGCGGCGCAGCGCATTGGCGAGTTGGTCTCCGTACACGTGATTC CACGCCCGCACGGCGATCTGGAAGAAGTGTTCCCGATCAGCTTCAAAGGCGACAGC AACATTTGA (SEQ ID NO: 101) |
| EutM DP | <u>ATGCATCATCATCACCACCAC</u>GGTTCTGGTTCTGGTTCTGGTTCTGGTTCTGGTTC TGATTCATTAGGAATGATTGAAACTAAGGGCTTGATCGCACTTATTGAAGCTTCAG ATGCAATGGTAAAGGCTGCTCGTGTACAACTTGTAGGTTACAAACAAATTGGTGCT GGTTTGGTAACTGCGATTGTTCGTGGTGATGTTGCAGCATGTAAAGCAGCAACCGA TGCAGGTGCAGCAGCAGCCGCACGTATTGGCGAGGTGGTAGCTGTACACGTTATTC CACGTCCACATGGTGACCTGGAAGAAGTATTTCCCTTCAAACGTGACAAATAG (SEQ ID NO: 102) |
| EutM MH | <u>ATGCATCATCATCATCACCAC</u>GGTAGCGGCAGCGGTAGCGGCAGCGGTAGCGGCAG CAACGAGGCGCTGGGTATCATTGAAACCAAAGGCCTGACCGCGCTGATTGAGGCGA GCGATGCGATGGTGAAGGCGGCGCGTGTTGAACTGGTGGGTTACAAACAGATTGGT AGCGGCCTGGTTACCGCGATGGTGCGTGGCGACGTGGCGGCGTGCAAAGCGGCGAC CGATGCGGGTGCTGCGGCGGCGCAACGTCGGGCGAGCTGGTTGCGGTTCACGTGA TCCCGCGTCCGCACGGTGATCTGGAAGCGATCTTCCCGATTAACCCGGCGGTGAAA CCGAGCGGCGCGTAA (SEQ ID NO: 103) |
| EutM TL | <u>ATGCATCATCATCACCACCAC</u>GGTTCTGGTTCTGGTTCTGGTTCTGGTTCTGGTTC TGAAGCCCTGGGACTGATCGAAACGAAAGGCCTGGTTGCATTGATCGAAGCCTCCG ACGCCATGGTCAAGGCCGCGCGCGTCAAGTTGGTCGGCGTCAAGCAGATCGGCGGC GGTTTCGTCACCGCGATGGTGCGTGGCGACGTGGCCGCCTGCAAGGCCGCCACCGA TGCCGGCGCGGCTGCCGCGCAACGGATTGGCGAACTGGTGTCGGTACACGTGATTC CGCGTCCGCACGGCGATCTGGAAGAAGTGTTCCCGATCAAGATGGAAAGCGGACTG GACTGA (SEQ ID NO: 104) |
| EutM PH | <u>ATGCATCATCATCACCACCAC</u>GGTTCTGGTTCTGGTTCTGGTTCTGGTTCTGGTTC TGACGCTTTAGGTATTTTAGAAACAAAAGGGTTAACGGCATTGATCGAAGCATCTG ATGCAATGGTTAAGGCTCAAGTGTTGAATTAGTTGGCTATCAGCAAATAGGCTCT GGTTATGTCACGGCTTTCATTCGAGGTGATGTTGCATCTTGCAAAGCCGCTACTGA TGCAGGCTCTGTTGTTGCACAACGCTTAGGTGAGTTAGTGGCTGTCCATGTGATAC CGCGACCACATCAAGATCTGGAAGCTGTTTTTCCTATCACAGCAAAAAGTAA (SEQ ID NO: 105) |
| EutM CT | <u>ATGCATCATCATCATCACCAC</u>GGTAGCGGCAGCGGTAGCGGCAGCGGTAGCGGCAG CAACGAGAGCCTGGGTTTCATCGAAACCCGTGGCTTTACCGCGGCGATTGAAGCGG CGGATGCGATGCTGAAGGCGGCGAACGTTGAGATCGTGGGTAGCGAAAAAATTGGT AGCGGCCTGGTGAGCGTTATCGTGAAGGGTGATGTTGGCGCGGTGAAAGCGGCGAC CGAGGTTGGTGCGGAAGCGGCGGGTCGTGTTGGCGAAGTGATCGCGGTTCACGTGA TTCCGCGTCCGCACGGCGACATTCAGAAGCTGCTGCCGACCGTGAAAGATGATGCG GTGTAA (SEQ ID NO: 106) |
| EutM DT | <u>ATGCATCATCATCATCACCAC</u>GGTAGCGGCAGCGGTAGCGGCAGCGGTAGCGGCAG CACCGGCGAGGCGCTGGGTATGGTTGAAACCCGTGGCCTGGTGCCGGCGATTGAGG CGGCGGATGCGATGGTTAAGGCGGCGAACGTGGTTCTGCTGGGTTACGAAAAAATT GGTAGCGGCCTGGTGACCGTTATGGTTCGTGGTGACGTTGGTGCGGTGAAAGCGGC GACCGATGCGGGTGC TGCGGCGGCGAAACGTGTTGGCGAGGTGGTTAGCGTTCACG TGATCCCGCGTCCGCACACCGATGTGGAAAAGATTCTGCCGGCGGCGGATCGCAAA TAA (SEQ ID NO: 107) |
| EutM TS | <u>ATGCATCATCATCATCACCAC</u>GGTAGCGGCAGCGGTAGCGGCAGCGGTAGCGGCAG CGTGCAGGAGGCGCTGGGTATGGTGGAAACCCGTGGCCTGGTTGCGGCGATTGAGG CGGCGGATGCGATGGTGAAGGCGGCGGATGTTACCCTGATCGGCACCGAAAAAATT GGTAGCGGCCTGGTGACCGTTATGGTTCGTGGTGACGTTGGTGCGGTTAAAGCGGC GACCGAGGTGGGTGCGAGCGCGGCGAGCAAACTGGGCGAACTGGTTGCGGTGCACG TTATCCCGCGTCCGCACACCGATGTTGAGAAGATTCTGCCGACCATTAAATAA (SEQ ID NO: 108) |
| EutM AM | <u>ATGCATCATCATCATCACCAC</u>GGCAGCGGTAGCGGCAGCGGTAGCGGCAGCGGTAG CGCGATTAGCAACGCACTGGGTATGATCGAAACCAAGGGCCTGGTTGGTGCGATTG AAGCGGCGGACGCGATGGTTAAGGCGGCGAACGTGACCCTGCTGGGTAAAGAGCAC GTGGGTGGCGGTCTGGTGACCGTTATGGTGCGTGGCGACGTTGGTGCGGTGAAAGC GGCGACCGATGCGGGTGCTGCGGCGGCGGAGCGTGTTGGTGACTGATGAGCGTTC ATGTGATCCCGCGTCCGCACGGCGAGGTGGAAACCATTCTGCCGCAGATTAAAGAA TAA (SEQ ID NO: 109) |

TABLE 6-continued

DNA sequences of synthetic genes encoding the EutM homologs that were cloned and characterized in this study. A 6xHis tag (underlined) was included at the 5' end of the gene for protein purification purposes.

| Protein name | Synthetic gene sequence (6xHis underlined) |
| --- | --- |
| EutM AT | <u>ATGCATCATCATCATCACCACGGCAGCGGTAGCGGCAGCGGTAGCGGCAGCGGTAG<br>CGCGCGCG</u>AAATTAACGGCGCACTGGGTATGATCGAAACCCGTGGTCTGGTGGCGA<br>GCCTGGAGGCGGCGGATGCGATGGTGAAGGCGGCGAACGTTAACATCGTGGGCAAA<br>GTGCACGTTGGTGGCGGTATTGTGACCGTTCTGGTGACCGGCGATGTTGGTGCGGT<br>GAAAGCGGCGACCGAGGCGGGCAGCACCGCGCGCAGCGTGTTGGTGAAATCATTA<br>GCGTTCATGTGATCCCGCGTCCGCACCATGAGCTGGGTAGCATTCTGCCGAAACTG<br>GAAGAATATTAA (SEQ ID NO: 110) |
| EutM DA | <u>ATGCATCATCATCATCACCACGGCAGCGGTAGCGGCAGCGGTAGCGGCAGCGGTAG<br>C</u>AACAAAACCGAGGCGCTGGGCCTGATCGAAACCAAGGGCCTGGTTGGTGCGATTG<br>AGGCGGCGGACGCGATGGTTAAAGCGGCGAACGTGTACCTGATCGGTCGTGAACTG<br>GTGGGTGGCGGTCTGGTGACCGTTATGGTTCGTGGCGACGTTGGTGCGGTGAAAGC<br>GGCGACCGATGCGGGTGCTGCGGCGGCGCAGCGTGTTGGCGAGCTGATCAGCGTTC<br>ACGTGATTCCGCGTCCGCACGGCGATGTGGAAATGATTCTGCCGCAAGCGAAGAAA<br>GAAGCGTAA (SEQ ID NO: 111) |
| EutM FG | <u>ATGCATCATCATCATCACCACGGCAGCGGTAGCGGCAGCGGTAGCGGCAGCGGTAG<br>C</u>AGCCGCGAACTGACCGCGCTGGGCATGATCGAAACCAAGGGTCTGGTTGCGAGCG<br>TGGAAGCGGCGGATGCGATGGTTAAGGCGGCGAACGTTCACCTGGTGGGCAAAGTG<br>CACGTTGGTGGCGGTCTGGTGACCGTTCTGGTGCGTGGCGATGTTGGTGCGGTGAA<br>AGCGGCGACCGAGGCGGGTGCTGCGGCGGCGCAGCGTGTGGGTGAACTGCTGAGCG<br>TTCACGTGATCCCGCGTCCGCACAACGAGCTGGAAAGCATTCTGCCGAAAGTGGAA<br>ACCATGTAA (SEQ ID NO: 112) |
| EutM SA | <u>ATGCATCATCATCATCACCACGGCAGCGGTAGCGGCAGCGGTAGCGGCAGCGGTAG<br>C</u>GCGGATGTGCAGATGATCGCGCTGGGCATGATTGAAACCAAGGGTCTGGTGGCGG<br>CGATTGAAGCGGCGGATGCGATGGTGAAAGCGGCGAACGTTAAGCTGATCGGCAAA<br>GAGTACATTGGTGGCGGTCTGGTGACCGTTATGGTTCGTGGCGACGTGGGTGCGGT<br>TAAAGCGGCGACCGATGCGGGTGCTGCGGCGGCGCAGCGTATCGGCGAGCTGGTTA<br>GCGTGCACGTTATTCCGCGTCCGCACGGTGATGCGGAAATGATTCTGCCGAGCGCG<br>AAATAA (SEQ ID NO: 113) |

TABLE 7

DNA sequences of chimeric proteins that were assembled in this study. A 6xHis tag (underlined) was included at the 5' end of the gene for protein purification purposes. The region encoding EutM TL amino acids 89-95 that was used to replace the C-terminal portion of EutM SE and EutM DP is highlighted.

| Chimeric protein name | Synthetic gene sequence (6xHis underlined) |
| --- | --- |
| EutM SE-TL | <u>ATGCATCATCATCACCACCACGGTTCTGGTTCTGGTTCTGGTTCTGGTTCTGGT<br>TCT</u>GAAGCATTAGGAATGATTGAAACCCGGGGCCTGGTTGCGCTGATTGAGGCC<br>TCCGATGCGATGGTAAAAGCCGCGCGCGTGAAGCTGGTCGGCGTGAAGCAGATT<br>GGCGGTGGCCTGTGTACTGCCATGGTGCGTGGCGATGTGGCGGCGTGCAAAGCC<br>GCAACCGATGCTGGCGCCGCTGCGGCGCAGCGCATTGGCGAGTTGGTCTCCGTA<br>CACGTGATTCCACGCCCGCACGGCGATCTGGAAGAAGTGTTCCCGATCAAGATG<br>GAAAGCGGACTGGACTGA (SEQ ID NO: 114) |
| EutM DP-TL | <u>ATGCATCATCATCACCACCACGGTTCTGGTTCTGGTTCTGGTTCTGGTTCTGGT<br>TCT</u>GATTCATTAGGAATGATTGAAACTAAGGGCTTGATCGCACTTATTGAAGCT<br>TCAGATGCAATGGTAAAGGCTGCTCGTGTACAACTTGTAGGTTACAAACAAATT<br>GGTGCTGGTTTGGTAACTGCGATTGTTCGTGGTGATGTTGCAGCATGTAAAGCA<br>GCAACCGATGCAGGTGCAGCAGCAGCCGCACGTATTGGCGAGGTGGTAGCTGTA<br>CACGTTATTCCACGTCCACATGGTGACCTGGAAGAAGTATTTCCCTTCAAGATG<br>GAAAGCGGACTGGACTAG (SEQ ID NO: 115) |

TABLE 8

DNA sequences of hybrid operons that were assembled in this study. A synthetic leader sequence and ribosome binding site (*italics*) is placed immediately upstream of genes. EutM homologs (bold) lacking any His tag is followed by a second leader sequence and ribosome binding site (*italics*). An N terminally 6xHis tagged (underlined) EutM (SE)-SpyCatcher is placed immediately downstream of the second ribosome binding site.

| Operon name | Synthetic gene sequence |
| --- | --- |
| rbs-EutM (SE)-rbs-His-EutM (SE)-SpyCatcher | *ATGAACGAAGGAGGGATCTGGATCC*ATGGAAGCATTAGGAATGATTGAAACCCG GGGCCTGGTTGCGCTGATTGAGGCCTCCGATGCGATGGTAAAAGCCGCGCGCGT GAAGCTGGTCGGCGTGAAGCAGATTGGCGGTGGCCTGTGTACTGCCATGGTGCG TGGCGATGTGGCGGCGTGCAAAGCCGCAACCGATGCTGGCGCCGCTGCGGCGCA GCGCATTGGCGAGTTGGTCTCCGTACACGTGATTCCACGCCCGCACGGCGATCT GGAAGAAGTGTTCCCGATCAGCTTCAAAGGCGACAGCAACATTTGA*ATGAACGA AGGAGGGATCTGGATCC*<u>ATGCATCATCATCATCACCACCACGGTTCTGGTTCTGGTT CTGGTTCTGGTTCTGGTTCTG</u>AAGCATTAGGAATGATTGAAACCCGGGGCCTGG TTGCGCTGATTGAGGCCTCCGATGCGATGGTAAAAGCCGCGCGCGTGAAGCTGG TCGGCGTGAAGCAGATTGGCGGTGGCCTGTGTACTGCCATGGTGCGTGGCGATG TGGCGGCGTGCAAAGCCGCAACCGATGCTGGCGCCGCTGCGGCGCAGCGCATTG GCGAGTTGGTCTCCGTACACGTGATTCCACGCCCGCACGGCGATCTGGAAGAAG TGTTCCCGATCAGCTTCAAAGGCGACAGCAACATTGTCGACGGGAGTGGTGGCA GCGGAGGCGATAGTGCTACCCATATTAAATTCTCAAAACGTGATGAGGACGGCA AAGAGTTAGCTGGTGCAACTATGGAGTTGCGTGATTCATCTGGTAAAACTATTA GTACATGGATTTCAGATGGACAAGTGAAAGATTTCTACCTGTATCCAGGAAAAT ATACATTTGTCGAAACCGCAGCACCAGACGGTTATGAGGTAGCAACTGCTATTA CCTTTACAGTTAATGAGCAAGGTCAGGTTACTGTAAATGGCTGA (SEQ ID NO: 116) |
| rbs-EutM (MH)-rbs-His-EutM (SE)-SpyCatcher | *ATGAACGAAGGAGGGATCTGGATCC*ATGAACGAGGCGCTGGGTATCATTGAAAC CAAAGGCCTGACCGCGCTGATTGAGGCGAGCGATGCGATGGTGAAGGCGGCGCG TGTTGAACTGGTGGGTTACAAACAGATTGGTAGCGGCCTGGTTACCGCGGATGGT GCGTGGCGACGTGGCGGCGTGCAAAGCGGCGACCGATGCGGGTGCTGCGGCGGC GCAACGTCTGGGCGAGCTGGTTGCGGTTCACGTGATCCCGCGTCCGCACGGTGA TCTGGAAGCGATCTTCCCGATTAACCCGGCGGTGAAACCGAGCGGCCGCGTAAA*T GAACGAAGGAGGGATCTGGATCC*<u>ATGCATCATCATCATCACCACCACGGTTCTGGTT CTGGTTCTGGTTCTGGTTCTG</u>AAGCATTAGGAATGATTGAAACCCGGGGCCTGGTTGCGCTGATTGAGGCCTCCGATGCGATGGTAAAAGCCGCGCGCGTGA AGCTGGTCGGCGTGAAGCAGATTGGCGGTGGCCTGTGTACTGCCATGGTGCGTG GCGATGTGGCGGCGTGCAAAGCCGCAACCGATGCTGGCGCCGCTGCGGCGCAGC GCATTGGCGAGTTGGTCTCCGTACACGTGATTCCACGCCCGCACGGCGATCTGG AAGAAGTGTTCCCGATCAGCTTCAAAGGCGACAGCAACATTGTCGACGGGAGTG GTGGCAGCGGAGGCGATAGTGCTACCCATATTAAATTCTCAAAACGTGATGAGG ACGGCAAAGAGTTAGCTGGTGCAACTATGGAGTTGCGTGATTCATCTGGTAAAA CTATTAGTACATGGATTTCAGATGGACAAGTGAAAGATTTCTACCTGTATCCAG GAAAATATACATTTGTCGAAACCGCAGCACCAGACGGTTATGAGGTAGCAACTG CTATTACCTTTACAGTTAATGAGCAAGGTCAGGTTACTGTAAATGGCTGA (SEQ ID NO: 117) |
| rbs-EutM (FG)-rbs-His-EutM (SE)-SpyCatcher | *ATGAACGAAGGAGGGATCTGGATCC*ATGCGCGAACTGACCGCGCTGGGCATGAT CGAAACCAAGGGTCTGGTTGCGAGCGTGGAAGCGGCGGATGCGATGGTTAAGGC GGCGAACGTTCACCTGGTGGGCAAAGTGCACGTTGGTGGCGGTCTGGTGACCGT TCTGGTGCGTGGCGATGTTGGTGCGGTGAAAGCGGCGACCGAGGCGGGTGCTGC GGCGGCGCAGCGTGTGGGTGAACTGCTGAGCGTTCACGTGATCCCGCGTCCGCA CAACGAGCTGGAAAGCATTCTGCCGAAAGTGGAAACCATGTAA*ATGAACGAAGG AGGGATCTGGATCC*<u>ATGCATCATCATCATCACCACCACGGTTCTGGTTCTGGTTCTG GTTCTGGTTCTGGTTCTG</u>AAGCATTAGGAATGATTGAAACCCGGGGCCTGGTTG CGCTGATTGAGGCCTCCGATGCGATGGTAAAAGCCGCGCGCGTGAAGCTGGTCG GCGTGAAGCAGATTGGCGGTGGCCTGTGTACTGCCATGGTGCGTGGCGATGTGG CGGCGTGCAAAGCCGCAACCGATGCTGGCGCCGCTGCGGCGCAGCGCATTGGCG AGTTGGTCTCCGTACACGTGATTCCACGCCCGCACGGCGATCTGGAAGAAGTGT TCCCGATCAGCTTCAAAGGCGACAGCAACATTGTCGACGGGAGTGGTGGCAGCG GAGGCGATAGTGCTACCCATATTAAATTCTCAAAACGTGATGAGGACGGCAAAG AGTTAGCTGGTGCAACTATGGAGTTGCGTGATTCATCTGGTAAAACTATTAGTA CATGGATTTCAGATGGACAAGTGAAAGATTTCTACCTGTATCCAGGAAAATATA CATTTGTCGAAACCGCAGCACCAGACGGTTATGAGGTAGCAACTGCTATTACCT TTACAGTTAATGAGCAAGGTCAGGTTACTGTAAATGGCTGA (SEQ ID NO: 118) |
| rbs-EutM (TS)-rbs-His-EutM (SE)-SpyCatcher | *ATGAACGAAGGAGGGATCTGGATCC*ATGGTGCAGGAGGCGCTGGGTATGGTGGA AACCCGTGGCCTGGTTGCGGCGATTGAGGCGGCGGATGCGATGGTGAAGGCGGC GGATGTTACCCTGATCGGCACCGAAAAAATTGGTAGCGGCCTGGTGACCGTTAT GGTTCGTGGTGACGTTGGTGCGGTTAAAGCGGCGACCGAGGTGGGTGCGAGCGC GGCGAGCAAACTGGGCGAACTGGTTGCGGTGCACGTTATCCCGCGTCCGCACAC CGATGTTGAGAAGATTCTGCCGACCATTAAATAA*ATGAACGAAGGAGGGATCTG GATCC*<u>ATGCATCATCATCATCACCACCACGGTTCTGGTTCTGGTTCTGGTTCTGGTT CTGGTTCTG</u>AAGCATTAGGAATGATTGAAACCCGGGGCCTGGTTGCGCTGATTG AGGCCTCCGATGCGATGGTAAAAGCCGCGCGCGTGAAGCTGGTCGGCGTGAAGC AGATTGGCGGTGGCCTGTGTACTGCCATGGTGCGTGGCGATGTGGCGGCGTGCA AAGCCGCAACCGATGCTGGCGCCGCTGCGGCGCAGCGCATTGGCGAGTTGGTCT CCGTACACGTGATTCCACGCCCGCACGGCGATCTGGAAGAAGTGTTCCCGATCA GCTTCAAAGGCGACAGCAACATTGTCGACGGGAGTGGTGGCAGCGGAGGCGATA |

TABLE 8-continued

DNA sequences of hybrid operons that were assembled in this study. A synthetic leader sequence and ribosome binding site (*italics*) is placed immediately upstream of genes. EutM homologs (bold) lacking any His tag is followed by a second leader sequence and ribosome binding site (*italics*). An N terminally 6xHis tagged (underlined) EutM (SE)-SpyCatcher is placed immediately downstream of the second ribosome binding site.

| Operon name | Synthetic gene sequence |
|---|---|
| | GTGCTACCCATATTAAATTCTCAAAACGTGATGAGGACGGCAAAGAGTTAGCTG<br>GTGCAACTATGGAGTTGCGTGATTCATCTGGTAAAACTATTAGTACATGGATTT<br>CAGATGGACAAGTGAAAGATTTCTACCTGTATCCAGGAAAATATACATTTGTCG<br>AAACCGCAGCACCAGACGGTTATGAGGTAGCAACTGCTATTACCTTTACAGTTA<br>ATGAGCAAGGTCAGGTTACTGTAAATGGCTGA (SEQ ID NO: 119) |

Recombinant Expression of Proteins in *E. coli*

*E. coli* T7 Express (C2566) (New England BioLabs, Inc., Ipswich, Mass.) cells were transformed with plasmids of interest, and colonies were isolated on Lysogeny Broth (LB) agar plates supplemented with ampicillin (100 μg mL$^{-1}$) overnight at 37° C. Individual colonies were used to inoculate 50 mL of LB medium supplemented with ampicillin (100 μg mL$^{-1}$) and cultures were grown overnight at 37° C. with rotation at 220 rpm. A volume of 5 mL of the overnight culture was used to inoculate 500 mL of fresh LB medium plus ampicillin (100 μg mL$^{-1}$) and cultures were incubated at 37° C. with rotation at 220 rpm. Once an optical density of $A_{600}$=0.4-0.6 was reached, protein expression was induced by adding cumate (50 and the cultures were incubated at 37° C. with rotation at 220 rpm overnight. The cells were harvested by centrifugation at 4,000 rpm for 30 minutes at 4° C. in a Beckman J2-HS centrifuge. The supernatant was removed and the cell pellets were stored at −20° C. until needed.

Protein Purification by Ni$^{2+}$ Affinity Chromatography

For protein purification of EutM homologs, cell pellets were resuspended in 30 mL Buffer A (20 mM Tris-HCL, 250 mM NaCL, 5 mM imidazole, 4 M urea, pH 7.5) and were disrupted by sonication on ice (4 minutes, pulse on 1 second, and off for 2 seconds at 30% power). The soluble protein was separated from cell debris by centrifugation at 12,000 rpm for 20 minutes at 4° C. in a Beckman J2-HS centrifuge. The soluble protein was loaded onto a 5 mL HISTRAP FF (GE Healthcare, Chicago, Ill.) column (pre-equilibrated with Buffer A) at a flow rate of 2 mL min$^{-1}$. After soluble protein was loaded, the column was washed with Buffer A at a flow rate of 5 mL min$^{-1}$ for at least 5 column volumes. Nonspecifically bound proteins were removed from the column by washing with a gradient of 25% Buffer B (20 mM Tris-HCL, 250 mM NaCL, 250 mM imidazole, 4 M urea, pH 7.5) at 5 mL min$^{-1}$. The pure His-tagged protein was then eluted in two column volumes of 100% Buffer B. Proteins were assessed for purity by SDS-PAGE. Finally, the purified proteins were dialyzed against 500 mL Buffer C (50 mM Tris-HCL, 12.5 mM MgCl$_2$, pH 8.0) overnight at 4° C. using a 3K cutoff membrane. Chimeric proteins (His-EutM SE-TL and His-EutM DP-TL) were purified using the same procedure. For purification of proteins expressed from hybrid operons (EutM(homolog) His-EutM(SE)-SpyCatcher), the same procedure was followed with the exception that purification buffers did not contain any urea.

Negative Stain Transmission Electron Microscopy

Concentrations of dialyzed, purified proteins were measured using the BCA Assay Protein Kit (Pierce, ThermoFisher Scientific, Waltham, Mass.) and were normalized to 1.0 mg/mL. For negative staining, 10 μL of protein was applied to the surface of a 200 μm formvar/carbon-coated copper grid (Electron Microscopy Sciences, Hatfield, Pa.). An equal volume of Trump's fixative (Electron Microscopy Sciences, Hatfield, Pa.) was added to the surface of the grid, and the protein/fixative drop was allowed to settle for two minutes. Excess fluid was wicked away from the grid using filter paper. The surface of the grid was rinsed with 10 μL deionized water and excess fluid was removed. The protein on the grid was stained by applying 10 μL uranyl acetate (1%) (Electron Microscopy Sciences, Hatfield, Pa.); excess fluid was removed immediately to prevent over-staining, and grids were allowed to air dry completely. Grids were visualized and imaged using a Phillips CM12 transmission electron microscope within the University Imaging Center (University of Minnesota, Saint Paul, Minn.).

Cargo Loading on Protein Scaffolds and Fluorescence Microscopy

Purified hybrid scaffolds EutM(homolog) His-EutM(SE)-SpyCatcher (~1 mg mL$^{-1}$) were mixed at a 1:1 molar ratio with purified SpyTag-GFP or GFP as a control (Zhang et al., 2018. *ACS Catal* 8(6):5611-5620) in PBS buffer (pH 7.4). The samples were incubated at room temperature for 30 minutes to allow covalent bond formation. Following incubation, 10 μL of each sample was pipetted onto a microscope slide. Fluorescence images of cargo loaded scaffolds were collected using a Nikon Eclipse 90i microscope using a 120 W X-Cite epi-fluorescence illuminator filter set (excitation filter 470-490 nm for GFP), and a 100×, 1.4 n.a. plan apo objective lens. DIC images were also collected. Images were analyzed using Nikon NIS Elements Viewer 4.6.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A protein scaffold comprising:
   a plurality of EutM subunits comprising a first EutM subunit and a second EutM subunit; and
   a multi-enzyme cascade comprising:
   a first enzyme attached to the first EutM subunit; and
   a second enzyme attached to the second EutM subunit, such that at least one of the first enzyme and the second enzyme is more stable when attached to the EutM subunit than when the enzyme is unattached to the EutM subunit.

2. The protein scaffold of claim 1 wherein the multi-enzyme cascade comprises more than two enzymes.

3. The protein scaffold of claim 2 wherein a third enzyme is attached to a third EutM subunit.

4. The protein scaffold of claim 1, wherein at least one enzyme is covalently attached to a EutM subunit.

5. The protein scaffold of claim 1, wherein at least one enzyme is ionically attached to a EutM subunit.

6. The protein scaffold of claim 1, wherein at least one enzyme is attached to a EutM subunit through an affinity interaction.

7. The protein scaffold of claim 6 wherein the affinity interaction comprises peptide-peptide affinity.

8. The protein scaffold of claim 6 wherein the affinity interaction comprises protein-protein affinity.

9. The protein scaffold of claim 1, wherein at least one enzyme is attached to a chemically-modified amino acid residue of the EutM subunit.

10. A protein scaffold comprising:
    a plurality of EutM subunits comprising a first EutM subunit and a second EutM subunit; and
    an enzyme attached to a EutM subunit, such that the enzyme is more stable when attached to the EutM subunit than when the enzyme is unattached to the EutM subunit.

11. The protein scaffold of claim 10, wherein the enzyme is covalently attached to a EutM subunit.

12. The protein scaffold of claim 10, wherein the enzyme is ionically attached to a EutM subunit.

13. The protein scaffold of claim 10, wherein the enzyme is attached to a EutM subunit through an affinity interaction.

14. The protein scaffold of claim 13, wherein the affinity interaction comprises peptide-peptide affinity.

15. The protein scaffold of claim 13, wherein the affinity interaction comprises protein-protein affinity.

16. The protein scaffold of claim 10, wherein the enzyme is attached to a chemically-modified amino acid residue of a EutM subunit.

17. A protein scaffold comprising:
    a plurality of EutM subunits; and
    a first multi-enzyme cascade comprising:
    a first enzyme attached to a first EutM subunit; and
    a second enzyme attached to a second EutM subunit; and
    a second multi-enzyme cascade, different than the first multi-enzyme cascade, the second multi-enzyme cascade comprising:
    a third enzyme attached to a third EutM subunit; and
    a fourth enzyme attached to a fourth EutM subunit.

18. The protein scaffold of claim 17, wherein the first multi-enzyme cascade or the second multi-enzyme cascade comprises more than two enzymes.

19. The protein scaffold of claim 17, wherein at least one enzyme is covalently attached to a EutM subunit.

20. The protein scaffold of claim 17, wherein at least one enzyme is ionically attached to a EutM subunit.

21. The protein scaffold of claim 17, wherein at least one enzyme is attached to a EutM subunit through an affinity interaction.

22. The protein scaffold of claim 21, wherein the affinity interaction comprises peptide-peptide affinity.

23. The protein scaffold of claim 21, wherein the affinity interaction comprises protein-protein affinity.

24. The protein scaffold of claim 17, wherein at least one enzyme is attached to a chemically-modified amino acid residue of the EutM subunit.

25. The protein scaffold of claim 17, wherein at least one enzyme is more stable when attached to the EutM subunit than when the enzyme is unattached to the EutM subunit.

26. The protein scaffold of claim 1, wherein catalyst recycling is greater when at least one of the first enzyme and second enzyme is attached to the EutM subunit than when the enzyme is unattached to the EutM subunit.

27. The protein scaffold of claim 10, wherein catalyst recycling is greater when the enzyme is attached to the EutM subunit than when the enzyme is unattached to the EutM subunit.

28. The protein scaffold of claim 1, wherein reaction enantioselectivity is greater when at least one of the first enzyme and second enzyme is attached to the EutM subunit than when the enzyme is unattached to the EutM subunit.

29. The protein scaffold of claim 10, wherein reaction enantioselectivity is greater when the enzyme is attached to the EutM subunit than when the enzyme is unattached to the EutM subunit.

30. The protein scaffold of claim 1, wherein reaction time is reduced when at least one of the first enzyme and second enzyme is attached to the EutM subunit than when the enzyme is unattached to the EutM subunit.

31. The protein scaffold of claim 10, wherein reaction time is reduced when the enzyme is attached to the EutM subunit than when the enzyme is unattached to the EutM subunit.

* * * * *